(12) United States Patent
Kahn et al.

(10) Patent No.: US 7,531,320 B2
(45) Date of Patent: May 12, 2009

(54) MODULATION OF β-CATENIN/TCF-ACTIVATED TRANSCRIPTION

(75) Inventors: Michael Kahn, Kirkland, WA (US); SeWoong Oh, Suwon (KR); DaeHoon Kim, Suwon (KR); JongRyul Ha, Suwon (KR); Katayoon Hojjati-Emami, Seattle, WA (US)

(73) Assignee: Choongwae Pharma Corporation, Seoul (KR)

( * ) Notice: Subject to any disclaimer, the term of this patent is extended or adjusted under 35 U.S.C. 154(b) by 505 days.

(21) Appl. No.: 10/928,626

(22) Filed: Aug. 27, 2004

(65) Prior Publication Data

US 2005/0059628 A1    Mar. 17, 2005

Related U.S. Application Data

(60) Provisional application No. 60/498,451, filed on Aug. 28, 2003.

(51) Int. Cl.
*C12P 21/06*    (2006.01)
(52) U.S. Cl. .................................... 435/69.1
(58) Field of Classification Search .................. None
See application file for complete search history.

(56) References Cited

U.S. PATENT DOCUMENTS

| | | | |
|---|---|---|---|
| 5,440,013 A | 8/1995 | Kahn | 530/317 |
| 5,475,085 A | 12/1995 | Kahn | 530/317 |
| 5,618,914 A | 4/1997 | Kahn | 530/317 |
| 5,658,784 A | 8/1997 | Eckner et al. | 435/325 |
| 5,670,155 A | 9/1997 | Kahn | 424/208.1 |
| 5,672,681 A | 9/1997 | Kahn | 530/317 |
| 5,693,325 A | 12/1997 | Kahn | 424/188.1 |
| 5,710,245 A | 1/1998 | Kahn | 530/324 |
| 5,840,833 A | 11/1998 | Kahn | 530/300 |
| 5,859,184 A | 1/1999 | Kahn et al. | 530/300 |
| 5,929,237 A | 7/1999 | Kahn | 544/279 |
| 6,013,458 A | 1/2000 | Kahn et al. | 435/7.1 |
| 6,020,331 A | 2/2000 | Kahn | 514/221 |
| 6,063,585 A | 5/2000 | Montminy | 435/7.21 |
| 6,117,896 A | 9/2000 | Qabar et al. | 514/384 |
| 6,184,223 B1 | 2/2001 | Kahn et al. | 514/249 |
| 6,245,764 B1 | 6/2001 | Kahn et al. | 514/248 |
| 6,294,525 B1 | 9/2001 | Stasiak et al. | 514/183 |
| 6,372,744 B1 | 4/2002 | Qabar et al. | 514/248 |
| 6,413,963 B2 | 7/2002 | Kahn et al. | 514/249 |
| 6,440,955 B1 | 8/2002 | Stasiak et al. | 514/183 |
| 6,548,500 B2 | 4/2003 | Kahn et al. | 514/249 |
| 6,762,185 B1 | 7/2004 | Kahn et al. | 514/249 |
| 2001/0039274 A1 | 11/2001 | Kahn et al. | 514/221 |
| 2002/0022620 A1 | 2/2002 | Kahn et al. | 514/221 |
| 2002/0065416 A1 | 5/2002 | Stasiak et al. | 544/350 |
| 2002/0068695 A1 | 6/2002 | Scolastico et al. | 514/9 |
| 2003/0021773 A1 | 1/2003 | Moroder et al. | 424/94.1 |
| 2003/0027819 A1 | 2/2003 | Qabar et al. | 514/224.2 |
| 2003/0105103 A1 | 6/2003 | Golebiowski et al. | 514/249 |
| 2004/0072831 A1* | 4/2004 | Moon et al. | 514/243 |

FOREIGN PATENT DOCUMENTS

| | | |
|---|---|---|
| EP | 1 054 059 A1 | 11/2000 |
| EP | 1 302 104 A1 | 4/2003 |
| JP | 11-32767 A | 2/1999 |
| WO | WO 94/03494 A1 | 2/1994 |
| WO | WO 98/03652 A2 | 1/1998 |
| WO | WO 99/18124 A1 | 4/1999 |
| WO | WO 01/00210 A1 | 1/2001 |
| WO | WO 01/16135 A2 | 3/2001 |
| WO | WO 02/065134 A2 | 8/2002 |
| WO | WO 03/000730 A1 | 1/2003 |
| WO | WO 03/006447 A2 | 1/2003 |
| WO | WO 03/031448 A1 | 4/2003 |
| WO | WO 03/068961 A2 | 8/2003 |

OTHER PUBLICATIONS

Reya et al., A role of Wnt signaling in self-renewal of haematopoietic stem cells, nature, vol. 423, May 2003, pp. 409-414.*
Daniels, D.L. et al., "β-catenin: molecular plasticity and drug design," *Trends in Biochemical Sciences*, 26(11):672-678, Nov. 11, 2001.
Emami, K.H. et al., "A small molecular inhibitor of β-catenin/CREB-binding protein transcription," *PNAS*, 101(34):12682-12687, Aug. 24, 2004.
Morin, P.J., "β-catenin signaling and cancer," *BioEssays*, 21(12):1021-1030, Dec. 1999.
Morin, P.J. et al., "Activation of β-Catenin-Tcf Signaling in Colon Cancer by Mutations in β-Catenin or APC," *Science*, 275:1787-1790, Mar. 21, 1997.
Oving, I.M. and Clevers, H.C., "Molecular causes of colon cancer," *European Journal of Clinical Investigation*, 32(6):448-457, Jun. 2002.
Bienz, M., and Clevers, H., "Linking Colorectal Cancer to Wnt Signaling," *Cell*, 103:311-320, Oct. 13, 2000.
Chen, S. et al., "Wnt-1 Signaling Inhibits Apoptosis by Activating β-Catenin/T Cell Factor-mediated Transcription," *The Journal of Cell Biology* 152(1): 87-96, Jan. 8, 2001.
Easwaran, V. et al., "Cross-regulation of β-catenin-LEF/TCF and retinoid signaling pathways," *Current Biology*, 9(23):1415-1418, Nov. 22, 1999.
Gottardi, C.J. and Gumbiner, B.M., "Adhesion signaling: How β-catenin interacts with its partners," *Current Biology*, 11(19):R792-R794, 2001.
Graham, T.A. et al., "Crystal Structure of a β-Catenin/Tcf Complex," *Cell*, 103:885-896, Dec. 8, 2000.
Graham, T.A. et al., "Tcf4 can specifically recognize β-catenin using alternative conformations," *Nature Structural Biology*, 8(12):1048-1052, Dec. 2001.

(Continued)

*Primary Examiner*—Karen Cochrane Carlson
(74) *Attorney, Agent, or Firm*—Seed Intellectual Property Law Firm PLLC

(57) ABSTRACT

The present invention provides compounds and methods for modulating transcription activated by β-catenin/TCF, such as the selective inhibition of genes targeted by the Wnt/β-catenin pathway.

22 Claims, 25 Drawing Sheets

OTHER PUBLICATIONS

Hecht, A. et al., "Functional Characterization of Multiple Transactivating Elements in β-Catenin, Some of Which Interact with the TATA-binding Protein in Vitro," *The Journal of Biological Chemistry*, 274(5):18017-18025, Jun. 18, 1999.

Hecht, A. et al., "The p300/CBP acetyltransferases function as transcriptional coactivators of β-catenin in vertebrates," *The EMBO Journal*, 19(9):1839-1850, 2000.

Minucci, S. and Pelicci, P.G., "Retinoid receptors in health and disease: co-regulators and the chromatin connection," *Seminars in Cell & Developmental Biology*, 10:215-225, 1999.

Moon, R.T. et al., "The Promise and Perils of Wnt Signaling Through β-Catenin," *Science*, 296:1644-1646, May 31, 2002.

Poy, F. et al., "Structure of a human Tcf4-β-catenin complex," *Nature Structural Biology*, 8(12):1053-1057, Dec. 2001.

Rebel, V.I. et al., "Distinct roles for CREB-binding protein and p300 in hematopoietic stem cell self-renewal," *PNAS*, 99(23):14789-14794, Nov. 12, 2002.

Shikama, N. et al., "The p300/CBP family: integrating signals with transcription factors and chromatin," *Trends in Cell Biology*, 7:230-236, Jun. 1997.

Staal, F.J.T. et al., "Wnt signals are transmitted through N-terminally dephosphorylated βcatenin," *EMBO reports*, 3(1):63-68, 2002.

Takemaru, K. and Moon, R.T., "The Transcriptional Coactivator CBP Interacts with β-Catenin to Activate Gene Expression," *The Journal of Cell Biology*, 149(2):249-254, Apr. 17, 2000.

Vleminckx, K. et al., "The C-terminal transactivation domain of β-catenin is necessary and sufficient for signaling by the LEF-1/β-catenin complex in *Xenopus laevis*," *Mechanisms of Development*, 81:65-74, 1999.

Zaloom, J. and Roberts, D.C., "Preparation of Azido Derivatives from Amino Acids and Peptides by Diazo Transfer," *J. Org. Chem.*, 46(25):5173-5176, 1981.

Cowin, P. "Unraveling the cytoplasmic interactions of the cadherin superfamily," *Proc. Natl. Acad. Sci., USA*, 91(23):10759-10761, Nov. 8, 1994.

Filipak, M. et al., "Tumor necrosis factor inhibits the terminal event in mesenchymal stem cell differentiation," *Journal of Cellular Physiology*, Medline Abstract—NLM3192620, 137(2), Nov. 1988.

Gusterson, R.J. et al., "The Transcriptional Co-activators CREB-binding Protein (CBP) and p300 Play a Critical Role in Cardiac Hypertrophy That Is Dependent on Their Histone Acetyltransferase Activity," *The Journal of Biological Chemistry*, 278(9):6838-6847, Feb. 28, 2003.

Hedgepeth, C.M. et al., "Activation of the Wnt Signaling Pathway: A Molecular Mechanism for Lithium Action," *Developmental Biology*, 185(1):82-91, Article No. DB978552, May 1, 1997.

Kielman, M.F. et al., "Apc modulates embryonic stem-cell differentiation by controlling the dosage of β-catenin signaling," *Nature Genetics*, 32(4):594-605, Dec. 20, 2002.

Klein, P.S. and Melton, D.A., "A molecular mechanism for the effect of lithium on development," *Proc. Natl. Acad. Sci., USA*, 93(16):8455-8459, Aug. 6, 1996.

Lévy, L. et al., "Acetylation of β-Catenin by p300 Regulates β-Catenin-Tcf4 Interaction," *Molecular and Cellular Biology*, 24(8):3404-3414, Apr. 2004.

Miyagishi, M. et al., "Regulation of Lef-mediated Transcription and p53-dependent Pathway by Associating β-Catenin with CBP/p300." *The Journal of Biological Chemistry*, 275(45):35170-35175, Nov. 11, 2000.

Munemitsu, S. et al., "Regulation of intracellular β-catenin levels by the adenomatous polyposis coli (APC) tumor-suppressor protein," *Proc. Natl. Acad. Sci., USA*, 92(7):3046-3050, Mar. 1995.

Nelson, W.J. and Nusse, R., "Convergence of Wnt, β-Catenin, and Cadherin Pathways," *Science*, 303(5663):1483-1487, Mar. 5, 2004.

Wodarz, A. and Nusse, R., "Mechanisms of Wnt Signaling in Development," *Annu. Rev. Cell Dev. Biol.*, 14:59-88, 1988.

\* cited by examiner

Compound 1

Compound 2

Compound 3
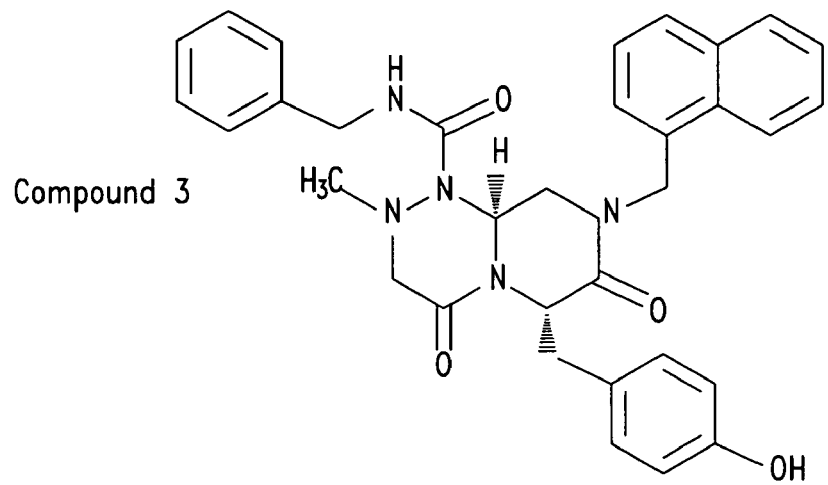
Compound 4
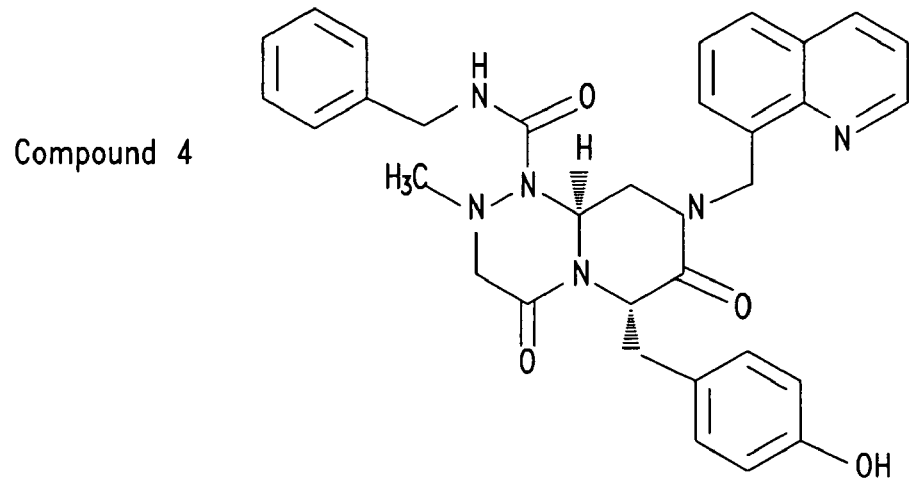
Compound 5
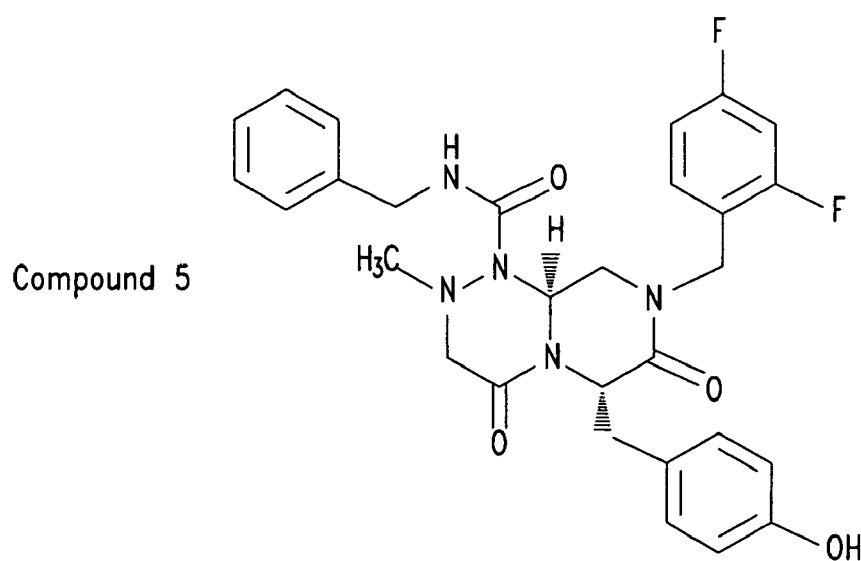
*FIG. 1A(ii)*

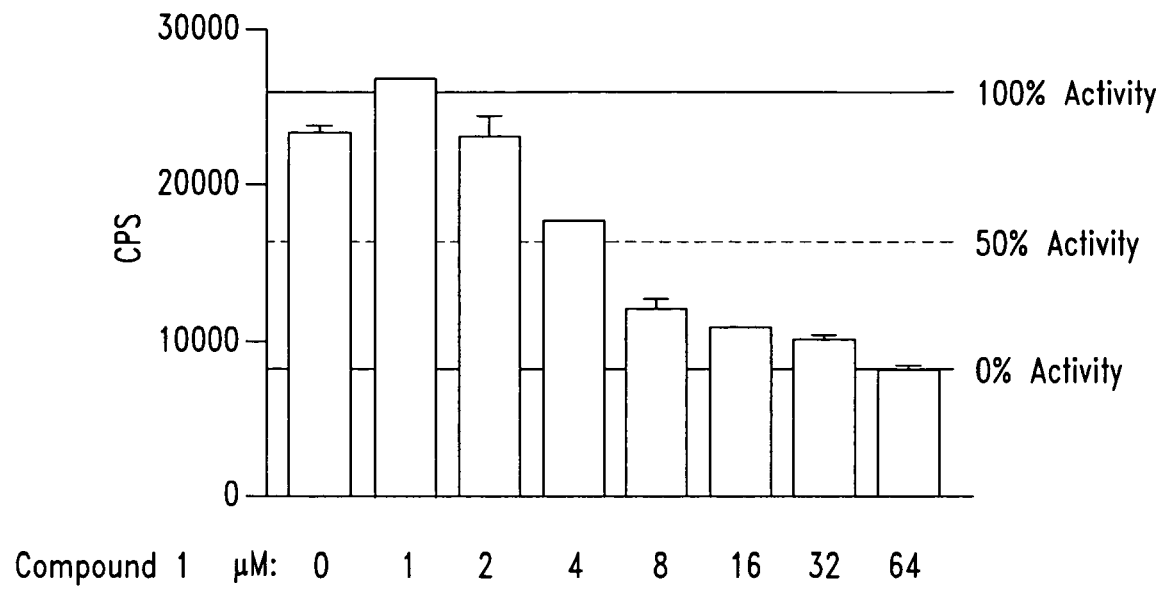
FIG. 1B(i)
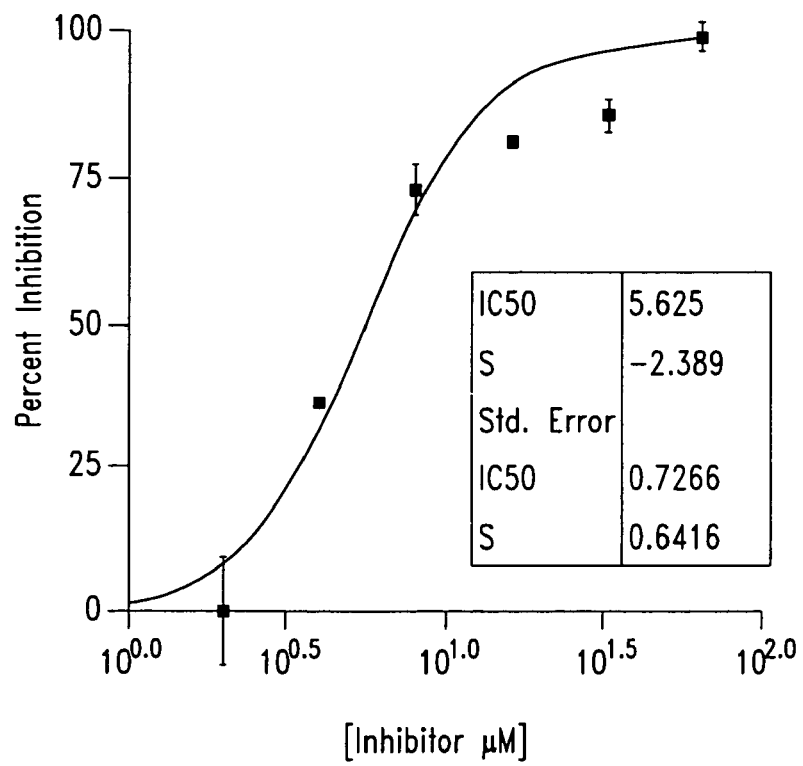
FIG. 1B(ii)

CBP: C1 C2 C3 C1 C2 C3 C1 C2 C3 P1 P2 P3 P1 P2 P3 :p300
Compound 2 (100 μM):  −  −  −  +  +  +  +  +  +  +  +  +  +  +  +
Compound 1 (150 μM):  −  −  −  −  −  −  +  +  +  −  −  −  +  +  +

1  2  3  4  5  6  7  8  9  10  11 12 13 14 15

CBP: C1 C2 C3 C1 C2 C3 C1 C2 C3 P1 P2 P3 P1 P2 P3 :p300

1  2  3  4  5  6  7  8  9 10 11 12 13 14 15

| | | | | | | |
|---|---|---|---|---|---|---|
| hTCF4 | 15 | NDELIRFKD---- | EGEQEE | | | |
| hTCF4 | 15 | NDELIRFKD---- | EGEQEE | | | |
| E-cadherin | 673 | YDSLLVFDY---- | EG-------- | SGS | -----AA | SLSSL |
| APC-3 | 1485 | ADTLLHFAT---- | ES-------- | SCS | -----SS | LSAL |
| hAPC-A | 1020 | LDTPINYSLKYSD | EQ | | | |
| hAPC-1 | 1265 | EDTPICFSRCS-- | ---------- | ---- | ------- | SLSSL |
| hICAT | 65 | EDVVMAFSRS--- | ETEDR | | | |
| hCBP | 41 | EDELIPNGG---- | ELGLLNS--- | SGS | ------- | SASSP |
| mCBP | 41 | EDELIPNG----- | ELSLLNS--- | SGS | ------- | SASSP |
| hp300 | 45 | EDELINST----- | ELGLTNS--- | SGS | ------- | GGPGQ |
| hp300 | 45 | EDELINST----- | ELGLTNS--- | SGS | ------- | GGPGQ | hCBP:  MAENLLD-GPPNPKRAKLSSPGFSANDN---TDFGSLFDLENDLP
hp300: MAENVVEPGPPSAKRPKLSSPALSASASDGTDFGSLFDLEHDLP

DELIPNGGELSLLNSG------NL---VPDAASKHKQLSELLRGGSSGSSINPGIGNVSASSP
DELINST-ELGLTNGGDINQLQTSLGMVQDAASKHKQLSELLR---SGSSPNLMGVGGPGQV-

----VQQ---GLGGQAQGQPNSTN
MASQAQQSSPGLGL

FIG. 3F

SW480 Cells

CBP: Red
β-catenin: Green

Control

Compound 1

SEQUENCE LISTING

<160> NUMBER OF SEQ ID NOS: 55

<210> SEQ ID NO 1
<211> LENGTH: 330
<212> TYPE: DNA
<213> ORGANISM: Homo sapiens

<400> SEQUENCE: 1

```
tgaggaatca acagccgcca tcttgtcgcg gacccgaccg gggcttcgag cgcgatctac      60
tcggccccgc cggtcccggg ccccacaacc gcccgcgctc gctcctctcc ctcgcagccg     120
gcagggcccc cgaccccgt  ccgggccctc gccggcccgg ccgcccgtgc ccggggctgt     180
tttcgcgagc aggtgaaaat ggctgagaac ttgctggacg gaccgcccaa ccccaaaaga     240
gccaaactca gctcgcccgg tttctcggcg aatgacagca cagattttgg atcattgttt     300
gacttggaaa atgatcttcc tgatgagctg                                     330
```

<210> SEQ ID NO 2
<211> LENGTH: 111
<212> TYPE: PRT
<213> ORGANISM: Homo sapiens

<400> SEQUENCE: 2

```
Met Ala Glu Asn Leu Leu Asp Gly Pro Pro Asn Pro Lys Arg Ala Lys
 1               5                  10                  15

Leu Ser Ser Pro Gly Phe Ser Ala Asn Asp Ser Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn
            100                 105                 110
```

<210> SEQ ID NO 3
<211> LENGTH: 340
<212> TYPE: DNA
<213> ORGANISM: Homo sapiens

<400> SEQUENCE: 3

```
ccttgtttgt gtgctaggct ggggggggaga gagggcgaga gagagcgggc gagagtgggc      60
aagcaggacg ccgggctgag tgctaactgc gggacgcaga gagtgcggag gggagtcggg     120
```

```
tcggagagag gcggcagggg ccagaacagt ggcaggggc cggggcgca cgggctgagg    180 cgaccccag cccctcccg tccgcacaca ccccaccgc ggtccagcag ccggcccggc    240
gtcgacgcta gggggacca ttacataacc cgcgccccgg ccgtcttctc ccgccgccgc    300
ggcgcccgaa ctgagcccgg ggcgggcgct ccagcactgg                        340
```

```
<210> SEQ ID NO 4
<211> LENGTH: 117
<212> TYPE: PRT
<213> ORGANISM: Homo sapiens

<400> SEQUENCE: 4

Met Ala Glu Asn Val Val Glu Pro Gly Pro Pro Ser Ala Lys Arg Pro
 1               5                  10                  15

Lys Leu Ser Ser Pro Ala Leu Ser Ala Ser Asp Gly Thr Asp
            20                  25                  30

Phe Gly Ser Leu Phe Asp Leu Glu His Asp Leu Pro Asp Glu Leu Ile
            35                  40                  45

Asn Ser Thr Glu Leu Gly Leu Thr Asn Gly Gly Asp Ile Asn Gln Leu
 50                  55                  60

Gln Thr Ser Leu Gly Met Val Gln Asp Ala Ala Ser Lys His Lys Gln
65                   70                  75                  80

Leu Ser Glu Leu Leu Arg Ser Gly Ser Ser Pro Asn Leu Asn Met Gly
                85                  90                  95

Val Gly Gly Pro Gly Gln Val Met Ala Ser Gln Ala Gln Gln Ser Ser
            100                 105                 110

Pro Gly Leu Gly Leu
        115
```

```
<210> SEQ ID NO 5
<211> LENGTH: 108
<212> TYPE: PRT
<213> ORGANISM: Mus musculus

<400> SEQUENCE: 5

Met Ala Glu Asn Leu Leu Asp Gly Pro Pro Asn Pro Lys Arg Ala Lys
 1               5                  10                  15

Leu Ser Ser Pro Gly Phe Ser Ala Asn Asp Asn Thr Asp Phe Gly Ser
            20                  25                  30

Leu Phe Asp Leu Glu Asn Asp Leu Pro Asp Glu Leu Ile Pro Asn Gly
            35                  40                  45

Glu Leu Ser Leu Leu Asn Ser Gly Asn Leu Val Pro Asp Ala Ala Ser
 50                  55                  60

Lys His Lys Gln Leu Ser Glu Leu Leu Arg Gly Gly Ser Gly Ser Ser
65                   70                  75                  80

Ile Asn Pro Gly Ile Gly Asn Val Ser Ala Ser Ser Pro Val Gln Gln
                85                  90                  95

Gly Leu Gly Gly Gln Ala Gln Gly Gln Pro Asn Ser
            100                 105
```

```
<210> SEQ ID NO 6
<211> LENGTH: 330
<212> TYPE: DNA
<213> ORGANISM: Mus musculus

<400> SEQUENCE: 6
atggccgaga acttgctgga cggaccgccc aaccccaaac gagccaaact cagctcgccc    60
```

```
ggcttctccg cgaatgacaa cacagatttt ggatcattgt ttgacttgga aaatgacctt      120
cctgatgagc tgatccccaa tggagaatta agccttttaa acagtgggaa ccttgttcca      180
gatgctgcgt ccaaacataa acaactgtca gagcttctta gaggaggcag cggctctagc      240
atcaacccag ggataggcaa tgtgagtgcc agcagccctg tgcaacaggg ccttggtggc      300
caggctcagg ggcagccgaa cagtacaaac                                       330
```

```
<210> SEQ ID NO 7
<211> LENGTH: 40
<212> TYPE: DNA
<213> ORGANISM: Artificial Sequence
<220> FEATURE:
<223> OTHER INFORMATION: forward primer used to clone the C-terminally
      truncated constructs of CBP

<400> SEQUENCE: 7
gatatctgag ctcgtggatc cgatggccga gaacttgctg                             40
```

```
<210> SEQ ID NO 8
<211> LENGTH: 41
<212> TYPE: DNA
<213> ORGANISM: Artificial Sequence
<220> FEATURE:
<223> OTHER INFORMATION: reverse primer used to clone the C-terminally
      truncated constructs of CBP

<400> SEQUENCE: 8
cgtgtataca gctgtgcggc cgcgtttgta ctgttcggct g                           41
```

```
<210> SEQ ID NO 9
<211> LENGTH: 41
<212> TYPE: DNA
<213> ORGANISM: Artificial Sequence
<220> FEATURE:
<223> OTHER INFORMATION: reverse primer used to clone the C-terminally
      truncated constructs of CBP

<400> SEQUENCE: 9
cgtgtataca gctgtgcggc cgctccattc atgacttgag c                           41
```

```
<210> SEQ ID NO 10
<211> LENGTH: 41
<212> TYPE: DNA
<213> ORGANISM: Artificial Sequence
<220> FEATURE:
<223> OTHER INFORMATION: reverse primer used to clone the C-terminally
      truncated constructs of CBP

<400> SEQUENCE: 10
cgtgtataca gctgtgcggc cgcgcgtttt tcagggtctg c                           41
```

```
<210> SEQ ID NO 11
<211> LENGTH: 41
<212> TYPE: DNA
<213> ORGANISM: Artificial Sequence
<220> FEATURE:
<223> OTHER INFORMATION: reverse primer used to clone the C-terminally
      truncated constructs of CBP

<400> SEQUENCE: 11
cgtgtataca gctgtgcggc cgcagctggt aaagctggct g                           41
```

```
<210> SEQ ID NO 12
<211> LENGTH: 41
<212> TYPE: DNA
```

```
<213> ORGANISM: Artificial Sequence
<220> FEATURE:
<223> OTHER INFORMATION: reverse primer used to clone the C-terminally
      truncated constructs of CBP

<400> SEQUENCE: 12
cgtgtataca gctgtgcggc cgcatgttgg agagagggca t                          41

<210> SEQ ID NO 13
<211> LENGTH: 41
<212> TYPE: DNA
<213> ORGANISM: Artificial Sequence
<220> FEATURE:
<223> OTHER INFORMATION: reverse primer used to clone the C-terminally
      truncated constructs of CBP

<400> SEQUENCE: 13
cgtgtataca gctgtgcggc cgcagaacct tgtaaatcct c                          41

<210> SEQ ID NO 14
<211> LENGTH: 41
<212> TYPE: DNA
<213> ORGANISM: Artificial Sequence
<220> FEATURE:
<223> OTHER INFORMATION: reverse primer used to clone the C-terminally
      truncated constructs of CBP

<400> SEQUENCE: 14
cgtgtataca gctgtgcggc cgcgctgtag taggctgcat c                          41

<210> SEQ ID NO 15
<211> LENGTH: 41
<212> TYPE: DNA
<213> ORGANISM: Artificial Sequence
<220> FEATURE:
<223> OTHER INFORMATION: reverse primer used to generate the
      N-terminally truncated constructs of CBP

<400> SEQUENCE: 15
gtatacagct gtgcggccgc caaaccctcc acaaactttt c                          41

<210> SEQ ID NO 16
<211> LENGTH: 40
<212> TYPE: DNA
<213> ORGANISM: Artificial Sequence
<220> FEATURE:
<223> OTHER INFORMATION: Forward primer for CBP-C8

<400> SEQUENCE: 16
gatatctgag ctcgtggatc cggaagctgg ggaggttttt                            40

<210> SEQ ID NO 17
<211> LENGTH: 40
<212> TYPE: DNA
<213> ORGANISM: Artificial Sequence
<220> FEATURE:
<223> OTHER INFORMATION: Forward primer for CBP-C9

<400> SEQUENCE: 17
gatatctgag ctcgtggatc cgaagaagat gctggacaag                            40

<210> SEQ ID NO 18
<211> LENGTH: 40
<212> TYPE: DNA
<213> ORGANISM: Artificial Sequence
<220> FEATURE:
<223> OTHER INFORMATION: Forward primer for CBP-C10
```

```
<400> SEQUENCE: 18
gatatctgag ctcgtggatc cgtccaaatg gtccactctg                                40

<210> SEQ ID NO 19
<211> LENGTH: 40
<212> TYPE: DNA
<213> ORGANISM: Artificial Sequence
<220> FEATURE:
<223> OTHER INFORMATION: Forward primer for CBP-C11

<400> SEQUENCE: 19
gatatctgag ctcgtggatc cgtctcctac ctcagcacca                                40

<210> SEQ ID NO 20
<211> LENGTH: 40
<212> TYPE: DNA
<213> ORGANISM: Artificial Sequence
<220> FEATURE:
<223> OTHER INFORMATION: Forward primer for CBP-C12

<400> SEQUENCE: 20
gatatctgag ctcgtggatc cgaacatcct taaatcaaac                                40

<210> SEQ ID NO 21
<211> LENGTH: 40
<212> TYPE: DNA
<213> ORGANISM: Artificial Sequence
<220> FEATURE:
<223> OTHER INFORMATION: Forward primer for CBP-C13

<400> SEQUENCE: 21
gatatctgag ctcgtggatc cgcagcagca acgcatgcaa                                40

<210> SEQ ID NO 22
<211> LENGTH: 79
<212> TYPE: DNA
<213> ORGANISM: Artificial Sequence
<220> FEATURE:
<223> OTHER INFORMATION: Forward primer used to generate CBP

<400> SEQUENCE: 22
atctgagctc gtggatccgg gaccgcccaa ccccaaacga gccaaactcc agccgaacag          60
tacaaacatg gccagctta                                                      79

<210> SEQ ID NO 23
<211> LENGTH: 39
<212> TYPE: DNA
<213> ORGANISM: Artificial Sequence
<220> FEATURE:
<223> OTHER INFORMATION: Forward primer for the C-terminal truncated
      p-300 constructs

<400> SEQUENCE: 23
gacggtaccg gttcgaagct tatggccgag aatgtggtg                                 39

<210> SEQ ID NO 24
<211> LENGTH: 41
<212> TYPE: DNA
<213> ORGANISM: Artificial Sequence
<220> FEATURE:
<223> OTHER INFORMATION: Reverse primer for the C-terminal truncated
      p-300 constructs

<400> SEQUENCE: 24
```
cgtgtataca gctgtgcggc cgccaaacct aatccaggac t            41

<210> SEQ ID NO 25
<211> LENGTH: 41
<212> TYPE: DNA
<213> ORGANISM: Artificial Sequence
<220> FEATURE:
<223> OTHER INFORMATION: Reverse primer for the C-terminal truncated
      p-300 constructs

<400> SEQUENCE: 25
cgtgtataca gctgtgcggc cgcgttgcca gcacttccca t            41

<210> SEQ ID NO 26
<211> LENGTH: 41
<212> TYPE: DNA
<213> ORGANISM: Artificial Sequence
<220> FEATURE:
<223> OTHER INFORMATION: Reverse primer for the C-terminal truncated
      p-300 constructs

<400> SEQUENCE: 26
cgtgtataca gctgtgcggc cgcggcctgt tcccggcgct g            41

<210> SEQ ID NO 27
<211> LENGTH: 102
<212> TYPE: DNA
<213> ORGANISM: Artificial Sequence
<220> FEATURE:
<223> OTHER INFORMATION: Four tandem TCF4 binding sites used to generate
      the beta-catenin/TCF reporter plasmid

<400> SEQUENCE: 27
ccaacctttg atcttacccc ctttgatctt acccccttttg atcaggaatt cggttggaaa        60
ctagaatggg ggaaactaga atgggggaaa ctagtcctta ag                          102

<210> SEQ ID NO 28
<211> LENGTH: 19
<212> TYPE: DNA
<213> ORGANISM: Artificial Sequence
<220> FEATURE:
<223> OTHER INFORMATION: Forward primer used for PCR of c-myc promoters

<400> SEQUENCE: 28
tggtaggcgc gcgtagtta            19

<210> SEQ ID NO 29
<211> LENGTH: 19
<212> TYPE: DNA
<213> ORGANISM: Artificial Sequence
<220> FEATURE:
<223> OTHER INFORMATION: Reverse primer used for PCR of c-myc promoters

<400> SEQUENCE: 29
gggcggagat tagcgagag            19

<210> SEQ ID NO 30
<211> LENGTH: 19
<212> TYPE: DNA
<213> ORGANISM: Artificial Sequence
<220> FEATURE:
<223> OTHER INFORMATION: Forward primer used for PCR of cyclin D1
      promoters

<400> SEQUENCE: 30
tgcttaacaa cagtaacgt            19

<210> SEQ ID NO 31
<211> LENGTH: 19
<212> TYPE: DNA
<213> ORGANISM: Artificial Sequence
<220> FEATURE:
<223> OTHER INFORMATION: Reverse primer used for PCR of cyclin D1
      promoters

<400> SEQUENCE: 31
ggggctcttc ctgggcagc                                        19

<210> SEQ ID NO 32
<211> LENGTH: 17
<212> TYPE: DNA
<213> ORGANISM: Artificial Sequence
<220> FEATURE:
<223> OTHER INFORMATION: cyclin-D1 forward primer

<400> SEQUENCE: 32
agatcgaagc cctgctg                                          17

<210> SEQ ID NO 33
<211> LENGTH: 18
<212> TYPE: DNA
<213> ORGANISM: Artificial Sequence
<220> FEATURE:
<223> OTHER INFORMATION: cyclin-D1 reverse primer

<400> SEQUENCE: 33 aggggggaaag agcaaagg                                        18

<210> SEQ ID NO 34
<211> LENGTH: 20
<212> TYPE: DNA
<213> ORGANISM: Artificial Sequence
<220> FEATURE:
<223> OTHER INFORMATION: axin2 forward primer

<400> SEQUENCE: 34
gtgtgaggtc cacggaaact                                       20

<210> SEQ ID NO 35
<211> LENGTH: 20
<212> TYPE: DNA
<213> ORGANISM: Artificial Sequence
<220> FEATURE:
<223> OTHER INFORMATION: axin2 reverse primer

<400> SEQUENCE: 35
ctcgggaaat gaggtagaga                                       20

<210> SEQ ID NO 36
<211> LENGTH: 25
<212> TYPE: DNA
<213> ORGANISM: Artificial Sequence
<220> FEATURE:
<223> OTHER INFORMATION: hnkd forward primer

<400> SEQUENCE: 36
ctggctgctg ctaccaccat tgcgt                                 25

<210> SEQ ID NO 37
<211> LENGTH: 20
<212> TYPE: DNA
<213> ORGANISM: Artificial Sequence

```
<220> FEATURE:
<223> OTHER INFORMATION: hnkd reverse primer

<400> SEQUENCE: 37
ccaggcccaa attgggacgt                                                    20

<210> SEQ ID NO 38
<211> LENGTH: 20
<212> TYPE: DNA
<213> ORGANISM: Artificial Sequence
<220> FEATURE:
<223> OTHER INFORMATION: c-myc forward primer

<400> SEQUENCE: 38
gaagaaattc gagctgctgc                                                    20

<210> SEQ ID NO 39
<211> LENGTH: 21
<212> TYPE: DNA
<213> ORGANISM: Artificial Sequence
<220> FEATURE:
<223> OTHER INFORMATION: c-myc reverse primer

<400> SEQUENCE: 39
cacatacagt cctggatgat g                                                  21

<210> SEQ ID NO 40
<211> LENGTH: 20
<212> TYPE: DNA
<213> ORGANISM: Artificial Sequence
<220> FEATURE:
<223> OTHER INFORMATION: c-jun forward primer

<400> SEQUENCE: 40
agatgcccgg cgagacaccg                                                    20

<210> SEQ ID NO 41
<211> LENGTH: 19
<212> TYPE: DNA
<213> ORGANISM: Artificial Sequence
<220> FEATURE:
<223> OTHER INFORMATION: c-jun reverse primer

<400> SEQUENCE: 41
agcccccgac ggtctctttt                                                    19

<210> SEQ ID NO 42
<211> LENGTH: 26
<212> TYPE: DNA
<213> ORGANISM: Artificial Sequence
<220> FEATURE:
<223> OTHER INFORMATION: fra-1 forward  primer

<400> SEQUENCE: 42
accccggcca ggagtcatcc gggccc                                             26

<210> SEQ ID NO 43
<211> LENGTH: 26
<212> TYPE: DNA
<213> ORGANISM: Artificial Sequence
<220> FEATURE:
<223> OTHER INFORMATION: fra-1 reverse  primer

<400> SEQUENCE: 43
aggcgcctca caaagcgagg agggtt                                             26
```

```
<210> SEQ ID NO 44
<211> LENGTH: 32
<212> TYPE: DNA
<213> ORGANISM: Artificial Sequence
<220> FEATURE:
<223> OTHER INFORMATION: beta-actin forward primer

<400> SEQUENCE: 44
atctggcacc acaccttcta caatgagctg cg                                    32

<210> SEQ ID NO 45
<211> LENGTH: 32
<212> TYPE: DNA
<213> ORGANISM: Artificial Sequence
<220> FEATURE:
<223> OTHER INFORMATION: beta-actin reverse primer

<400> SEQUENCE: 45
cgtcatactc ctccttgcyg atccacatct gc                                    32

<210> SEQ ID NO 46
<211> LENGTH: 5
<212> TYPE: PRT
<213> ORGANISM: Artificial Sequence
<220> FEATURE:
<223> OTHER INFORMATION: consensus RXR/RAR binding site
<220> FEATURE:
<221> NAME/KEY: VARIANT
<222> LOCATION: 2, 3
<223> OTHER INFORMATION: Xaa = Any Amino Acid

<400> SEQUENCE: 46

Leu Xaa Xaa Leu Leu
  1               5

<210> SEQ ID NO 47
<211> LENGTH: 15
<212> TYPE: PRT
<213> ORGANISM: Homo sapiens

<400> SEQUENCE: 47

Asn Asp Glu Leu Ile Arg Phe Lys Asp Glu Gly Glu Gln Glu Glu
  1               5                  10                  15

<210> SEQ ID NO 48
<211> LENGTH: 21
<212> TYPE: PRT
<213> ORGANISM: Homo sapiens

<400> SEQUENCE: 48

Tyr Asp Ser Leu Leu Val Phe Asp Tyr Glu Gly Ser Gly Ser Ala Ala
  1               5                  10                  15

Ser Leu Ser Ser Leu
             20

<210> SEQ ID NO 49
<211> LENGTH: 20
<212> TYPE: PRT
<213> ORGANISM: Homo sapiens

<400> SEQUENCE: 49

Ala Asp Thr Leu Leu His Phe Ala Thr Glu Ser Ser Cys Ser Ser Ser
  1               5                  10                  15

Leu Ser Ala Leu
             20
```

```
<210> SEQ ID NO 50
<211> LENGTH: 15
<212> TYPE: PRT
<213> ORGANISM: Homo sapiens

<400> SEQUENCE: 50

Leu Asp Thr Pro Ile Asn Tyr Ser Leu Lys Tyr Ser Asp Glu Gln
 1               5                  10                  15

<210> SEQ ID NO 51
<211> LENGTH: 16
<212> TYPE: PRT
<213> ORGANISM: Homo sapiens

<400> SEQUENCE: 51

Glu Asp Thr Pro Ile Cys Phe Ser Arg Cys Ser Ser Leu Ser Ser Leu
 1               5                  10                  15

<210> SEQ ID NO 52
<211> LENGTH: 15
<212> TYPE: PRT
<213> ORGANISM: Homo sapiens

<400> SEQUENCE: 52

Glu Asp Val Val Met Ala Phe Ser Arg Ser Gly Thr Glu Asp Arg
 1               5                  10                  15

<210> SEQ ID NO 53
<211> LENGTH: 24
<212> TYPE: PRT
<213> ORGANISM: Homo sapiens

<400> SEQUENCE: 53

Pro Asp Glu Leu Ile Pro Asn Gly Gly Glu Leu Gly Leu Leu Asn Ser
 1               5                  10                  15

Ser Gly Ser Ser Ala Ser Ser Pro
                 20

<210> SEQ ID NO 54
<211> LENGTH: 23
<212> TYPE: PRT
<213> ORGANISM: Mus musculus

<400> SEQUENCE: 54

Pro Asp Glu Leu Ile Pro Asn Gly Glu Leu Ser Leu Leu Asn Ser Ser
 1               5                  10                  15

Gly Ser Ser Ala Ser Ser Pro
                 20

<210> SEQ ID NO 55
<211> LENGTH: 23
<212> TYPE: PRT
<213> ORGANISM: Homo sapiens

<400> SEQUENCE: 55

Pro Asp Glu Leu Ile Asn Ser Thr Glu Leu Gly Leu Thr Asn Ser Ser
 1               5                  10                  15

Gly Ser Gly Gly Pro Gly Gln
                 20
```

MODULATION OF β-CATENIN/TCF-ACTIVATED TRANSCRIPTION

CROSS-REFERENCE TO RELATED APPLICATION

This application claims the benefit of U.S. Provisional Patent Application No. 60/498,451 filed Aug. 28, 2003, where this provisional application is incorporated herein by reference in its entirety.

BACKGROUND OF THE INVENTION

1. Field of the Invention

The present invention relates to compounds and methods for modulating transcription activated by β-catenin/TCF, for example, the selective inhibition of genes targeted by the Wnt/β-catenin pathway.

2. Description of the Related Art

The Wnt/β-catenin pathway initiates a signaling cascade critical in both normal development and the initiation and progression of cancer (Wodarz et al., "Mechanisms of Wnt signaling in development," *Annu. Rev. Cell Dev. Biol.* 14:59-88 (1998); Morin, P. J., "Beta-catenin signaling and cancer," *Bioessays* 21:1021-30 (1999); Moon et al., "The promise and perils of Wnt signaling through beta-catenin," *Science* 296: 1644-46 (2002); Oving et al., "Molecular causes of colon cancer," *Eur. J. Clin. Invest.* 32:448-57 (2002)). The hallmark of this pathway is that it activates the transcriptional role of the multifunctional protein β-catenin. In normal cells, the majority of β-catenin is found at the cell membrane bound to cadherin where it plays an important role in cell adhesion. Another pool of β-catenin is found in the cytoplasm and nucleus where it regulates transcription (Gottardi et al., "Adhesion signaling: how beta-catenin interacts with its partners," *Curr. Biol.* 11:R792-4 (2001)). In its diverse roles as a mediator of cell adhesion at the plasma membrane, and as a transcriptional activator, β-catenin interacts with a host of proteins, the majority of which, despite a lack of significant sequence homology, compete for the same armadillo-repeats of β-catenin. The crystal structure along with mutational studies has mapped the β-catenin binding sites of several proteins to various armadillo repeats (Gottardi et al., "Adhesion signaling: how beta-catenin interacts with its partners," *Curr. Biol.* 11:R792-4 (2001); Huber et al., "The structure of the beta-catenin/E-cadherin complex and the molecular basis of diverse ligand recognition by beta-catenin," *Cell* 105:391-402 (2001)).

The cytoplasmic pool of β-catenin is regulated via phosphorylation by the "destruction complex" that includes glycogen synthase kinase-3β (GSK-3β), casein kinase-1α (CK-1α), the scaffold protein, Axin, and the tumor suppressor, adenomatous polyposis coli (APC), among others (Behrens J., "Control of beta-catenin signaling in tumor development," *Ann. N.Y. Acad. Sci.* 910:21-33 (2000); discussion 33-5). In the absence of Wnt signaling, phosphorylation marks the cytoplasmic β-catenin for Skp1-Cullin-F box (SCF)-directed ubiquitination and proteosomal degradation. Activation of the Wnt pathway inactivates the function of GSK-3β, preventing β-catenin phosphorylation, thereby allowing β-catenin to accumulate in the cytoplasm and subsequently translocate to the nucleus where it forms a transcriptionally active complex and drives the expression of its target genes. A key step in the activation of target genes is the formation of a complex between β-catenin and members of the T-cell factor (TCF)/lymphoid enhancer factor (LEF-1) family of transcription factors (Brantjes et al., "TCF: Lady Justice casting the final verdict on the outcome of Wnt signaling," *Biol. Chem.* 383:255-61 (2002)). To generate a transcriptionally active complex, β-catenin recruits the transcriptional coactivators, CREB-binding protein (CBP) or its closely related homolog p300 (Hecht et al., "The p300/CBP acetyltransferases function as transcriptional coactivators of beta-catenin in vertebrates," *EMBO J.* 19:1839-50 (2000); Takemaru et al., "The transcriptional coactivator CBP interacts with beta-catenin to activate gene expression," *J. Cell Biol.* 149:249-54 (2000)) as well as other components of the basal transcription machinery.

The precise mechanism by which the β-catenin/TCF complex activates transcription of Wnt responsive genes is not clear, but domains of β-catenin involved in transcriptional activation have been mapped to the NH2- and COOH-termini (Staal et al., "Wnt signals are transmitted through N-terminally dephosphorylated beta-catenin," *EMBO* 3:63-68 (2002)). The COOH-terminal region of β-catenin consists of approximately 100 amino acids and it has been shown to interact with the TATA binding protein (TBP) (Hecht et al., "Functional characterization of multiple transactivating elements in beta-catenin, some of which interact with the TATA-binding protein in vitro," *J. Biol. Chem.* 274:18017-25 (1999)). When fused to LEF-1, the COOH-terminus is sufficient to promote transactivation (Vleminckx et al., "The C-terminal transactivation domain of beta-catenin is necessary and sufficient for signaling by the LEF-1/beta-catenin complex in *Xenopus laevis,*" *Mech. Dev.* 81:65-74 (1999)). The NH2-terminal portion of β-catenin consists of approximately 130 amino acids containing the GSK-3β phosphorylation sites required for proteosomal degradation.

The Wnt/β-catenin pathway normally regulates expression of a range of genes involved in promoting proliferation and differentiation. However, in >85% of colon cancers one of the components of the destruction complex, APC, and/or β-catenin itself is mutated, leading to an increase in nuclear β-catenin and constitutive activation of target genes (Fearnhead et al., "Genetics of colorectal cancer: hereditary aspects and overview of colorectal tumorigenesis," *Br. Med. Bull.* 64:27-43 (2002)). Many of these genes, including cyclin D1 (Shtutman et al., "The cyclin D1 gene is a target of the beta-catenin/LEF-1 pathway," *Proc. Natl. Acad. Sci. USA* 96:5522-27 (1999); Tetsu et al., "Beta-catenin regulates expression of cyclin D1 in colon carcinoma cells," *Nature* 398:422-26 (1999)) and c-myc (He et al., "Identification of c-MYC as a target of the APC pathway," *Science* 281:1509-12 (1998)) which play critical roles in cell growth, proliferation, and differentiation, together with genes necessary for invasive growth like matrilysin (Crawford et al., "The metalloproteinase matrilysin is a target of beta-catenin transactivation in intestinal tumors," *Oncogene* 18:2883-91 (1999)), fibronectin (Gradl et al., "The Wnt/Wg signal transducer beta-catenin controls fibronectin expression," *Mol. Cell. Biol.* 19:5576-87 (1999)), CD44 (Wielenga et al., "Expression of CD44 in Apc and Tcf mutant mice implies regulation by the WNT pathway," *Am. J. Pathol.* 154:515-23 (1999)), and μPAR (Mann et al., "Target genes of beta-catenin-T cell-factor/lymphoid-enhancer-factor signaling in human colorectal carcinomas," *Proc. Natl. Acad. Sci. USA* 96:1603-08 (1999)) are inappropriately activated.

Given that the majority of colorectal cancers involve activation of the β-catenin signaling pathway, and given the fact that multiple mutations lead to this activation, there is a clear need for drugs that attenuate the nuclear functions of β-catenin. The present invention provides agents which antagonize β-catenin/TCF-mediated transcription, and provides further related advantages as described in detail below.

BRIEF SUMMARY OF THE INVENTION

In brief, the present invention provides agents that antagonize β-catenin/TCF-mediated transcription, and methods for their use. In one aspect, the invention provides methods whereby a subset of β-catenin/TCF-responsive genes are specifically down-regulated, while in a related aspect the invention provides compounds useful in the method. In another aspect, the invention provides methods whereby the binding between CBP and β-catenin is disrupted but the binding between the structurally related co-activator p300 and β-catenin is not disrupted, while in a related aspect the invention provides compounds useful in the method. In another aspect, the present invention provides methods whereby genes that are promoted by CBP but not p300 are selectively activated, while in a related aspect the invention provides compounds useful in the method. In addition, the present invention provides methods whereby genes that are promoted by p300 but not CBP are selectively activated, while in a related aspect the invention provides compounds useful in this method. In another aspect, the present invention provides method whereby carcinoma cells are treated with a chemical agent in order to arrest development at the $G_1$-phase of the cell cycle, where prolonged treatment with the chemical agent induces apoptosis which is not detected in normal colonocytes. The carcinoma cells may be, for example, colon, breast, prostrate, etc.

For example, in one aspect the present invention provides a method for modulating β-catenin-induced gene expression. The method comprises contacting a composition with an agent, where the composition comprises β-catenin, CBP and p300, and the β-catenin has a likelihood of binding to CBP versus p300. The agent is present in the composition in an amount effective to change the likelihood of β-catenin binding to CBP versus p300. In other words, in the absence of the agent, β-catenin binds to CBP and p300 to a different extent than is observed when the agent is present. For example, depending on its chemical structure, the agent may do the following: increase the binding of CBP to β-catenin, while optionally decreasing the binding of p300 to β-catenin; or increase the binding of p300 to β-catenin, while optionally decreasing the binding of CBP to β-catenin. The method may be performed in vivo or ex vivo. In one aspect, the method is performed ex vivo and the composition comprises a stem cell. In another aspect the method is performed in vivo and the composition is within a mammal. The method of the invention may be used to treat various medical conditions. For instance, in various aspects of the invention: the mammal may suffer from cancer, and the amount is effective to treat the cancer; the composition is within a cell, and the agent increases the likelihood that the cell will differentiate; the composition is within a cell, and the agent increases the likelihood that the cell will proliferate.

In another aspect, the present invention provides a composition comprising β-catenin, CBP, p300 and an agent. The β-catenin has a likelihood of binding to CBP versus p300, and the agent is present in the composition in an amount effective to change the likelihood of β-catenin binding to CBP versus p300. In other words, in the absence of the agent, β-catenin binds to CBP and p300 to a different extent than is observed when the agent is present. For example, depending on its chemical structure, the agent may do the following: increase the binding of CBP to β-catenin, while optionally decreasing the binding of p300 to β-catenin; or increase the binding of p300 to β-catenin, while optionally decreasing the binding of CBP to β-catenin. The composition may be in vivo or ex vivo. In one aspect, the composition is ex vivo and the composition further comprises a stem cell. In another aspect the composition is in vivo and the composition is within a mammal, e.g., a mouse.

In another aspect, the present invention provides a method for modulating the activity of the Wnt pathway, comprising: (a) contacting the components of a Wnt pathway with a compound that activates the Wnt pathway to provide activated Wnt pathway; and (b) contacting the activated Wnt pathway with a chemical agent that completely or substantially interferes with binding between p300 and catenin but causes little or no interference with binding between CBP and catenin. Optionally, the Wnt pathway is within a cell. Optionally, the method is performed ex vivo. Optionally, the compound that activates the Wnt pathway is selected from LiCl and GSK inhibitor.

In another aspect, the present invention provides a method for modulating cell proliferation, comprising: (a) providing a cell population under conditions where a proportion of the population will proliferate and a proportion of the population will differentiate; and (b) adding a chemical agent to the population, where the agent causes an increase in the proportion of the cells that proliferate relative to the proportion of the cells that differentiate. In various optional embodiments of the method: the compound interferes with binding between p300 and catenin; the method further includes adding an agent to the population that activates a Wnt pathway; the cell population is a population of stem cells; the method is performed ex vivo; the method further includes adding an agent that causes differentiation of the cell population where, e.g., the cells in the population differentiate to form blood cells or the cells in the population differentiate to form neuron cells.

In another aspect, the present invention provides a method for maintaining a stem cell in an undifferentiated state, comprising contacting the stem cell with an agent that inhibits cell differentiation or promotes cell proliferation in an amount effective to maintain the stem cell in an undifferentiated state. In certain embodiments, the agent used in the method selectively inhibits β-catnin/p300 interaction relative to β-catnin/CBP interaction.

Briefly, in other aspects, the present invention provides:

a method for selectively inhibiting β-catenin/CBP interaction relative to β-catenin/p300 interaction, the method comprising administering a compound to a composition, where the composition comprises β-catenin, CBP and p300, and the compound selectively inhibits β-catenin/CBP interaction relative to β-catenin/p300 interacts;

a method for selectively inhibiting β-catenin/p300 interaction relative to β-catenin/CBP interaction, the method comprising administering a compound to a composition, where the composition comprises β-catenin, CBP and p300, and the compound selectively inhibits β-catenin/p300 interaction relative to β-catenin/CBP interacts;

a method for enhancing translocation of β-catenin from the nucleus to the cytosol, the method comprising administering a compound to a cell, where the cell comprises a nucleus and a cytosol, and the nucleus comprises β-catenin, and the compound causes translocation of β-catenin from the nucleus to the cytosol;

a method for selectively inhibiting expression of genes targeted by the WNT/β-catenin pathway, the method comprising administering a compound to a composition, the composition comprising genes targeted by the WNT/β-catenin pathway, the compound causing a change in expression of the genes targeted by the WNT/β-catenin pathway.

In the methods and compositions of the present invention, the chemical agent is optionally selected from compounds of the formula (I):

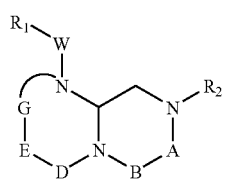

wherein A is —(CHR$_3$)— or —(C=O)—, B is —(CHR$_4$)— or —(C=O)—, D is —(CHR$_5$)— or —(C=O)—, E is -(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1; and R$_1$, R$_2$, R$_3$, R$_4$, R$_5$, R$_6$, R$_7$, R$_8$ and R$_9$ are the same or different and are each independently selected from an amino acid side chain moiety, a derivative of an amino acid side chain moiety, or the remainder of the molecule, and stereoisomers thereof.

In certain embodiments, R$_1$, R$_2$, R$_3$, R$_4$, R$_5$, R$_6$, R$_7$, R$_8$ and R$_9$ of formula (I) are independently selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, phenyl, substituted phenyl(where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl, (where the substituents are independently selected from one or more of amino amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrmidine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy or nitro, carboxy, cyano, sulfuryl or hydroxyl), triazin-2-yl-C$_{1-4}$alkyl, substituted triazin-2-yl-C$_{1-4}$alkyl (where the triazine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazoC$_{1-4}$alkyl, substituted imidazol C$_{1-4}$alkyl (where the imidazole sustituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazolinylC$_{1-4}$alkyl, N-amidinopiperazinyl-N-C$_{0-4}$alkyl, hydroxyC$_{2-5}$alkyl, C$_{1-5}$alkylamino C$_{2-5}$alkyl, hydroxyC$_{2-5}$alkyl, C$_{1-5}$alkylaminoC$_{2-5}$alkyl, C$_{1-5}$dialkylaminoC$_{2-5}$alkyl, N-amidinopiperidinylC$_{1-4}$alkyl and 4-aminocyclohexylC$_{0-2}$alkyl.

In certain embodiments, A is —(CHR$_3$)—, B is —(C=O)—, D is —(CHR$_5$)—, E is —(C=O)—, G is —(XR$_7$)$_n$—, and the compound has the following general formula (II):

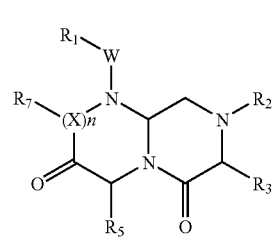

wherein R$_1$, R$_2$, R$_3$, R$_5$, R$_7$, W, X and n are as defined as in formula (I).

In certain embodiments, A is —(C=O)—, B is —(CHR$_4$)—, D is —(C=O)—, E is -(ZR$_6$)—, G is —(C=O)—(XR$_9$)—, and the compound has the following general formula (III):

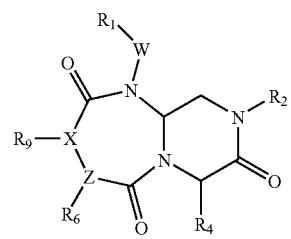

wherein R$_1$, R$_2$, R$_4$, R$_6$, R$_9$, W and X are as defined in formula (I), Z is nitrogen or CH (when Z is CH, then X is nitrogen).

In certain embodiments, A is —(C=O)—, B is —(CHR$_4$)—, D is —(C=O)—, E is -(ZR$_6$)—, G is (XR$_7$)$_n$—, and the compound has the following general formula (IV):

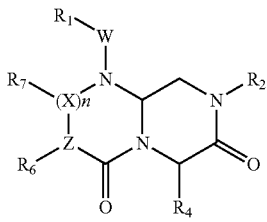

(IV)

wherein $R_1$, $R_2$, $R_4$, $R_6$, $R_7$, W, X and n are as defined in formula (I), and Z is nitrogen or CH, with the proviso that when Z is nitrogen, then n is zero, and when Z is CH, then X is nitrogen and n is not zero.

In certain embodiments, the compound has the following general formula (VI):

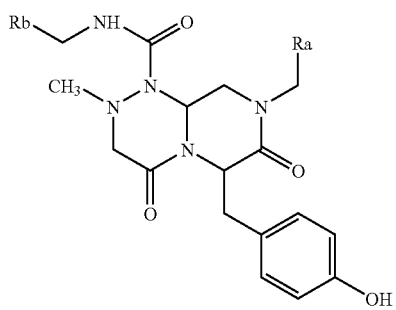

(VI)

wherein, $R_a$ is a bicyclic aryl group having 8 to 11 ring members, which may have 1 to 3 heteroatoms selected from nitrogen, oxygen or sulfur, and $R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy group. Optionally, $R_a$ is naphthyl, quinolinyl or isoquinolinyl group, and $R_b$ is phenyl, pyridyl or piperidyl, all of which may be substituted with one or more substituents selected from a group consisting of halide, hydroxy, cyano, lower alkyl, and lower alkoxy group. In certain embodiments, $R_a$ is naphthyl, and $R_b$ is phenyl, which may be substituted with one or more substituents selected from a group consisting of halide, hydroxy, cyano, lower alkyl, and lower alkoxy group.

In certain embodiments, the compound is selected from COMPOUNDS 1, 3, 4, and 5.

In other aspects, the present invention provides screening methods, i.e., methods whereby biologically active compounds may be identified and/or their efficacy evaluated. For instance, the present invention provides a method for identifying a small molecule inhibitor of the β-catenin:CBP interaction, comprising the steps of: (a) contacting a putative beta-catenin:CBP small molecule inhibitor with a moiety comprising CBP 1-111; (b) contacting the admixture of step (a) with a moiety comprising β-catenin; (c) determining, by assay means, if said molecule of step (a) inhibits the binding of the moiety comprising β-catenin of step (b) with the moiety comprising CBP 1-111 of step (a); and (d) identifying, upon determination that said small molecule of step (a) inhibits the binding of said moiety comprising CBP 1-111 with the moiety comprising β-catenin, the small molecule of step (a) as an inhibitor of beta-catenin:CBP interaction.

Optionally, the above method may further comprise the steps of: (e) contacting the identified small molecule inhibitor of β-catenin:CBP interaction of step (d) with an admixture comprising (1) a moiety comprising p300 1-111 and (2) β-catenin; (f) determining, by assay means, if said molecule of step (e) does not inhibit the binding of said moiety comprising p300 1-111 with β-catenin; and (g) confirming, upon determination that said small molecule of step (e) does not inhibit the binding of said moiety comprising p300 1-111 with said β-catenin, that said small molecule is a selective inhibitor of β-catenin:CBP interaction.

The present invention also provides a method for identifying a small molecule inhibitor of the β-catenin:CBP interaction comprising the steps of: (a) contacting a putative β-catenin:CBP small molecule inhibitor with a moiety comprising β-catenin; (b) contacting the admixture of step (a) with a moiety comprising CBP 1-111; (c) determining, by assay means, if said molecule of step (a) inhibits the binding of the moiety comprising CBP 1-111 of step (b) with the moiety comprising β-catenin of step (a); (d) identifying, upon determination that said small molecule of step (a) inhibits the binding of said moiety comprising β-catenin with the moiety comprising CBP 1-111, the small molecule of step (a) as an inhibitor of β-catenin:CBP interaction.

Optionally, the above method may further comprise the steps of: (e) contacting the identified small molecule inhibitor of β-catenin:CBP interaction of step (d) with an admixture comprising (1) a moiety comprising p300 1-111 and (2) β-catenin; (f) determining, by assay means, if said molecule of step (e) does not inhibit the binding of said moiety comprising p300 1-111 with β-catenin; and (g) confirming, upon determination that said small molecule of step (e) does not inhibit the binding of said moiety comprising p300 1-111 with said β-catenin, that said small molecule is a selective inhibitor of β-catenin:CBP interaction.

The present invention also provides a method for identifying a small molecule inhibitor of the β-catenin:CBP interaction comprising the steps of: (a) contacting a putative beta-catenin:CBP small molecule inhibitor with a moiety, said moiety comprising (1) β-catenin associated with CBP 1-111; (b) determining, by assay means, if said molecule of step (a) disassociates CBP 1-111 from β-catenin; and (c) identifying, upon determination that said small molecule of step (a) disassociates the binding of β-catenin from CBP 1-110, the small molecule of step (a) as an inhibitor of β-catenin:CBP interaction.

Optionally, the above method may further comprise the steps of: (d) contacting the identified small molecule inhibitor of β-catenin:CBP interaction of step (c) with an admixture comprising (1) a moiety comprising p300 1-111 and (2) β-catenin; (e) determining, by assay means, if said molecule of step (d) does not inhibit the binding of said moiety comprising p300 1-111 with β-catenin; and (f) confirming, upon determination that said small molecule of step (d) does not inhibit the binding of said moiety comprising p300 1-111 with said β-catenin, that said small molecule is a selective inhibitor of β-catenin:CBP interaction.

The present invention also provides a method for identifying a small molecule inhibitor of the β-catenin:p300 interaction comprising the steps of: (a) contacting a putative beta-catenin:CBP small molecule inhibitor with a moiety comprising p300 1-111; (b) contacting the admixture of step (a) with a moiety comprising β-catenin; (c) determining, by assay means, if said molecule of step (a) inhibits the binding of the moiety comprising β-catenin of step (b) with the moiety comprising p300 1-111 of step (a); and (d) identifying, upon determination that said small molecule of step (a) inhibits the binding of said moiety comprising p300 1-111 with the moiety comprising β-catenin, the small molecule of step (a) as an inhibitor of beta-catenin:p300 interaction.

Optionally, the above method may further comprise the steps of: (e) contacting the identified small molecule inhibitor of β-catenin:p300 interaction of step (d) with an admixture comprising (1) a moiety comprising CBP 1-111 and (2) β-catenin; (f) determining, by assay means, if said molecule of step (e) does not inhibit the binding of said moiety comprising CBP 1-111 with β-catenin; and (g) confirming, upon determination that said small molecule of step (e) does not inhibit the binding of said moiety comprising CBP 1-111 with said β-catenin, that said small molecule is a selective inhibitor of β-catenin:p300 interaction.

The present invention also provides a method for identifying a small molecule inhibitor of the β-catenin:p300 interaction comprising the steps of: (a) contacting a putative β-catenin:p300 small molecule inhibitor with a moiety comprising β-catenin; (b) contacting the admixture of step (a) with a moiety comprising p300 1-111; (c) determining, by assay means, if said molecule of step (a) inhibits the binding of the moiety comprising p300 1-111 of step (b) with the moiety comprising β-catenin of step (a); (d) identifying, upon determination that said small molecule of step (a) inhibits the binding of said moiety comprising β-catenin with the moiety comprising p300 1-111, the small molecule of step (a) as an inhibitor of β-catenin:p300 interaction.

Optionally, the above method may further comprise the steps of: (e) contacting the identified small molecule inhibitor of β-catenin:p300 interaction of step (d) with an admixture comprising (1) a moiety comprising CBP 1-111 and (2) β-catenin; (f) determining, by assay means, if said molecule of step (e) does not inhibit the binding of said moiety comprising CBP 1-111 with β-catenin; and (g) confirming, upon determination that said small molecule of step (e) does not inhibit the binding of said moiety comprising CBP 1-111 with said β-catenin, that said small molecule is a selective inhibitor of β-catenin:p300 interaction.

The present invention also provides a method for identifying a small molecule inhibitor of the β-catenin:p300 interaction comprising the steps of: (a) contacting a putative beta-catenin:p300 small molecule inhibitor with a moiety, said moiety comprising (1) β-catenin associated with p300 1-111; (b) determining, by assay means, if said molecule of step (a) disassociates p300 1-111 from β-catenin; and (c) identifying, upon determination that said small molecule of step (a) disassociates the binding of β-catenin from p300 1-111, the small molecule of step (a) as an inhibitor of β-catenin:p300 interaction.

Optionally, the above method may further comprise the steps of: (d) contacting the identified small molecule inhibitor of β-catenin:p300 interaction of step (c) with an admixture comprising (1) a moiety comprising CBP 1-111 and (2) β-catenin; (e) determining, by assay means, if said molecule of step (d) does not inhibit the binding of said moiety comprising CBP 1-111 with β-catenin; and (f) confirming, upon determination that said small molecule of step (c) does not inhibit the binding of said moiety comprising CBP 1-111 with said β-catenin, that said small molecule is a selective inhibitor of β-catenin:p300 interaction.

In other aspects, the present invention provides nucleic acid and peptide sequences, where these sequences are useful as, e.g., therapeutics, or in, e.g., screening methods. Thus, in various exemplary aspects, the present invention provides:

a substantially purified and isolated sequence of nucleic acids comprising SEQ ID NO:1 or a sequence having at least 80% identity to SEQ ID NO:1, with the proviso that said sequence not encode for the CBP protein;

a substantially purified and isolated sequence of nucleic acids comprising a fragment of SEQ ID NO:1 or a sequence having at least 80% identity to said fragment, with the proviso that said sequence not encode for the CBP protein;

a substantially purified and isolated peptide comprising SEQ ID NO:2 or a peptide having at least 80% identity to SEQ ID NO:2, with the proviso that said peptide is not the CBP protein.

a substantially purified and isolated peptide comprising a fragment of SEQ ID NO:2 or a sequence having at least 80% identity to said fragment, with the proviso that peptide is not the CBP protein;

a substantially purified and isolated sequence of nucleic acids consisting essentially of SEQ ID NO:1 or a sequence having at least 80% identity to SEQ ID NO:1, with the proviso that said sequence not encode for the CBP protein;

a substantially purified and isolated sequence of nucleic acids consisting essentially of a fragment of SEQ ID NO:1 or a sequence having at least 80% identity to said fragment, with the proviso that said sequence not encode for the CBP protein;

a substantially purified and isolated peptide consisting essentially of SEQ ID NO:2 or a peptide having at least 80% identity to SEQ ID NO:2, with the proviso that said peptide is not the CBP protein;

a substantially purified and isolated peptide consisting essentially of a fragment of SEQ ID NO:2 or a sequence having at least 80% identity to said fragment, with the proviso that said peptide is not the CBP protein;

a substantially purified and isolated sequence of nucleic acids consisting of SEQ ID NO:1 or a sequence having at least 80% identity to SEQ ID NO:1, with the proviso that said sequence not encode for the CBP protein;

a substantially purified and isolated sequence of nucleic acids consisting of a fragment of SEQ ID NO:1 or a sequence having at least 80% identity to said fragment, with the proviso that said sequence not encode for the CBP protein;

a substantially purified and isolated peptide consisting of SEQ ID NO:2 or a peptide having at least 80% identity to SEQ ID NO:2, with the proviso that said peptide is not the CBP protein;

a substantially purified and isolated peptide consisting of a fragment of SEQ ID NO:2 or a sequence having at least 80% identity to said fragment, with the proviso that said peptide is not the CBP protein;

a substantially purified and isolated sequence of nucleic acids comprising SEQ ID NO:3 or a sequence having at least 80% identity to SEQ ID NO:1, with the proviso that said sequence not encode for the p300 protein;

a substantially purified and isolated sequence of nucleic acids comprising a fragment of SEQ ID NO:3 or a sequence having at least 80% identity to said fragment, with the proviso that said sequence not encode for the p300 protein;

a substantially purified and isolated peptide comprising SEQ ID NO:4 or a peptide having at least 80% identity to SEQ ID NO:4, with the proviso that said peptide is not the p300 protein;

a substantially purified and isolated peptide comprising a fragment of SEQ ID NO:4 or a sequence having at least 80% identity to said fragment, with the proviso that peptide is not the p300 protein;

a substantially purified and isolated sequence of nucleic acids consisting essentially of SEQ ID NO:3 or a sequence having at least 80% identity to SEQ ID NO:3, with the proviso that said sequence not encode for the p300 protein;

a substantially purified and isolated sequence of nucleic acids consisting essentially of a fragment of SEQ ID NO:3 or a sequence having at least 80% identity to said fragment, with the proviso that said sequence not encode for the p300 protein;

a substantially purified and isolated peptide consisting essentially of SEQ ID NO:4 or a peptide having at least 80% identity to SEQ ID NO:2, with the proviso that said peptide is not the p300 protein;

a substantially purified and isolated peptide consisting essentially of a fragment of SEQ ID NO:4 or a sequence having at least 80% identity to said fragment, with the proviso that said peptide is not the p300 protein;

a substantially purified and isolated sequence of nucleic acids consisting of SEQ ID NO:3 or a sequence having at least 80% identity to SEQ ID NO:3, with the proviso that said sequence not encode for the p300 protein;

a substantially purified and isolated sequence of nucleic acids consisting of a fragment of SEQ ID NO:3 or a sequence having at least 80% identity to said fragment, with the proviso that said sequence not encode for the p300 protein;

a substantially purified and isolated peptide consisting of SEQ. ID. 4 or a peptide having at least 80% identity to SEQ ID NO:2, with the proviso that said peptide is not the p300 protein; and a substantially purified and isolated peptide consisting of a fragment of SEQ ID NO:4 or a sequence having at least 80% identity to said fragment, with the proviso that said peptide is not the p300 protein.

These and related aspects of the present invention are described in further detail below.

B. COMPOUND 1 competes with β-catenin for CBP. SW480 cells were treated with 5 or 10 μM of COMPOUND 1 or control (0.5% DMSO). 24 hours post treatment, lysates were incubated with beads coated with either control the antibody, or anti-CBP, or anti-p300 antibodies. Co-immunoprecipitated proteins were subjected to gel electrophoresis and immunoblotting using anti-β-catenin antibodies. The arrows point to the immunoprecipitated β-catenin (doublets).

C. CBP (1-111) is the minimal region of interaction with β-catenin. SW480 cells transfected with a CBP deletion series were subjected to immunoprecipitation using anti-β-catenin antibodies coated on Protein A-agarose beads. The immune complexes were washed and subjected to gel electrophoresis followed by immunoblotting using anti-His antibodies. The arrows point to constructs which remained bound to the beads.

D. COMPOUND 1 competes with β-catenin for CBP but not for p300 constructs. Both CBP (1-111,1-211, and 1-351) and p300 (1-111, 1-211, and 1-351) constructs were transfected into SW480 cells (lower panel). 48 hours post transfection whole cell lysates were prepared and were subjected to immunoprecipitation using Protein A-agarose-anti-β-catenin antibodies described above (middle panel). The immune complexes were washed and subjected to gel electrophoresis and immunoblotting using anti-His antibodies. Arrows point to bound proteins (upper panel). For competition assays the immune complexes on the beads were challenged with 50 μM COMPOUND 1.

E. Sequence alignment of CBP and p300 with consensus β-catenin binding motifs (SEQ ID NOS: 47-55). The consensus sequences are boxed. Alignments were performed using the program BLAST for protein sequences in the NCBI database.

F. Sequence alignment of CBP 1-111 (CBP M1, SEQ ID NO:2) and p300 1-111 (p300 M1, SEQ ID NO:4).

Figure 4A:
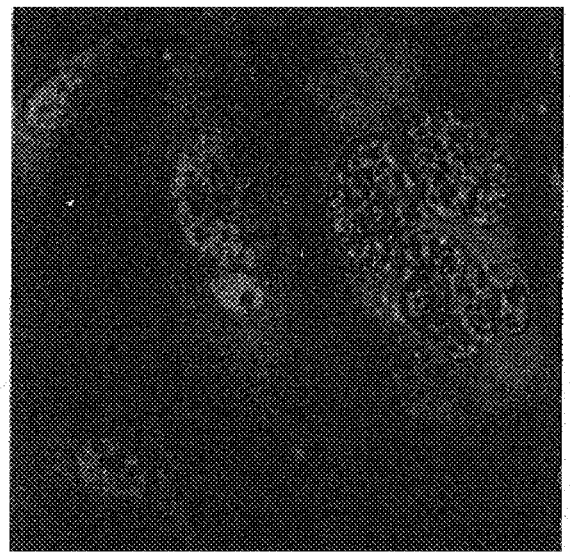
Figure 4A:

FIG. 4. COMPOUND 1 decreases nuclear β-catenin

A. β-catenin immunofluorescence microscopy. Log phase SW480 (left) and HCT116 (right) cells were fixed and stained with either anti-β-catenin red (upper panel, A) or anti-CBP (upper panel, B) green. The center panel represents the superimposed β-catenin and CBP in SW480 (left) and HCT116 (right) cells. The lower panel shows the redistribution of β-catenin to the cytoplasm of SW480 (left) and cytoplasmic membrane of HCT116 cells (right) upon treatment with COMPOUND 1 (25 μM) for 24 hours.

B. Western blot analysis of β-catenin. 25 μg of total protein from the cell extracts of SW480 cells with or without 24 hr treatment of COMPOUND1 was used for detection of cytosolic and nuclear β-catenin.

FIG. 5. COMPOUND 1 inhibits the expression of cyclin D1.

A. Cyclin D1 levels are decreased with COMPOUND 1 treatment. Western blot analysis was performed on 25 μg of SW480 whole cell lysates treated for 4, 8, or 24 hours with either 25 μM of COMPOUND 1 or control (0.5% DMSO). Immunoblotting was performed using anti-Cyclin D1 antibodies (Santa Cruz Biotechnology Inc.).

B. In vivo occupancy of cyclin D1 and c-myc promoters by CBP and p300. ChIP (see material and methods) demonstrates CBP and p300 occupancy of c-myc promoter upon COMPOUND 1 treatment. ChIP assays were performed on promoter of c-myc from SW480 cells which was treated for 8 hours with COMPOUND 1 (25 μM) or control (0.5% DMSO). CBP (AC-26, a generous gift from Dr. David Livingston, Harvard University, Boston, Mass.) or p300 (C-20, Santa Cruz Biotechnology Inc.) specific antibodies were used to evaluate the promoter occupancy by CBP or p300 in presence of COMPOUND 1 or control (DMSO) treatment.

FIG. 6.

A. COMPOUND 1 arrests cells in $G_1$. FACS analysis was performed on SW480 (lower panel) and HCT116 (upper panel) cells treated for 24 hours with either COMPOUND 1 (25 μM) (right) or control (0.5% DMSO (left). $5.5 \times 10^6$ cells were fixed and stained with propidium iodide (PI). $G_0/G_1$, S, and $G_2/M$ are indicated by arrows.

B. COMPOUND 1 selectively activates caspases in colon carcinoma cell lines. SW480 and HCT116 (left graph) cells ($10^5$) along with the normal colonocytes, CCD18Co (right graph) were treated with either control (0.5% DMSO) or COMPOUND 1 (25 μM). 24 hours post treatment, cells were lysed and the caspase-3/7 enzymatic activities were measured. Relative fluorescence units (RFU) were calculated by subtracting the unit values of the blank (control, without cells) from the treated samples (COMPOUND 1 or control) and plotted.

FIG. 7. COMPOUND 1 reduces colony growth in soft agar in a dose dependent manner.

A. Increasing concentrations of 5-fluorouracil (5-FU) (0.5-32 μM) and COMPOUND 1 (0.25-5 μM) were added to SW480 (5000 cells/well) of triplicate wells. Cells were washed and suspended in soft agar growth medium. The number of colonies after 8 days (colonies over 60 μM diameter) were counted and plotted against the compound concentration. Mean±SE of three determinations is indicated. The colony number of control in the absence of the compound was 1,637±71.

B. Schematic representation of the effects of COMPOUND 1. Without intending to be bound by their theory, applicants suggest that the β-catenin/TCF complex regulates the expression of its downstream target genes in a coactivator dependent fashion. More specifically, it is suggested that nuclear β-catenin/TCF differentially associates with CBP or p300 and the trimeric complex drives the expression of a subset of β-catenin/TCF responsive genes. COMPOUND 1 specifically and selectively targets the β-catenin/TCF/CBP and not the β-catenin/TCF/p300 complex and downregulates the expression of genes such as cyclin D1, axin2, and hnkd that are CBP dependent. COMPOUND 1 treatment, through the blockade of the β-catenin/CBP interaction, increases the β-catenin/TCF complexes available for the expression of genes whose promoter can utilize either coactivator (c-myc) or preferably utilize p300 as a coactivator (c-jun and fra-1).

Figure 8:
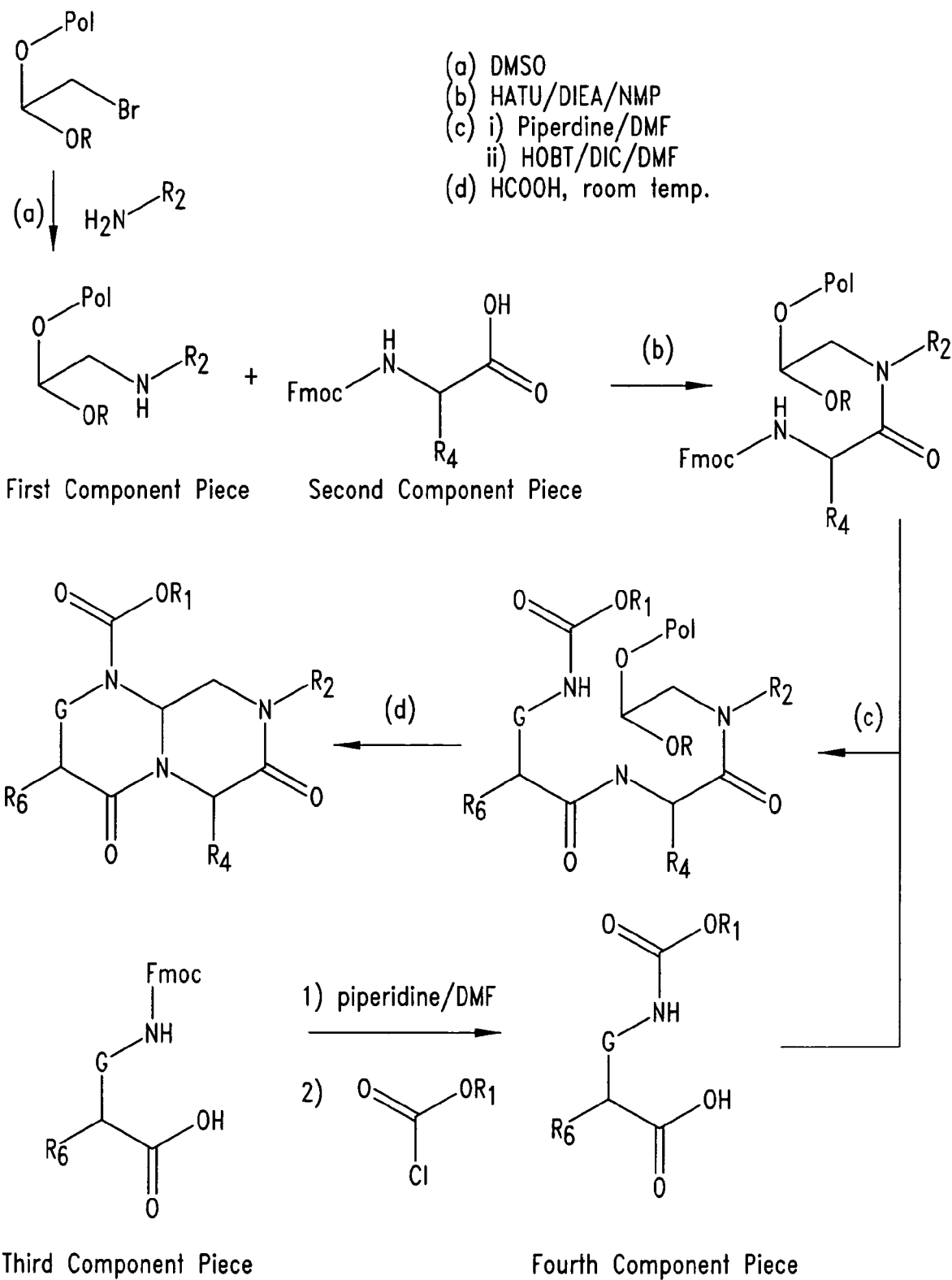

FIG. 8 provides a general synthetic scheme for preparing chemical agents useful in the practice of the present invention.

Figure 9:
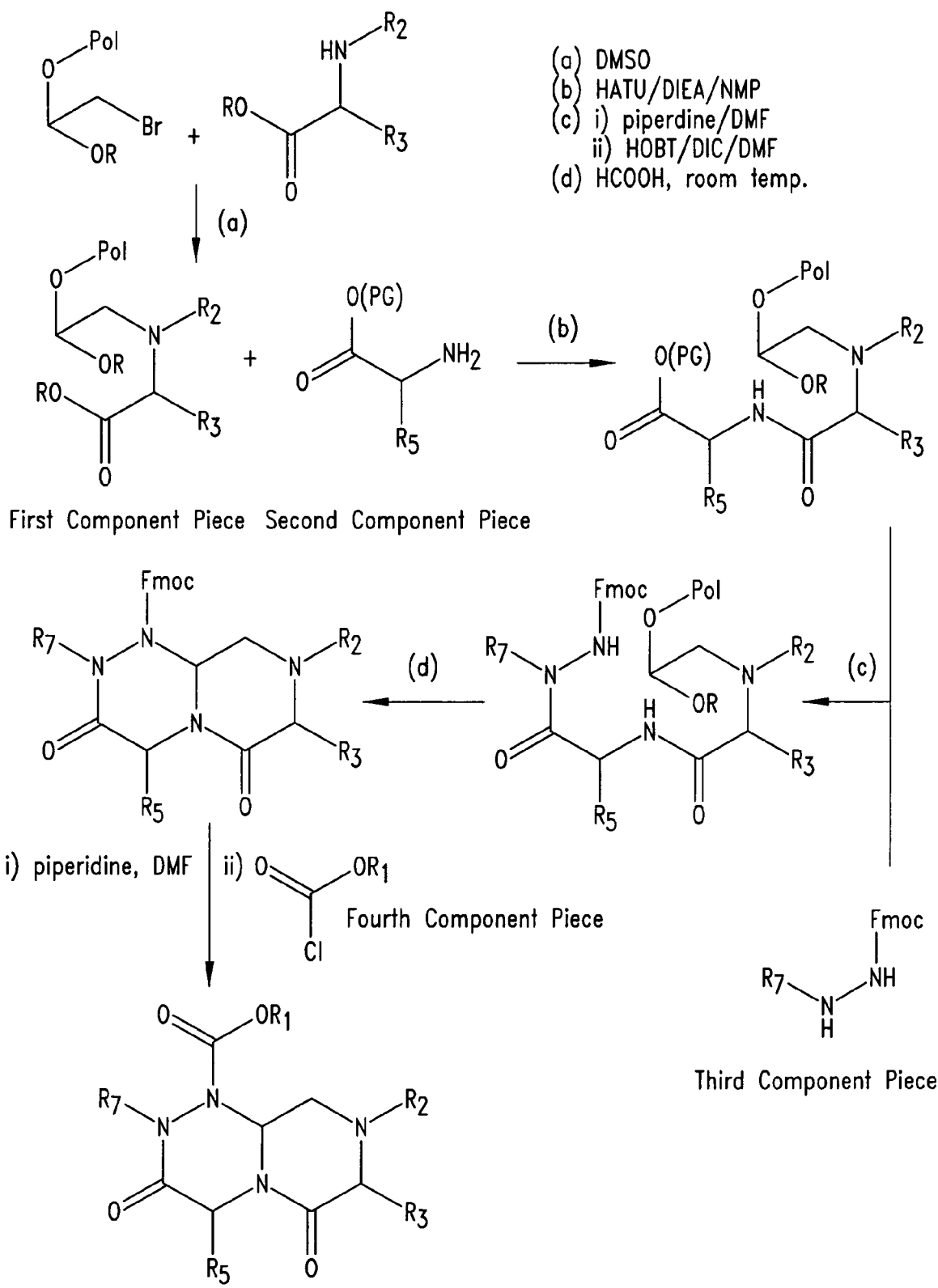

FIG. 9 provides a general synthetic scheme for preparing chemical agents useful in the practice of the present invention.

FIG. 10. Metabolism analysis of COMPOUND3
  A. The diode Array trace (upper panel) and the total ion current (lower panel) for COMPOUND3 and metabolites thereof in rat.
  B. The diode Array trace (upper panel) and the total ion current (lower panel) for COMPOUND3 and metabolites thereof in human.

are promoted by CBP but not p300 are selectively activated, while in a related aspect the invention provides compounds useful in the method. In addition, the present invention provides methods whereby genes that are promoted by p300 but not CBP are selectively activated, while in a related aspect the invention provides compounds useful in this method. In another aspect, the present invention provides method whereby colon carcinoma cells are treated with a chemical agent in order to arrest development at the $G_1$-phase of the cell cycle, where prolonged treatment with the chemical agent induces apoptosis which is not detected in normal colonocytes.

More specific details of these methods and agents are provided below. However, before providing these details, the following definitions are provided to assist the reader in understanding the present disclosure.

Definitions

```
SEQ ID NO:1 is the nucleic acid sequence: tgaggaatca acagccgcca tcttgtcgcg gacccgaccg gggcttcgag cgcgatctac tcggccccgc cggtcccggg ccccacaacc gcccgcgctc gctcctctcc ctcgcagccg gcagggcccc cgaccccccgt ccgggccctc gccggcccgg ccgcccgtgc ccggggctgt tttcgcgagc aggtgaaaat ggctgagaac ttgctggacg gaccgcccaa ccccaaaaga gccaaactca gctcgcccgg tttctcggcg aatgacagca cagattttgg atcattgttt gacttggaaa atgatcttcc tgatgagctg.

SEQ ID NO:2 is the amino acid sequence: MAENLLDGPPNPKR

AKLSSPGFSANDSTDFGSLFDLENDLPDELIPNGGELGLLNSGNLVPDAASKHKQ

LSELLRGGSGSSINPGIGNVSASSPVQQGLGGQAQGQPNSAN.

SEQ ID NO:3 is the nucleic acid sequence: ccttgtttgt gtgctaggct ggggggggaga gagggcgaga gagagcgggc gagagtgggc aagcaggacg ccgggctgag tgctaactgc gggacgcaga gagtgcggag gggagtcggg tcggagagag gcggcagggg ccagaacagt ggcaggggc ccggggcgca cgggctgagg cgaccccccag cccctcccg tccgcacaca cccccaccgc ggtccagcag ccgggccggc gtcgacgcta gggggacca ttacataacc cgcgccccgg ccgtcttctc ccgccgccgc ggcgcccgaa ctgagcccgg ggcgggcgct ccagcactgg.

SEQ ID NO:4 is the amino acid sequence: MAENVVEPGPPSA

KRPKLSSPALSASASDGTDFGSLFDLEHDLPDELINSTELGLTNGGDINQLQTSLG

MVQDAASKHKQLSELLRSGSSPNLNMGVGGPGQVMASQAQQSSPGLGL.
```

DETAILED DESCRIPTION OF THE INVENTION

The present invention provides agents that antagonize β-catenin/TCF-mediated transcription, and methods related thereto. In one aspect, the invention provides methods whereby a subset of β-catenin/TCF-responsive genes are specifically down-regulated, while in a related aspect the invention provides compounds useful in the method. In another aspect, the invention provides methods whereby the binding between CBP and β-catenin is disrupted but the binding between the structurally related co-activator p300 and β-catenin is not disrupted, while in a related aspect the invention provides compounds useful in the method. In another aspect, the present invention provides methods whereby genes that Small molecule inhibitor: the term "small molecule" refers to a chemical compound having a formula weight of less than about 5,000 g/mol. The compound may be organic or inorganic, may be of synthetic or natural original, and may be classified as, for example, a peptide, oligonucleotide, peptide mimetic, oligonucleotide mimetic, oligosaccharide, oligosaccharide mimetic, natural product analog or derivative, or a purely synthetic compound which may incorporate, for example, one or more acyclic, cyclic, carbocyclic, heterocyclic, polycyclic, and/or aromatic, groups. The term "inhibitor" refers to compounds that inhibit, to a statistically significant extent, the binding between two polypeptides as disclosed herein, e.g., β-catenin and CBP, or β-catenin and p300. In other words, in the presence of the inhibitor, the binding between two polypeptides is reduced to a statistically significant extent compared to the binding occurred in the absence of the inhibitor. Preferably, the inhibition is sufficient to achieve an affect on cellular properties, e.g., a therapeutic response in a subject that has received the small molecule inhibitor.

β-catenin:CBP interaction: each of β-catenin and CBP are well known polypeptides. See, e.g., Morin, P. J., *Bioessays* 21:1021-30 (1999) and Hecht et al. *EMBO J.* 19:1839-50 (2000). The interaction between β-catenin and CBP has been documented and measured. See, e.g., Takemaru et al. *J. Cell. Biol.* 149:249-54 (2000). The term β-catenin:CBP interaction refers to the binding that occurs between these two proteins.

Putative: Before a small molecule has been tested for activity, e.g., as a modulator of β-catenin/TCF-activated transcription, the small molecule is considered a putative modulator. When the small molecule demonstrates modulator activity, then it can be termed a β-catenin/TCF-activated transcription modulator. Likewise, before a small molecule has been tested as an inhibitor of a protein-protein interaction, e.g., β-catenin: CBP interaction, the small molecule may be referred to as a putative inhibitor of β-catenin:CBP interaction.

Contacting: When two materials, e.g., chemical compound, protein, oligonucleotide, etc., are both placed in a fluid media, e.g., water or buffer, and have no constraints placed on their movement within that media, then those two materials have been contacted with one another. In addition, when two materials are placed adjacent to one another, so that the two materials touch one another, then those materials are contacted with one another. In performing assays, two materials are contacted with one another when, e.g., they are both placed into an assay medium.

β-catenin refers to a protein that is well known in the art, see, e.g., Morin, P. J., Bioessays 21:1021-30 (1999); Gottardi et al., Curr. Biol. 11:$R_{792}$-4 (2001); Huber et al., Cell 105:391-402 (2001). β-catenin has been identified as both a mediator of cell adhesion at the plasma membrane and as a transcriptional activator.

The term "assay" refers to a process or procedure during which various materials (e.g., chemicals, enzymes, etc.) are contacted with one another under selected conditions that will, or will not, give rise to a detectable event. Whether the event is detected reveals information about the various material(s) and/or the selected condition(s).

The terms "inhibits the binding," "inhibits the interaction," "inhibits complex formation" and the like, each refer to the effect of reducing, to a statistically significant extent, the strength, or degree, or extent, of binding between two proteins. A strong binding may occur when, e.g., two proteins are significantly more stable in complexed form vis-à-vis their uncomplexed forms. Protein-protein binding studies in both quantitative and qualitative terms are well known in the art. Examples in connection with β-catenin binding are described in: Brantjes et al., *Biol. Chem.* 383:255-61 (2002, for β-catenin binding with members of the T-cell factor (TCF)); Gottardi et al., *Curr. Biol.* 11:R792-4 (2001), for describing structural elements of β-catenin that interact with binding partners); and Takemaru et al., J. Cell Biol. 149:249-54 (2000, describing β-catenin interaction with CBP).

The term "CBP protein" refers to the protein that is also known as CREB-binding protein, where CREB is an abbreviation for "cAMP-response element binding". This protein is well known in the art, see, e.g., Takemaru et al., J. Cell Biol. 149:249-54 (2000) and U.S. Pat. No. 6,063,583.

CBP 1-111 refers to the first 111 amino acids of the protein CBP, as identified from the N-terminus of CBP. Amino acids 1-111 for CBP isolated from human are set forth above as SEQ ID NO:2. The corresponding nucleic acid sequence is set forth above as SEQ ID NO:1. Amino acids 1-111 for CBP isolated from mouse is SEQ ID NO:5, as follows:

MAENLLDGPPNPKRAKLSSPGFSANDNT DFGSLFDLENDLPDELIPNGELSLLNS-GNLVPDAASKHKQLSELLRGGSGSSINP GIGN-VSASSPVQQGLGGQAQGQPNSTN. The corresponding nucleic acid sequence from mouse is SEQ ID NO:6, as follows: atggccgaga acttgctgga cggaccgccc aaccccaaac gagccaaact cagctcgccc ggcttctccg cgaatgacaa cacagatttt ggatcattgt ttgacttgga aaatgacctt cctgatgagc tgatccccaa tggagaatta agccttttaa acagtgggaa ccttgttcca gatgctgcgt ccaaacataa acaactgtca gagcttcfta gaggaggcag cggctctagc atcaacccag ggatagggcaa tgtgagtgcc agcagccctg tgcaacaggg ccttggtggc caggctcagg ggcagccgaa cagtacaaac.

p300 1-111 refers to the first 111 amino acids of the protein p300, as identified from the N-terminus of p300. Amino acids 1-111 for p300 isolated from human are identified above as SEQ ID NO:4. The corresponding nucleic acid sequence that encodes for this peptide is set forth above as SEQ ID NO:3.

β-Catenin is known to naturally interact with, i.e., form a complex(es) with, a large number of different proteins, including p300 and CBP (see, e.g., Hecht et al. EMBO J. 19:1839-50 (2000). When in the presence of multiple different potential binding partners, β-catenin will bind with those potential partners to various extents, depending on the strength of the binding between β-catenin and a potential binding partner. Selective inhibition of β-catenin binding occurs when the extent of binding between β-catenin and at least one of those binding partners (a first binding partner) is diminished relative to the extent of binding between β-catenin and at least a different one of those binding partners (a second binding partner). This relative decrease in binding may be seen as reduced binding between β-catenin and the first binding partner with no effect on the binding between β-catenin and the second binding partner; or it may be seen as reduced binding between β-catenin and the first binding partner with increased binding between β-catenin and the second binding partner; or it may be seen as reduced binding between β-catenin and the first binding partner along with reduced binding between β-catenin and the second binding partner so long as the reduction in binding between β-catenin and the first binding partner is greater than the reduction in binding between β-catenin and the second binding partner.

The term "p300 protein" refers to a protein that is well known in the art. See, e.g., Gusterson, R. J. et al., *J. Biol. Chem.* 2003 Feb. 28;278(9):6838-47; An and Roeder, *J. Biol. Chem.* 2003 Jan. 17;278(3):1504-10; Rebel, V. I. et al., *Proc Natl Acad Sci USA.* 2002 Nov. 12;99(23):14789-94; and U.S. Pat. No. 5,658,784, as well as references cited therein.

By substantially purified, it is meant that the nucleic acid or polypeptide is separated and is essentially free from other nucleic acids or polypeptides, i.e., the nucleic acid or polypeptide is the primary and active constituent. The term "isolated", as used herein, refers to a molecule separated from substantially all other molecules normally associated with it in its native state. A substantially purified and isolated molecule is the predominant species present in a preparation. A substantially purified molecule may be greater than 60% free, preferably 75% free, more preferably 90% free, and most preferably 95% free from the other molecules (exclusive of solvent) present in the natural mixture. The term "isolated" is not intended to encompass molecules present in their native state.

The phrase "likelihood of binding to CBP versus p300" refers to the probability of a β-catenin molecule that binds to CBP versus p300. Such a probability may be expressed and/or measured by the ratio of the number of β-catenin molecules that bind to CBP to that of β-catenin molecules that bind to p300 under given conditions. Similarly, an agent that "changes the likelihood of β-catenin binding to CBP versus p300" refers to a compound that changes the ratio as described above when the compound is present in the reaction mixture compared to the ratio when the compound is absent in the reaction mixture.

The phrase "likelihood that a cell will differentiate rather than proliferate" refers to the probability of a cell that will differentiate rather than proliferate. Such a probability may be expressed and/or measured by the ratio of the number of cells that differentiate to that of cells that proliferate under given conditions. An agent that "increases the likelihood that a cell will differentiate rather than proliferate" refers to a compound that increases the ratio of the number of cells that differentiate to that of cells that proliferate when the compound is present compared to the same ratio when the compound is absent. Likewise, an agent that "increases the likelihood that a cell will proliferate rather than differentiate" refers to a compound that increases the ratio of the number of cell that proliferate to that of cells that differentiate when the compound is present compared to the same ratio when the compound is absent.

The phrase "Wnt pathway" refers to a signaling cascade that may be initiated by the binding of Wnt proteins (secreted glycoproteins) to frizzled seven-transmembrane-span receptors. This pathway is known and characterized in the art and is the subject of numerous articles and reviews (see, e.g., Huelsken and Behrens, *J. Cell Sci.* 115: 3977-8, 2002; Wodarz et al., *Annu. Rev. Cell Dev. Biol.* 14:59-88 (1998); Morin, P. J., *Bioessays* 21:1021-30 (1999); Moon et al., *Science* 296:1644-46 (2002); Oving et al., *Eur. J. Clin. Invest* 32:448-57 (2002); Sakanaka et al., *Recent Prog. Horm. Res.* 55: 225-36, 2000).

The phrase "the activity of the Wnt pathway" refers to the activity of at least one component of the pathway. For example, the activity of the Wnt pathway, in certain embodiments, may refer to the activity of β-catenin in inducing expression of targeted genes. Many components of the Wnt pathway are known in the art, and include but are not limited to Cerberus (Cer), FrzB, Dickkopf (DKK), LRP, heterotrimeric G protein, Dsh, casein kinease la (CKla), GSK3β, βTrCP, ACP, Axin, CBP, p300, β-catenin, TCF, Froucho, etc.

A compound that "activates the Wnt pathway" refers to a compound that leads to β-catenin induced expression of target genes when present in a system having the Wnt pathway. Many target genes whose expression is induced by β-catenin are known in the art, and include but are not limited to Conductin, Myc, Twin, Cyclin D1, Nkd, Ubx, En-2, PPARd, Xbra, ID2, Siamois, Xnr3, MMP7, TCF-1, survivin, etc. Such genes may also be referred to as "genes targeted by the Wnt/β-catenin pathway."

The phrase "selectively inhibiting expression of genes targeted by the Wnt/β-catenin pathway" refers to inhibiting the expression of a subset of genes targeted by the Wnt/β-catenin pathway, but not inhibiting the expression of the other genes targeted by the Wnt/β-catenin pathway. Although not wished to be bound to any particular mechanism, the inventors of the present invention speculate that the selective inhibition of gene expression may be accomplished by interrupting the interaction between β-catenin and some, but not all, of its potential binding partners.

Agents

In one aspect the present invention provides agents that may be used in the methods described above. In addition to COMPOUND 1, other agents useful in the methods of the present invention may be identified by screening compounds of the general formula (I):

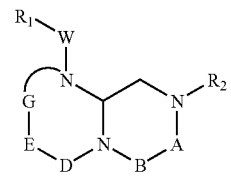

wherein A is —(CHR$_3$)— or —(C=O)—, B is —(CHR$_4$)— or —(C=O)—, D is —(CHR$_5$)— or —(C=O)—, E is -(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1; and R$_1$, R$_2$, R$_3$, R$_4$, R$_5$, R$_6$, R$_7$, R$_8$ and R$_9$ are the same or different and are each independently selected from an amino acid side chain moiety, a derivative of an amino acid side chain moiety, or the remainder of the molecule, and stereoisomers thereof.

In one embodiment, R$_1$, R$_2$, R$_3$, R$_4$, R$_5$, R$_6$, R$_7$, R$_8$ and R$_9$ are independently selected from the group consisting of aminoC$_{2-5}$alkyl, guanidineC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, phenyl, substituted phenyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl, (where the substituents are independently selected from one or more of amino amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, amidazonyl, C$_{1-4}$alkylamino, C$_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazo$C_{1-4}$alkyl, substituted imidazol $C_{1-4}$alkl (where the imidazole sustituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazolinyl$C_{1-4}$alkyl, N-amidinopiperazinyl-N-$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl.

In one embodiment, $R_1$, $R_2$, $R_6$ of E, and $R_7$, $R_8$ and $R_9$ of G are the same or different and represent the remainder of the compound, and $R_3$ of A, $R_4$ of B or $R_5$ of D is selected from an amino acid side chain moiety or derivative thereof.

In another embodiment $R_3$ of A, $R_5$ of D, $R_6$ of E, and $R_7$, $R_8$, and $R_9$ of G are the same or different and represent the remainder of the compound, while one or more of, and in one aspect all of, $R_1$, $R_2$ and $R_4$ of B represent an amino acid sidechain. In this case, the term "remainder of the compound" means any moiety, agent, compound, support, molecule, linker, amino acid, peptide or protein covalently attached to the reverse-turn mimetic structure at $R_3$, $R_5$, $R_6$, $R_7$, $R_8$ and/or $R_9$ positions. This term also includes amino acid side chain moieties and derivatives thereof.

As used herein, the term "remainder of the compound" means any moiety, agent, compound, support, molecule, atom, linker, amino acid, peptide or protein covalently attached to the reverse-turn mimetic structure. This term also includes amino acid side chain moieties and derivatives thereof. In one aspect of the invention, any one or more of the $R_1$, $R_2$, $R_3$, $R_4$, $R_5$, $R_6$, $R_7$, $R_8$ and/or $R_9$ positions may represent the remainder of the compound. In one aspect of the invention, one or more of $R_1$, $R_2$ and $R_4$ represents an amino acid side chain moiety or a derivative thereof.

As used herein, the term "amino acid side chain moiety" represents any amino acid side chain moiety present in naturally occurring proteins including (but not limited to) the naturally occurring amino acid side chain moieties identified in Table A. Other naturally occurring amino acid side chain moieties of this invention include (but are not limited to) the side chain moieties of 3,5-dibromotyrosine, 3,5-diiodotyrosine, hydroxylysine, ?-carboxyglutamate, phosphotyrosine and phosphoserine. In addition, glycosylated amino acid side chains may also be used in the practice of this invention, including (but not limited to) glycosylated threonine, serine and asparagine.

TABLE A

| Amino Acid Side Chain Moiety | Amino Acid |
| --- | --- |
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3$$^+$ | Lysine |
| —(CH$_2$)$_3$NHC(NH$_2$)NH$_2$$^+$ | Arginine |

TABLE A-continued

| Amino Acid Side Chain Moiety | Amino Acid |
| --- | --- |
|  | Histidine |
| —CH$_2$COO$^-$ | Aspartic acid |
| —CH$_2$CH$_2$COO$^-$ | Glutamic acid |
| —CH$_2$CONH$_2$ | Asparagine |
| —CH$_2$CH$_2$CONH$_2$ | Glutamine |
| 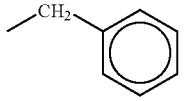 | Phenylalanine |
| 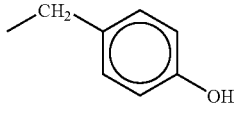 | Tyrosine |
| 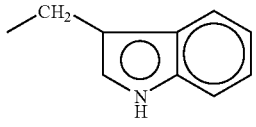 | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| 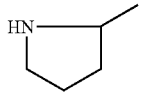 | Proline |
| 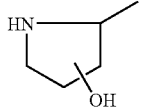 | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and phenylalanine may generally be classified as lower chain alkyl, aryl, or arylalkyl moieties. Derivatives of amino acid side chain moieties include other straight chain or branched, cyclic or noncyclic, substituted or unsubstituted, saturated or unsaturated lower chain alkyl, aryl or arylalkyl moieties.

As used herein, "lower chain alkyl moieties" contain from 1-12 carbon atoms, "lower chain aryl moieties" contain from 6-12 carbon atoms and "lower chain aralkyl moieties" contain from 7-12 carbon atoms. Thus, in one embodiment, the amino acid side chain derivative is selected from a $C_{1-12}$ alkyl, a $C_{6-12}$ aryl and a $C_{7-12}$ arylalkyl, and in a more preferred embodiment, from a $C_{1-7}$ alkyl, a $C_{6-10}$ aryl and a $C_{7-11}$ arylalkyl.

Amino side chain derivatives of this invention further include substituted derivatives of lower chain alkyl, aryl, and arylalkyl moieties, wherein the substituent is selected from (but is not limited to) one or more of the following chemical moieties: —OH, —OR, —COOH, —COOR, —CONH$_2$, —NH$_2$, —NHR, —NRR, —SH, —SR, —SO$_2$R, —SO$_2$H, —SOR and halogen (including F, Cl, Br and I), wherein each occurrence of R is independently selected from straight chain or branched, cyclic or noncyclic, substituted or unsubstituted, saturated or unsaturated lower chain alkyl, aryl and aralkyl moieties. Moreover, cyclic lower chain alkyl, aryl and aralkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

Representative $R_1$, $R_2$, $R_3$, $R_4$, $R_5$, $R_6$, $R_7$, $R_8$ and $R_9$ moieties specifically include (but are not limited to) —OH, —OR, —COR, —COOR, —CONH$_2$, —CONR, —CONRR, —NH$_2$, —NHR, —NRR, —SO$_2$R and —COSR, wherein each occurrence of R is as defined above.

In a further embodiment, and in addition to being an amino acid side chain moiety or derivative thereof (or the remainder of the compound in the case of $R_1$, $R_2$, $R_3$, $R_5$, $R_6$, $R_7$, $R_8$ and $R_9$), $R_1$, $R_2$, $R_3$, $R_4$, $R_5$, $R_6$, $R_7$, $R_8$ or $R_9$ may be a linker facilitating the linkage of the compound to another moiety or compound. For example, the compounds of this invention may be linked to one or more known compounds, such as biotin, for use in diagnostic or screening assay. Furthermore, $R_1$, $R_2$, $R_3$, $R_4$, $R_5$, $R_6$, $R_7$, $R_8$ or $R_9$ may be a linker joining the compound to a solid support (such as a support used in solid phase peptide synthesis). In this embodiment, linkage to another moiety or compound, or to a solid support, is preferable at the $R_1$, $R_2$, $R_7$ or $R_8$, or $R_9$ position, and more preferably at the $R_1$ or $R_2$ position.

In the embodiment wherein A is —(CHR$_3$)—, B is —(C=O)—, D is —(CHR$_5$)—, E is —(C=O)—, and G is —(XR$_7$)$_n$—, the reverse turn mimetic compound of this invention has the following formula (II):

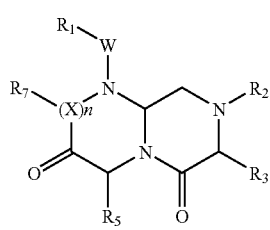

(II)

wherein $R_1$, $R_2$, $R_3$, $R_5$, $R_7$, W, X and n are as defined above. In a preferred embodiment, $R_1$, $R_2$ and $R_7$ represent the remainder of the compound, and $R_3$ or $R_5$ is selected from an amino acid side chain moiety.

In the embodiment wherein A is —(C=O)—, B is —(CHR$_4$)—, D is —(C=O)—, E is -(ZR$_6$)— , G is —(C=O)—(XR$_9$)—, the reverse turn mimetic compound of this invention has the following general formula (III):

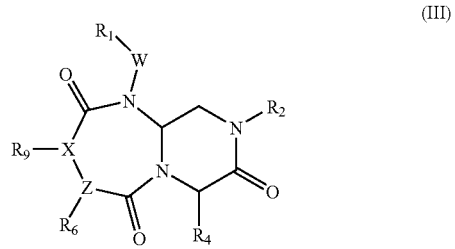

(III)

wherein $R_1$, $R_2$, $R_4$, $R_6$, $R_9$, W and X are as defined above, Z is nitrogen or CH (when Z is CH, then X is nitrogen). In a preferred embodiment, $R_1$, $R_2$, $R_6$ and $R_9$ represent the remainder of the compound, and $R_4$ is selected from an amino acid side chain moiety.

In a more specific embodiment wherein A is —(C=O)—, B is —(CHR$_4$)—, D is —(C=O)—, E is -(ZR$_6$)—, and G is (XR$_7$)$_n$—, the reverse turn mimetic compound of this invention has the following formula (IV):

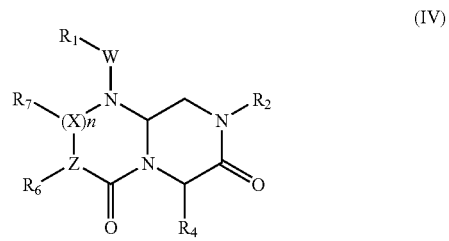

(IV)

wherein $R_1$, $R_2$, $R_4$, $R_6$, $R_7$, W, X and n are as defined above, and Z is nitrogen or CH (when Z is nitrogen, then n is zero, and when Z is CH, then X is nitrogen and n is not zero). In a preferred embodiment, $R_1$, $R_2$, $R_6$ and $R_7$ represent the remainder of the compound, and $R_4$ is selected from an amino acid side chain moiety. In one aspect, $R_6$ or $R_7$ is selected from an amino acid side chain moiety when Z and X are both CH.

These compounds may be prepared by utilizing appropriate starting component molecules (hereinafter referred to as "component pieces"). Briefly, in the synthesis of reverse-turn mimetic structures having formula (I), first and second component pieces are coupled to form a combined first-second intermediate, if necessary, third and/or fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the reverse-turn mimetic structures of this invention. Alternatively, the reverse-turn mimetic structures of formula (I) may be prepared by sequential coupling of the individual component pieces either stepwise in solution or by solid phase synthesis as commonly practiced in solid phase peptide synthesis.

Specific component pieces and the assembly thereof to prepare compounds of the present invention are illustrated in FIG. 8. For example, a "first component piece" may have the following formula S1:

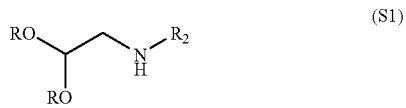

(S1)

wherein $R_2$ is as defined above, and R is a protective group suitable for use in peptide synthesis, where this protection group may be joined to a polymeric support to enable solid-phase synthesis. Suitable R groups include alkyl groups and, in a preferred embodiment, R is a methyl group. In FIG. 8, one of the R groups is a polymeric (solid) support, indicated by "Pol" in the Figure. Such first component pieces may be readily synthesized by reductive amination of $H_2N$—$R_2$ with $CH(OR)_2$—CHO, or by a displacement reaction between $H_2N$—$R_2$ and $CH(OR)_2$—$CH_2$-LG (wherein LG refers to a leaving group, e.g., a halogen (Hal) group).

A "second component piece" may have the following formula S2:

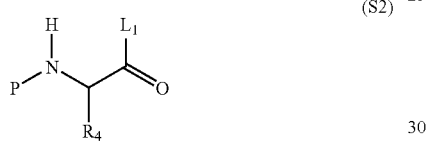

(S2)

where P is an amino protection group suitable for use in peptide synthesis, $L_1$ is hydroxyl or a carboxyl-activation group, and $R_4$ is as defined above. Preferred protection groups include t-butyl dimethylsilyl (TBDMS), t-butyloxycarbonyl (BOC), methyloxycarbonyl (MOC), 9H-fluorenylmethyloxycarbonyl (FMOC), and allyloxycarbonyl (Alloc). N-Protected amino acids are commercially available; for example, FMOC amino acids are available from a variety of sources. In order for the second component piece to be reactive with the first component piece, $L_1$ is a carboxyl-activation group, and the conversion of carboxyl groups to activated carboxyl groups may be readily achieved by methods known in the art for the activation of carboxyl groups. Suitable activated carboxylic acid groups include acid halides where $L_1$ is a halide such as chloride or bromide, acid anhydrides where $L_1$ is an acyl group such as acetyl, reactive esters such as an N-hydroxysuccinimide esters and pentafluorophenyl esters, and other activated intermediates such as the active intermediate formed in a coupling reaction using a carbodiimide such as dicyclohexylcarbodiimide (DCC). Accordingly, commercially available N-protected amino acids may be converted to carboxylic activated forms by means known to one of skill in the art.

In the case of the azido derivative of an amino acid serving as the second component piece, such compounds may be prepared from the corresponding amino acid by the reaction disclosed by Zaloom et al. (*J. Org. Chem.* 46:5173-76, 1981).

Alternatively, the first component piece of the invention may have the following formula S1':

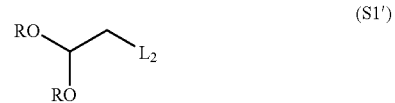

(S1')

wherein R is as defined above and $L_2$ is a leaving group such as halogen atom or tosyl group, and the second component piece of the invention may have the following formula S2':

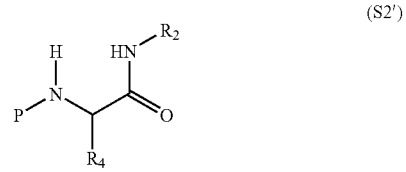

(S2')

wherein $R_2$, $R_4$ and P are as defined above,

A "third component piece" of this invention may have the following formula S3:

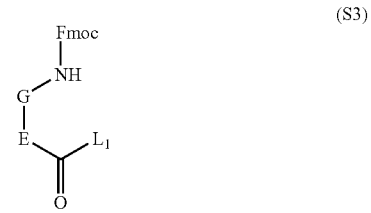

(S3)

where G, E, $L_1$ and $L_2$ are as defined above. Suitable third component pieces are commercially available from a variety of sources or can be prepared by methods well known in organic chemistry.

In FIG. 8, the compound of formula (1) has —(C=O)— for A, —(CHR$_4$)— for B, —(C=O)— for D, and —(CR$_6$)— for E. Compounds of formula (1) wherein a carbonyl group is at position B and an R group is at position B, i.e., compounds wherein A is —(CHR$_3$)— and B is —(C=O)—, may be prepared in a manner analogous to that shown in FIG. 8, as illustrated in FIG. 9. FIG. 9 also illustrates adding a fourth component piece to the first-second-third component intermediate, rather than attaching the fourth component piece to the third component piece prior to reaction with the first-second intermediate piece. In addition, FIG. 9 illustrates the preparation of compounds of the present invention wherein D is —(CHR$_5$)— (rather than —(C=O)— as in FIG. 8), and E is —(C=O)— (rather than —(CHR$_6$)— as in FIG. 8). Finally, FIG. 9 illustrates the preparation of compounds wherein G is NR$_7$.

Thus, as illustrated above, the reverse-turn mimetic compounds of formula (I) may be synthesized by reacting a first component piece with a second component piece to yield a combined first-second intermediate, followed by reacting the combined first-second intermediate with third component pieces sequentially to provide a combined first-second-third-fourth intermediate, and then cyclizing this intermediate to yield the reverse-turn mimetic structure.

The reverse-turn mimetic structures of formula (III) and (IV) may be made by techniques analogous to the modular component synthesis disclosed above, but with appropriate modifications to the component pieces.

For example, the compounds useful in the present invention may be described by general formula:

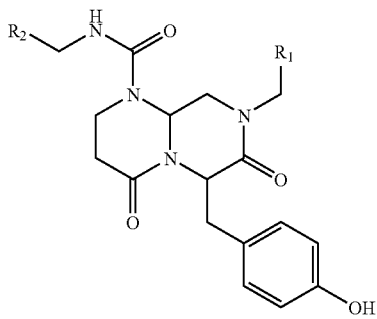

wherein, $R_1$ is a bicyclic aryl ring having 8 to 11 ring members, which may have 1 to 3 heteroatoms selected from nitrogen, oxygen or sulfur, and $R_2$ is a monocyclic aryl ring having 5 to 7 ring members, which may have 1 to 2 heteroatoms selected from nitrogen, oxygen or sulfur, and either aryl ring in the compound may have one or more substituents selected from a group consisting of halide, hydroxy, cyano, lower alkyl, and lower alkoxy group.

Preferably, $R_1$ is naphthyl, quinolinyl or isoquinolinyl group, and $R_2$ is phenyl, pyridyl or piperidyl. More preferably, $R_1$ is naphthyl, and $R_2$ is phenyl.

In another preferred embodiment, the compound has a (6S, 10R)-configuration as follows:

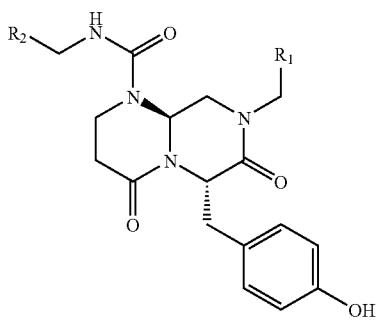

wherein $R_1$ and $R_2$ have the same meanings as defined above. In another preferred embodiment, the compound of general formula (I) has the chemical structure shown in FIG. 1A, where this compound is referred to herein as COMPOUND 1. Compounds having general formula (I) can be prepared from the disclosure of U.S. Pat. No. 6,184,223 assigned to Molecumetics Ltd. The foregoing discussion was presented in terms of the activity of COMPOUND 1, however, other compounds of formula (1) may be screened for activity in the present methods.

Additional exemplary agents useful in the present invention may be found in PCT Application Publication No. WO03/031448, U.S. Application Publication No. US20040072831, U.S. application Ser. Nos. 10/803,179 and 10/826,972, both entitled "Reverse-Turn Mimetics and Method Relating Thereto."

Nucleic Acid Molecules

In one aspect, the present invention provides various nucleic acid molecules encoding polypeptides useful in screening for agents that selectively inhibit the interaction between β-catenin and CBP compared to the interaction between β-catenin and p300.

In certain embodiments, the present invention provides a substantially purified and isolated nucleic acid molecule comprising SEQ ID NO:1 (or SEQ ID NO:6) or a sequence having at least 80%, 85%, 90%, 95%, 98%, or 99% identity to SEQ ID NO:1 (or SEQ ID NO:6), with the proviso that said sequence does not encode the full-length human (or mouse) CBP protein. As used herein, percent identity of two nucleic acids is determined using BLAST programs of Altschul et al. (*J. Mol. Biol.* 215: 403-10, 1990) with their default parameters. These programs implement the algorithm of Karlin and Altschul (*Proc. Natl. Acad. Sci. USA* 87:2264-8, 1990) modified as in Karlin and Altschul (*Proc. Natl. Acad. Sci. USA* 90:5873-7, 1993). BLAST programs are available, for example, at the web site http://www.ncbi.nlm.nih.gov. In a preferred embodiment, the nucleic acid sequence encodes a peptide that binds to β-catenin.

In certain embodiments, the nucleic acid molecule encodes an amino acid sequence that contains no more than 100, 110, 120, 130, 140, 150, 160, 170, 180, 190, 200, 250, or 300 consecutive amino acid residues present within a naturally occurring CBP sequence (e.g., human CBP or mouse CBP). In certain embodiments, the nucleic acid molecule comprises SEQ ID NO:1 or SEQ ID NO:6.

In certain embodiments, the present invention provides a substantially purified and isolated sequence of nucleic acids comprising a fragment of SEQ ID NO:1 (or SEQ ID NO:6) or a sequence having at least 80% identity to said fragment, with the proviso that said sequence does not encode for the CBP protein. In various optional embodiments, the fragment has at least 30, or at least 60, or at least 90, or at least 120, or at least 150, or at least 180, or at least 210, or at least 240, or at least 270, or at least 300 nucleic acids, while independently the fragment has a length of (when possible, based on the minimum length of the fragment), 300, or 270, or 240, or 210, or 180, or 150, or 120, or 90, or 60 nucleic acids. Independently, and also optionally, the fragment within the sequence of nucleic acids has at least 85%, or at least 90%, or at least 95% identity to the fragment of SEQ ID NO:1 (or SEQ ID NO:6). In a preferred embodiment, the sequence of nucleic acids encodes a peptide that binds to β-catenin.

In certain embodiments, the present invention provide a substantially purified and isolated sequence of nucleic acids consisting essentially of SEQ ID NO:1 (or SEQ ID NO:6) or a sequence having at least 80% identity to SEQ ID NO:1 (or SEQ ID NO:6). In various optional embodiments, the sequence has at least 85%, or at least 90%, or at least 95% identity to SEQ ID NO:1 (or SEQ ID NO:6). In a preferred embodiment, the sequence of nucleic acids encodes a peptide that binds to β-catenin.

In certain embodiments, the present invention provides a substantially purified and isolated sequence of nucleic acids consisting essentially of a fragment of SEQ ID NO:1 (or SEQ ID NO:6) or a sequence having at least 80% identity to said fragment. In various optional embodiments, the fragment has at least 30, or at least 60, or at least 90, or at least 120, or at least 150, or at least 180, or at least 210, or at least 240, or at least 270, or at least 300 nucleic acids, while independently the fragment has a length of (when possible, based on the minimum length of the fragment), 300, or 270, or 240, or 210, or 180, or 150, or 120, or 90, or 60 nucleic acids. Independently, and also optionally, the fragment within the sequence of nucleic acids has at least 85%, or at least 90%, or at least 95% identity to the fragment of SEQ ID NO:1 (or SEQ ID NO:6). In a preferred embodiment, the nucleic acid sequence encodes a peptide that binds to β-catenin.

In certain embodiments, the present invention provides a substantially purified and isolated sequence of nucleic acids consisting of SEQ ID NO:1 (or SEQ ID NO:6) or a sequence having at least 80% identity to SEQ ID NO:1 (or SEQ ID NO:6). In various optional embodiments, the sequence has at least 85%, or at least 90%, or at least 95% identity to SEQ ID NO:1 (or SEQ ID NO:6). In a preferred embodiment, the nucleic acid sequence encodes a peptide that binds to β-catenin.

In certain embodiments, the present invention provides a substantially purified and isolated sequence of nucleic acids consisting of a fragment of SEQ ID NO:1 (or SEQ ID NO:6) or a sequence having at least 80% identity to said fragment. In various optional embodiments, the fragment has at least 30, or at least 60, or at least 90, or at least 120, or at least 150, or at least 180, or at least 210, or at least 240, or at least 270, or at least 300 nucleic acids, while independently the fragment has a length of (when possible, based on the minimum length of the fragment), 300, or 270, or 240, or 210, or 180, or 150, or 120, or 90, or 60 nucleic acids. Independently, and also optionally, the fragment within the sequence of nucleic acids has at least 85%, or at least 90%, or at least 95% identity to the fragment of SEQ ID NO:1 (or SEQ ID NO:6). In a preferred embodiment, the sequence of nucleic acids encodes a peptide that binds to β-catenin.

In certain embodiments, the present invention provides a substantially purified and isolated nucleic acid molecule comprising SEQ ID NO:3 or a sequence having at least 80%, 85%, 90%, 95%, 98%, or 99% identity to SEQ ID NO:3 with the proviso that said sequence does not encode the full-length human p300 protein. In certain embodiments, the nucleic acid sequence encodes an amino acid sequence that contains no more than 100, 110, 120, 130, 140, 150, 160, 170, 180, 190, 200, 250, or 300 consecutive amino acid residues present within a naturally occurring p300 sequence (e.g., human p300 or mouse p300). In certain embodiments, the nucleic acid molecule comprises SEQ ID NO:3.

In certain embodiments, the present invention provides a substantially purified and isolated sequence of nucleic acids comprising a fragment of SEQ ID NO:3 or a sequence having at least 80% identity to said fragment, with the proviso that said sequence does not encode a full length p300 protein. In various optional embodiments, the fragment has at least 30, or at least 60, or at least 90, or at least 120, or at least 150, or at least 180, or at least 210, or at least 240, or at least 270, or at least 300 nucleic acids, while independently the fragment has a length of (when possible, based on the minimum length of the fragment), 300, or 270, or 240, or 210, or 180, or 150, or 120, or 90, or 60 nucleic acids. Independently, and also optionally, the fragment within the sequence of nucleic acids has at least 85%, or at least 90%, or at least 95% identity to the fragment of SEQ ID NO:3. In a preferred embodiment, the sequence of nucleic acids encodes a peptide that binds to β-catenin.

In certain embodiments, the present invention provides a substantially purified and isolated sequence of nucleic acids consisting essentially of SEQ ID NO:3 or a sequence having at least 80% identity to SEQ ID NO:3. In various optional embodiments, the sequence has at least 85%, or at least 90%, or at least 95% identity to SEQ ID NO:3. In a preferred embodiment, the sequence of nucleic acids encodes a peptide that binds to β-catenin.

In certain embodiments, the present invention provides a substantially purified and isolated sequence of nucleic acids consisting essentially of a fragment of SEQ ID NO:3 or a sequence having at least 80% identity to said fragment. In various optional embodiments, the fragment has at least 30, or at least 60, or at least 90, or at least 120, or at least 150, or at least 180, or at least 210, or at least 240, or at least 270, or at least 300 nucleic acids, while independently the fragment has a length of (when possible, based on the minimum length of the fragment), 300, or 270, or 240, or 210, or 180, or 150, or 120, or 90, or 60 nucleic acids. Independently, and also optionally, the fragment within the sequence of nucleic acids has at least 85%, or at least 90%, or at least 95% identity to the fragment of SEQ ID NO:3. In a preferred embodiment, the nucleic acid molecule encodes a peptide that binds to β-catenin.

In certain embodiments, the present invention provides a substantially purified and isolated sequence of nucleic acids consisting of SEQ ID NO:3 or a sequence having at least 80% identity to SEQ ID NO:3. In various optional embodiments, the sequence has at least 85%, or at least 90%, or at least 95% identity to SEQ ID NO:3. In a preferred embodiment, the nucleic acid sequence encodes a peptide that binds to β-catenin.

In certain embodiments, the present invention provides a substantially purified and isolated sequence of nucleic acids consisting of a fragment of SEQ ID NO:3 or a sequence having at least 80% identity to said fragment. In various optional embodiments, the fragment has at least 30, or at least 60, or at least 90, or at least 120, or at least 150, or at least 180, or at least 210, or at least 240, or at least 270, or at least 300 nucleic acids, while independently the fragment has a length of (when possible, based on the minimum length of the fragment), 300, or 270, or 240, or 210, or 180, or 150, or 120, or 90, or 60 nucleic acids. Independently, and also optionally, the fragment within the sequence of nucleic acids has at least 85%, or at least 90%, or at least 95% identity to the fragment of SEQ ID NO:3. In a preferred embodiment, the sequence of nucleic acids encodes a peptide that binds to β-catenin.

The nucleic acid molecules according to the present invention may be obtained by digesting nucleic acid molecules encoding full-length CBP and p300 proteins with restriction enzymes or other nucleases. The nucleic acid molecules encoding full-length CBP and p300 proteins may be isolated from genomic DNA or cDNA according to practices known in the art (see, Sambrook and Russell, *Molecular Cloning: A Laboratory Manual*, Cold Spring Harbor Press, 2001). Nucleic acid probes corresponding to a region of SEQ ID NO:1, 3, or 6 may be used to screen either genomic or cDNA libraries. An oligonucleotide suitable for screening genomic or cDNA libraries is generally 20-40 bases in length and may be labeled with a variety of molecules that facilitate detection (e.g., a radionuclide, an enzymatic label, a protein label, a fluorescent label or biotin). Genomic and cDNA libraries may be constructed in a variety of suitable vectors, including plasmid, bacteriophage, yeast artificial chromosome and cosmid vectors. Alternatively, libraries may be purchased from a commercial source (e.g., Clontech, Palo Alto, Calif.).

Other methods may also be used to obtain the nucleic acid molecules according to the present invention. One preferred method is to perform polymerase chain reaction to amplify desired regions of nucleic acid molecules encoding CBP and p300 proteins (e.g., regions encoding a polypeptide comprising the first 111 amino acid residues of CBP or p300). Detailed methods of PCR amplification may be found, for example, in Ausubel et al., *Current Protocols in Molecular Biology*, Greene Publishing Associates and Wiley-Interscience, NY 1995.

Another method for obtaining the nucleic acid molecule is by expression cloning using a polypeptide probe capable of binding CBP 1-111 or p300 1-111. The probe may comprise an antibody against CBP 1-111, p300 1-111 or a fragment thereof. Methods of expression cloning are described in Sambrook and Russell, *Molecular Cloning: A Laboratory Manual*, Cold Spring Harbor Press, 2001; Ausubel et al., *Current Protocols in Molecular Biology*, Greene Publishing Associates and Wiley-Interscience, NY 1995; and Blackwood and Eisenman, *Methods in Enzymology* 254: 229-40, 1995.

Polynucleotides of the present invention may also be made using the techniques of synthetic chemistry given the sequences disclosed herein. The degeneracy of the genetic code permits alternate nucleotide sequence that encode amino acid sequence as set forth in SEQ ID NO:1, 3 or 6. All such nucleotide sequences are within the scope of the present invention.

Nucleic acid sequences encoding CBP or P300 fragments may be fused to a variety of heterologous sequences, such as those encoding affinity tags (e.g., GST and His-tag) and those encoding a secretion signal. The fusion with a sequence encoding an affinity tag facilitates the purification of the encoded polypeptide by allowing the use of affinity purification via the fused tag. The fusion with a sequence encoding a secretion signal also facilitates the purification of the encoded polypeptide by allowing recovery of the polypeptide from the cell lysate, periplasmic space, phloem, or from the growth or fermentation medium. Secretion signals suitable for use are widely available and are well known in the art (e.g., von Heijne, *J. Mol. Biol.* 184:99-105, 1985).

As described above, the nucleic acid molecules of the subject invention may also comprise variants (including alleles) of the native nucleic acid molecules set forth in SEQ ID NO:1, 3, or 6. Such variants include natural variants (e.g., degenerate forms, polymorphisms, splice variants or mutants) and those produced by genetic engineering known in the art.

Polypeptide Sequences

In one aspect, the present invention provides various polypeptide molecules useful in screening for agents that selectively inhibit the interaction between β-catenin and CBP compared to the interaction between β-catenin and p300.

In certain embodiments, the present invention provides a substantially purified and isolated peptide comprising SEQ ID NO:2 (or SEQ ID NO:5) or a peptide having at least 80%, 85%, 90%, 95%, 98%, or 99% identity to SEQ ID NO:2 (or SEQ ID NO:5), with the proviso that said peptide is not a full-length CBP protein (e.g., human or mouse CBP). As used herein, percent identity of two peptides is determined using BLAST programs of Altschul et al. (*J. Mol. Biol.* 215: 403-10, 1990) with their default parameters. These programs implement the algorithm of Karlin and Altschul (*Proc. Natl. Acad. Sci. USA* 87:2264-8, 1990) modified as in Karlin and Altschul (*Proc. Natl. Acad. Sci. USA* 90:5873-7, 1993). BLAST programs are available, for example, at the web site http://www.ncbi.nim.nih.gov. In a preferred embodiment, the peptide binds to β-catenin.

In certain embodiments, the polypeptide molecule according to the present invention comprises an amino acid sequence that contains no more than 100, 110, 120, 130, 140, 150, 160, 170, 180, 190, 200, 250, or 300 consecutive amino acid residues present within a naturally occurring CBP sequence (e.g., human CBP or mouse CBP). In certain embodiments, the polypeptide molecule comprises SEQ ID NO:2 or SEQ ID NO:5.

In certain embodiments, the present invention provides a substantially purified and isolated peptide comprising a fragment of SEQ ID NO:2 or a sequence having at least 80% identity to said fragment, with the proviso that peptide is not a full-length CBP protein. In various optional embodiments, the fragment has at least 10, or at least 20, or at least 30, or at least 40, or at least 50, or at least 60, or at least 70, or at least 80, or at least 90 amino acid (residues), while independently the fragment has a length of (when possible, based on the minimum length of the fragment) 100, or 90, or 80, or 70, or 60, or 50, or 40, or 30, or 20 amino acid (residues). Independently, and also optionally, the fragment within the peptide has at least 85%, or at least 90%, or at least 95% identity to the fragment of SEQ ID NO:2. In a preferred embodiment, the peptide binds to β-catenin.

In certain embodiments, the present invention provides a substantially purified and isolated peptide consisting essentially of SEQ ID NO:2 or a peptide having at least 80% identity to SEQ ID NO:2. In various optional embodiments, the peptide has at least 85%, or at least 90%, or at least 95% identity to SEQ ID NO:2. In a preferred embodiment, the peptide binds to β-catenin.

In certain embodiments, the present invention provides a substantially purified and isolated peptide consisting essentially of a fragment of SEQ ID NO:2 or a sequence having at least 80% identity to said fragment. In various optional embodiments, the fragment has at least 10, or at least 20, or at least 30, or at least 40, or at least 50, or at least 60, or at least 70, or at least 80, or at least 90 amino acid (residues), while independently the fragment has a length of (when possible, based on the minimum length of the fragment) 100, or 90, or 80, or 70, or 60, or 50, or 40, or 30, or 20 amino acid (residues). Independently, and also optionally, the fragment within the peptide has at least 85%, or at least 90%, or at least 95% identity to the fragment of SEQ ID NO:2. In a preferred embodiment, the peptide binds to β-catenin.

In certain embodiments, the present invention provides a substantially purified and isolated peptide consisting of SEQ ID NO:2 or a peptide having at least 80% identity to SEQ ID NO:2, with the proviso that said peptide is not the CBP protein. In various optional embodiments, the peptide has at least 85%, or at least 90%, or at least 95% identity to SEQ ID NO:2. In a preferred embodiment, the peptide binds to β-catenin.

In certain embodiments, the present invention provides a substantially purified and isolated peptide consisting of a fragment of SEQ ID NO:2 or a sequence having at least 80% identity to said fragment. In various optional embodiments, the fragment has at least 10, or at least 20, or at least 30, or at least 40, or at least 50, or at least 60, or at least 70, or at least 80, or at least 90 amino acid (residues), while independently the fragment has a length of (when possible, based on the minimum length of the fragment) 100, or 90, or 80, or 70, or 60, or 50, or 40, or 30, or 20 amino acid (residues). Independently, and also optionally, the fragment within the peptide has at least 85%, or at least 90%, or at least 95% identity to the fragment of SEQ ID NO:2. In a preferred embodiment, the peptide binds to β-catenin.

In certain embodiments, the present invention provides a substantially purified and isolated nucleic acid molecule comprising SEQ ID NO:4 or a sequence having at least 80%, 85%, 90%, 95%, 98%, or 99% identity to SEQ ID NO:3 with the proviso that said sequence does not encode the full-length human p300 protein. In certain embodiments, the polypeptide comprises an amino acid sequence that contains no more than 100, 110, 120, 130, 140, 150, 160, 170, 180, 190, 200, 250, or 300 consecutive amino acid residues present within a naturally occurring p300 sequence (e.g., human p300 or mouse p300). In certain embodiments, the polypeptide comprises SEQ ID NO:4.

In certain embodiments, the present invention provides a substantially purified and isolated peptide comprising a fragment of SEQ ID NO:4 or a sequence having at least 80% identity to said fragment, with the proviso that peptide is not a full-length p300 protein. In various optional embodiments, the fragment has at least 10, or at least 20, or at least 30, or at least 40, or at least 50, or at least 60, or at least 70, or at least 80, or at least 90 amino acid (residues), while independently the fragment has a length of (when possible, based on the minimum length of the fragment) 100, or 90, or 80, or 70, or 60, or 50, or 40, or 30, or 20 amino acid (residues). Independently, and also optionally, the fragment within the peptide has at least 85%, or at least 90%, or at least 95% identity to the fragment of SEQ ID NO:4. In a preferred embodiment, the peptide binds to α-catenin.

In certain embodiments, the present invention provides a substantially purified and isolated peptide consisting essentially of SEQ ID NO:4 or a peptide having at least 80% identity to SEQ ID NO:4. In various optional embodiments, the peptide has at least 85%, or at least 90%, or at least 95% identity to SEQ ID NO:4. In a preferred embodiment, the peptide binds to β-catenin.

In certain embodiments, the present invention provides a substantially purified and isolated peptide consisting essentially of a fragment of SEQ ID NO:4 or a sequence having at least 80% identity to said fragment. In various optional embodiments, the fragment has at least 10, or at least 20, or at least 30, or at least 40, or at least 50, or at least 60, or at least 70, or at least 80, or at least 90 amino acid (residues), while independently the fragment has a length of (when possible, based on the minimum length of the fragment) 100, or 90, or 80, or 70, or 60, or 50, or 40, or 30, or 20 amino acid (residues). Independently, and also optionally, the fragment within the peptide has at least 85%, or at least 90%, or at least 95% identity to the fragment of SEQ ID NO:4. In a preferred embodiment, the peptide binds to β-catenin.

In certain embodiments, the present invention provides a substantially purified and isolated peptide consisting of SEQ ID NO:4 or a peptide having at least 80% identity to SEQ ID NO:4, with the proviso that said peptide is not the CBP protein. In various optional embodiments, the peptide has at least 85%, or at least 90%, or at least 95% identity to SEQ ID NO:4. In a preferred embodiment, the peptide binds to β-catenin.

In certain embodiments, the present invention provides a substantially purified and isolated peptide consisting of a fragment of SEQ ID NO:4 or a sequence having at least 80% identity to said fragment. In various optional embodiments, the fragment has at least 10, or at least 20, or at least 30, or at least 40, or at least 50, or at least 60, or at least 70, or at least 80, or at least 90 amino acid (residues), while independently the fragment has a length of (when possible, based on the minimum length of the fragment) 100, or 90, or 80, or 70, or 60, or 50, or 40, or 30, or 20 amino acid (residues). Independently, and also optionally, the fragment within the peptide has at least 85%, or at least 90%, or at least 95% identity to the fragment of SEQ ID NO:4. In a preferred embodiment, the peptide binds to β-catenin.

In certain embodiments, the polypeptides of the present invention contain conservative amino acid changes, i.e., substitutions of similarly charged or uncharged amino acids of SEQ ID NO:2 or 4. A conservative amino acid change involves substitution of one amino acid for another amino acid of a family of amino acids with structurally related side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and unchareged polar (glycine, asparagines, glutamine, cysteine, serine, threonine, tyrosine) amino acids. Phenylalanie, tryptophan, and tyrosine are sometimes classified as aromatic amino acids. Non-naturally occurring amino acids can also be used to form polypeptides of the present invention.

The present invention also provides CBP or P300 fusion proteins comprising CBP or P300 fragments or homologues thereof fused to amino acid sequences comprising one or more heterologous polypeptides. Such heterologous polypeptides may correspond to naturally occurring polypeptides of any source or may be recombinantly engineered amino acid sequences. Fusion proteins are useful for purification, generating antibodies against amino acid sequences, and for use in various assay systems. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions.

The polypeptides of the present invention can be obtained by a variety of methods known in the art. For example, a CBP (or p300) fragment comprising SEQ ID NO:2 (or SEQ ID NO:4) can be isolated by biochemical methods such as affinity chromatography. Affinity matrices that can be used for CBP or p300 polypeptide can be a solid phase having attached thereto anti-CBP or anti-p300 monoclonal or polyclonal antibodies prepared against SEQ ID NO:2 or 4 or a fragment thereof. Alternatively, polypeptides known to bind CBP or p300 (e.g., β-catenin) can be used as affinity matrices to isolate a CBP or p300 polypeptides or fragment thereof.

Other biochemical methods for isolating CBP, p300, or fragments thereof include preparative gel electrophoresis, gel filtration, affinity chromatography, ion exchange and reversed phase chromatography, chromatofocusing, isoelectric focusing and sucrose or glycerol density gradients (Deutscher, *Methods in Enzymology: Guide to Protein Purification*, Vol. 182, Academic Press, Inc., San Diego, Chapter 38, 1990; Balch et al., *Methods in Enzymology*, Vol. 257, Academic Press, Inc., San Diego, Chapter 8, 1995).

A polypeptide according to the present invention can also be produced by chemical synthesis, for example, by the solid phase peptide synthesis method (Merrifield et al., *J. Am. Chem. Soc.* 85:2149, 1964). Standard solution methods well known in the art also can be used to synthesize the polypeptide comprising SEQ ID NO:2 or 4 or homologues thereof (Bodanszky, *Principles of Peptide Synthesis*, Springer-Verlag, Berlin, 1984; Bodanszky, *Peptide Chemistry*, Springer-Verlag, Berlin, 1993). A newly synthesized polypeptide can be isolated, for example, by high performance liquid chromatography and can be characterized using mass spectrometry or amino acid sequence analysis.

A polypeptide according to the present invention can also be produced by recombinant DNA methods. Nucleic acids encoding SEQ ID NO:2 or 4 or homologues thereof provided by the invention can be cloned into an appropriate vector for expression. Such a vector is commercially available or can be constructed by those skilled in the art and contains expression elements necessary for the transcription and translation. The selected vector can also be used in a procaryotic or eukaryotic host system, as appropriate, provided the expression and regulatory elements are of compatible origin. A recombinant polypeptide produced in a host cell or secreted from the cell can be isolated using, for example, affinity chromotography with an antibody against SEQ ID NO:2 or 4 or fragment thereof, ionic exchange chromatography, HPLC, size exclusion chromatography, ammonium sulfate crystallization, electrofocusing, or preparative gel electrophoresis (see generally Ausubel et al., supra; Sambrook et al., supra). An isolated purified protein is generally evidenced as a single band on an SDS-PAGE gel stained with Coomassie Blue.

The present invention also provides fusion proteins comprising SEQ ID NO:2 or 4 or a homologue thereof and a heterologous polypeptide. Such fusion proteins can be made by covalently linking two protein segments or by standard procedures in the art of molecular biology. For example, recombinant DNA methods can be used to prepare fusion proteins by making a DNA construct which comprises coding sequences selected from SEQ ID NO:2 or 4 in proper reading frame with nucleotides encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Methods of Use

The present invention provides compounds of formula (I) that inhibit a subset of β-catenin/TCF induced transcription. For instance, as described in detail in the example, COMPOUND1 selectively blocks the interaction of β-catenin with CBP without interfering with the interaction of β-catenin with p300, which is closely related to CBP. The treatment of COMPOUND1 causes redistribution of β-catenin from nucleus to the cytoplasm, selectively inhibits the association of CBP with the promoters of certain target genes (e.g., c-myc and cyclin D1) and thus inhibits the expression of these genes. In addition, COMPOUND1 selectively activates apoptotic caspases in transformed but not normal colonocytes, causes a G1/S-phase arrest of cancer cells and reduces proliferation of transformed colorectal cells. Accordingly, compounds of the present invention may have various utilities such as treating cancer, reducing tumor growth, increasing apoptosis, modulating β-catenin-induced gene expression, and the like.

In one aspect, the present invention provides a method for selectively inhibiting β-catenin/CBP interaction relative to β-catenin/p300 interaction, the method comprising administering a compound to a composition, where the composition comprises β-catenin, CBP and p300, and the compound selectively inhibits β-catenin/CBP interaction relative to β-catenin/p300 interacts.

In another aspect, the present invention provides a method for selectively inhibiting β-catenin/p300 interaction relative to β-catenin/CBP interaction, the method comprising administering a compound to a composition, where the composition comprises β-catenin, CBP and p300, and the compound selectively inhibits β-catenin/p300 interaction relative to β-catenin/CBP interacts. Certain analogs of COMPOUND1 are selective for the β-catenin/p300 protein complex.

Protein-protein interaction (e.g., the interaction between β-catenin and p300, and the interaction between β-catenin and CBP), as well as the effects of an agent on the protein-protein interaction may be characterized and/or measured by any appropriate methods known in the art. Such methods may include in vitro binding assays using affinity purified recombinant β-catenin, CBP and p300 proteins or fragments thereof. In certain embodiments, one protein component may be first immobilized to a solid support (e.g., an ELISA plate) to facilitate the detection and measurement of protein-protein interaction. Protein-protein interaction may also be characterized using in vivo binding assays such as immunoprecipitation and western blot analysis as described in the examples.

In another aspect, the present invention provides a method for enhancing translocation of β-catenin from the nucleus to the cytosol, the method comprising administering a compound to a cell, where the cell comprises a nucleus and a cytosol, and the nucleus comprises β-catenin, and the compound causes translocation of β-catenin from the nucleus to the cytosol. The translocation of β-catenin from the nucleus to the cytosol may be detected using immunofluorescence analysis as described in the examples.

In another aspect, the present invention provides a method for selectively inhibiting expression of genes targeted by the WNT/β-catenin pathway, the method comprising administering a compound to a composition, the composition comprising genes targeted by the WNT/β-catenin pathway, the compound causing a change in expression of the genes targeted by the WNT/β-catenin pathway.

As indicated above, the present invention provides methods for impacting CBP-promoted gene expression, and in a preferred embodiment provides methods for impacting CBP-promoted gene expression in preference to impacting p300-promoted gene expression. The present invention also provides methods for impacting p300-promoted gene expression and, in a preferred embodiment, provides methods for impacting p300-promoted gene expression in preference to impacting CBP-promoted gene expression. This invention is particularly remarkable in view of the structural similarity between CBP and p300, and the fact that many persons skilled in the art view CBP and p300 as having essentially equivalent biological function. This efficacy may be applied to, e.g., impacting survivin expression.

In one aspect, the present invention provides a method for modulating β-catenin-induced gene expression comprising contacting a composition with an agent, where the composition comprises β-catenin, CBP and p300, where β-catenin has a likelihood of binding to CBP versus p300, and the agent is contacted with the composition in an amount effective to change the likelihood of β-catenin binding to CBP versus p300. In exemplary aspects, the modulation may take the form of increasing the binding of CBP to β-catenin, optionally while decreasing the binding of p300 to β-catenin. Or, the modulation may take the form of increasing the binding of p300 to β-catenin, optionally while decreasing the binding of CBP to β-catenin. The composition may be a cell.

Expression of genes of interest and the effects of an agent on the expression of these genes may be performed by any appropriate methods known in the art. Such methods include the use of cDNA microarray, RT-PCR with primers for amplifying the genes of interest, and measuring reporter activities driven by the promoters of the genes of interest and ChIP assays.

In another aspect, the present invention provides a method for modulating the activity of the Wnt pathway comprising (a) contacting (i) a composition comprising the components of the Wnt pathway with (ii) a compound that activates the Wnt pathway, to provide activated Wnt pathway; and (b) modulating the activity of the Wnt pathway with a chemical agent that completely or substantially interferes with binding between p300 and β-catenin but causes little or no interference with binding between CBP and β-catenin.

In another aspect, the present invention provides a method for enhancing cell proliferation comprising:

(a) providing a cell population under conditions where a proportion of the population will proliferate and a proportion of the population will differentiate; and (b) adding a chemical agent to the population, where the agent causes an increase in the proportion of the cells that proliferate relative to the proportion of the cells that differentiate.

Cell proliferation and cell differentiation may be characterized by any appropriate methods known in the art. Such methods include flow cytometric analysis and soft agar assays as described in the examples.

In another aspect, the present invention provides a method for maintaining a stem cell in an undifferentiated state, comprising contacting the stem cell with an agent that inhibits cell differentiation or promotes cell proliferation in an amount effective to maintain the stem cell in an undifferentiated state. In certain embodiments, the agent is capable of reducing the interaction between β-catenin and p300 without interfering with the interaction between β-catenin and CBP.

Stem cell therapy offers an opportunity to treat many degenerative diseases caused by the premature death of malfunction of specific cell types and the body's failure to replace or restore them. Possible therapeutic uses of stem cells include immunological conditioning of patients for organ transplants, treatment of autoimmune diseases such as muscular dystrophy, multiple sclerosis and rheumatoid arthritis, repair of damaged tissues such as stroke, spinal injury and burn, treatment of neurodegenerative disease like Lou Gehrig's disease, and neurological conditions such as Parkinson's Huntington's and Alzheimer's diseases, treatment of leukaemia, sickle cell anaemia, heart disease, and diabetes. For most stem cell therapy, embryonic stem cells or adult stem cells may be cultured in vitro, induced to differentiate to the desired cell type and transplant to a patient. For successful culture of stem cells, stem cells need to be maintained in an undifferentiated condition.

To maintain stem cells in an undifferentiated condition, compounds according to the present invention, such as those that promote cell proliferation or inhibit cell differentiation, may be used at various stages of stem cell culture. For instance, such a compound may be used when the stem cells are isolated from their source tissue. Alternatively, it may be added to culture media after certain period of culture. It may also be continuously present in culture media to maintain the stem cells in an undifferentiated state. The concentration of the compound may be optimized by adjusting the amount of the compound to the level at which stem cells are maintained in an undifferentiated state, or the differentiation of stem cells is reduced compared to the stem cells cultured in the absence of the compounds, and other aspects of the cell culture (e.g., cell viability rate and cell proliferation rate) is not adversely affected.

These and other methods of the present invention may be practiced with a chemical agent, such as a chemical agent identified herein as COMPOUND 1 as well as its analogs.

Screening Assays

Compounds of formula (I), as well as other agents, may be screened for activity as described herein and according to the following methods.

For instance, in one aspect, the present invention provides a method for identifying a small molecule inhibitor of the β-catenin:CBP interaction comprising the steps of: (a) contacting a putative beta-catenin:CBP small molecule inhibitor with a moiety comprising CBP 1-111; (b) contacting the admixture of step (a) with a moiety comprising β-catenin; (c) determining, by assay means, if said molecule of step (a) inhibits the binding of the moiety comprising β-catenin of step (b) with the moiety comprising CBP 1-111 of step (a); and (d) identifying, upon determination that said small molecule of step (a) inhibits the binding of said moiety comprising CBP 1-111 with the moiety comprising β-catenin, the small molecule of step (a) as an inhibitor of beta-catenin:CBP interaction. Optionally, the method may further comprise the steps of: (e) contacting the identified small molecule inhibitor of β-catenin:CBP interaction of step (d) with an admixture comprising (1) a moiety comprising p300 1-111 and (2) β-catenin; (f) determining, by assay means, if said molecule of step (e) does not inhibit the binding of said moiety comprising p300 1-111 with β-catenin; and (g) confirming, upon determination that said small molecule of step (e) does not inhibit the binding of said moiety comprising p300 1-111 with said β-catenin, that said small molecule is a selective inhibitor of β-catenin:CBP interaction.

In another aspect, the present invention provides a method for identifying a small molecule inhibitor of the β-catenin:CBP interaction comprising the steps of: (a) contacting a putative β-catenin:CBP small molecule inhibitor with a moiety comprising β-catenin; (b) contacting the admixture of step (a) with a moiety comprising CBP 1-111; (c) determining, by assay means, if said molecule of step (a) inhibits the binding of the moiety comprising CBP 1-111 of step (b) with the moiety comprising β-catenin of step (a); and (d) identifying, upon determination that said small molecule of step (a) inhibits the binding of said moiety comprising β-catenin with the moiety comprising CBP 1-111, the small molecule of step (a) as an inhibitor of β-catenin:CBP interaction. Optionally, this method may further comprise the steps of: (e) contacting the identified small molecule inhibitor of β-catenin:CBP interaction of step (d) with an admixture comprising (1) a moiety comprising p300 1-111 and (2) β-catenin; (f) determining, by assay means, if said molecule of step (e) does not inhibit the binding of said moiety comprising p300 1-111 with β-catenin; and (g) confirming, upon determination that said small molecule of step (e) does not inhibit the binding of said moiety comprising p300 1-111 with said β-catenin, that said small molecule is a selective inhibitor of β-catenin:CBP interaction.

In another aspect, the present invention provides a method for identifying a small molecule inhibitor of the β-catenin:CBP interaction comprising the steps of: (a) contacting a putative beta-catenin:CBP small molecule inhibitor with a moiety, said moiety comprising (1) β-catenin associated with CBP 1-111; (b) determining, by assay means, if said molecule of step (a) disassociates CBP 1-111 from β-catenin; and (c) identifying, upon determination that said small molecule of step (a) disassociates the binding of β-catenin from CBP 1-111, the small molecule of step (a) as an inhibitor of β-catenin:CBP interaction. Optionally, the method may further comprise the steps: (d) contacting the identified small molecule inhibitor of β-catenin:CBP interaction of step (c) with an admixture comprising (1) a moiety comprising p300 1-111 and (2) β-catenin; (e) determining, by assay means, if said molecule of step (d) does not inhibit the binding of said moiety comprising p300 1-111 with β-catenin; and (f) confirming, upon determination that said small molecule of step (d) does not inhibit the binding of said moiety comprising p300 1-111 with said β-catenin, that said small molecule is a selective inhibitor of β-catenin:CBP interaction.

In one aspect, the present invention provides a method for identifying a small molecule inhibitor of the β-catenin:p300 interaction comprising the steps of: (a) contacting a putative beta-catenin:p300 small molecule inhibitor with a moiety comprising p300 1-111; (b) contacting the admixture of step (a) with a moiety comprising β-catenin; (c) determining, by assay means, if said molecule of step (a) inhibits the binding of the moiety comprising β-catenin of step (b) with the moiety comprising p300 1-111 of step (a); and (d) identifying, upon determination that said small molecule of step (a) inhibits the binding of said moiety comprising p300 1-111 with the moiety comprising β-catenin, the small molecule of step (a) as an inhibitor of beta-catenin:CBP interaction. Optionally, the method may further comprise the steps of: (e) contacting the identified small molecule inhibitor of β-catenin:p300 interaction of step (d) with an admixture comprising (1) a moiety comprising CBP 1-111 and (2) β-catenin; (f) determining, by assay means, if said molecule of step (e) does not inhibit the binding of said moiety comprising CBP 1-111 with β-catenin; and (g) confirming, upon determination that said small molecule of step (e) does not inhibit the binding of said moiety comprising CBP 1-111 with said β-catenin, that said small molecule is a selective inhibitor of β-catenin:p300 interaction.

In another aspect, the present invention provides a method for identifying a small molecule inhibitor of the β-catenin:p300 interaction comprising the steps of: (a) contacting a putative β-catenin:p300 small molecule inhibitor with a moiety comprising β-catenin; (b) contacting the admixture of step (a) with a moiety comprising p300 1-111; (c) determining, by assay means, if said molecule of step (a) inhibits the binding of the moiety comprising p300 1-111 of step (b) with the moiety comprising β-catenin of step (a); and (d) identifying, upon determination that said small molecule of step (a) inhibits the binding of said moiety comprising β-catenin with the moiety comprising p300 1-111, the small molecule of step (a) as an inhibitor of β-catenin:p300 interaction. Optionally, this method may further comprise the steps of: (e) contacting the identified small molecule inhibitor of β-catenin:p300 interaction of step (d) with an admixture comprising (1) a moiety comprising CBP 1-111 and (2) β-catenin; (f) determining, by assay means, if said molecule of step (e) does not inhibit the binding of said moiety comprising CBP 1-111 with β-catenin; and (g) confirming, upon determination that said small molecule of step (e) does not inhibit the binding of said moiety comprising CBP 1-111 with said β-catenin, that said small molecule is a selective inhibitor of P-catenin:p300 interaction.

In another aspect, the present invention provides a method for identifying a small molecule inhibitor of the β-catenin:p300 interaction comprising the steps of: (a) contacting a putative beta-catenin:p300 small molecule inhibitor with a moiety, said moiety comprising (1) β-catenin associated with p300 1-111; (b) determining, by assay means, if said molecule of step (a) disassociates p300 1-111 from β-catenin; and (c) identifying, upon determination that said small molecule of step (a) disassociates the binding of β-catenin from p300 1-111, the small molecule of step (a) as an inhibitor of β-catenin:p300 interaction. Optionally, the method may further comprise the steps: (d) contacting the identified small molecule inhibitor of β-catenin:p300 interaction of step (c) with an admixture comprising (1) a moiety comprising CBP 1-111 and (2) β-catenin; (e) determining, by assay means, if said molecule of step (d) does not inhibit the binding of said moiety comprising CBP 1-111 with β-catenin; and (f) confirming, upon determination that said small molecule of step (d) does not inhibit the binding of said moiety comprising CBP 1-111 with said β-catenin, that said small molecule is a selective inhibitor of β-catenin:p300 interaction.

Protein-protein interaction (e.g., the interaction between β-catenin and p300, and the interaction between β-catenin and CBP), as well as the effects of an agent on the protein-protein interaction may be characterized and/or measured by any appropriate methods known in the art. For example, a suitable assay means for the methods of the invention is isothermal titration calorimetry (ITC). ITC experiments may be performed using a MicroCal MCS isothermal titration calorimeter (MicroCal, Northampton Mass.) essentially as recommended by the manufacturer. Briefly, the CBP C1 fragment is extensively dialyzed against dialysis buffer containing 50 mM PIPES (pH 7.5) and 0.1 mM EDTA. DMSO is added to the protein sample to a final concentration of 0.05% to correspond to the diluted drug sample. The protein concentration is determined using a Bradford protein assay (Bio-Rad laboratories, Hercules Calif.) using Bovine plasma gamma globulin as a standard, (Bio-Rad). Due to solubility constraints, ITC experiments are performed by injecting 5-15 ul CBP C1 [223 uM], into the sample cell filled with 23.3 uM of putative small molecule inhibitor. Heats of dilution are estimated after saturation of the putative small molecule inhibitor in the sample cell and thermodynamic parameters are calculated using the Origin 5.0 software package (MicroCal). A higher heat of dilution indicates a stronger binding between the putative small molecule inhibitor and the CBP fragment. A stronger binding between the putative small molecule inhibitor and the CBP fragment identifies a small molecule that may be more effective at disrupting CBP binding, e.g., CBP binding to beta-catenin.

Pharmaceutical Compositions and Administration

The nucleic acid molecules, peptides, and compounds according to the present invention can be incorporated into pharmaceutical compositions suitable for administration. Such compositions typically comprise the nucleic acid molecule, peptide, or compound and a pharmaceutically acceptable carrier. "Pharmaceutically acceptable carrier" refers to solvents, dispension media, coatings, antibacterial and antifungal agents, isotonic and absorption delaying agents and the like, compatible with pharmaceutical administration. The use of such media and agents for pharmaceutically active substances is well known in the art. Supplementary active compound can also be incorporated into the compositions.

The pharmaceutical composition of the present invention may be administered parenterally, topically, orally, or locally for therapeutic treatment. A variety of aqueous carriers may be used, e.g., water, buffered water, 0.4% saline, 0.3% glycine and the like, and may include other proteins for enhancing stability, such as albumin, lipoprotein, globulin, etc. The resulting composition may be sterilized by conventional, well-known sterilization techniques. The solutions may be packaged for use or filtered under aseptic conditions and lyophilized, the lyophilized preparation being combined with a sterile solution prior to administration.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder (e.g., microcrystalline cellulose, gum tragacanth or gelatin); an excipient (e.g., starch or lactose), a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); or a flavoring agent (e.g., peppermint, methyl salicylate, or orange flavoring).

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The following examples are provided to illustrate the invention and are not to be construed as a limitation thereon.

PREPARATION EXAMPLES

Preparation Example 1

Preparation of (N-Fmoc-N'-$R_3$-Hydrazino)-Acetic Acid (1) Preparation of N-Fmoc-N'-Methyl Hydrazine

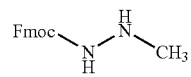

2 L, two-neck, round-bottomed-flask was fitted with a glass stopper and a calcium tube. A solution of methylhydrazine sulfate (20 g, 139 mmol, where $R_3$ is methyl) in THF (300 mL) was added and a solution of DiBoc (33 g, 153 mmol) in THF was added. Saturated sodium bicarbonate aqueous solution (500 mL) was added dropwise via addition funnel over 2 hours with vigorous stirring. After 6 hours, a solution of Fmoc-CI (39 g, 153 mmol) in THF was added slowly. The resulting suspension was stirred for 6 hours at 0° C. The mixture was extracted with ethyl acetate (EA, 500 mL) and the organic layer was retained. The solution was dried with sodium sulfate and evaporated in vacuo. The next step proceeded without purification.

A 1 L, two-necked, round-bottom-flask was fitted with a glass stopper and a calcium tube. A solution of the product from the previous step in MeOH (300 mL) was added and conc. HCl (30 mL, 12 N) was added slowly via addition funnel with magnetic stirring in ice water bath and stirred overnight. The mixture was extracted with EA (1000 mL) and the organic layer was retained. The solution was dried with sodium sulfate and evaporated in vacuo. The residue was purified by recrystallization with n-hexane and EA to give N-Fmoc-N'-methyl hydrazine (32.2 g, 83%). $^1$HNMR (DMSO-D6) δ 7.90~7.88 (d, J=6 Hz, 2H,), δ 7.73~7.70 (d, J=9 Hz, 2H,), 7.44~7.31 (m, 4H), 4.52~4.50 (d, J=6 Hz, 2H), 4.31~4.26 (t, J=6 Hz, 1H), 2.69 (s, 1H).

(2) Preparation of (N-Fmoc-N'-methyl-hydrazino)-acetic acid t-butyl ester

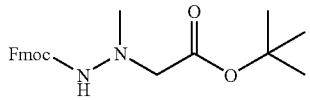

1 L, two-necked, round-bottom-flask was fitted with a glass stopper and reflux condenser connected to a calcium tube. A solution of N-Fmoc-N'-methyl hydrazine (20 g, 75 mmol) in toluene (300 mL) was added. A solution of t-butylbromo acetate (22 g, 111 mmol) in toluene (50 mL) was added slowly. Cs$_2$CO$_3$ (49 g, 149 mmol) was added slowly. NaI (11 g, 74 mmol) was added slowly with vigorous stirring. The reaction mixture was stirred at reflux temperature over 1 day. The product mixture was filtered and extracted with EA (500 mL). The solution was dried over sodium sulfate and evaporated in vacuo. The product was purified by chromatography with hexane:EA=2:1 solution to give (N-Fmoc-N'-methyl-hydrazino)-acetic acid t-butyl ester (19.8 g, 70%).

$^1$H-NMR (CDCl$_3$-d) δ 7.78~7.75 (d, J=9 Hz, 2H,), δ 7.61~7.59 (d, J=6 Hz, 2H,), 7.43~7.26 (m, 4H), 4.42~4.40 (d, J=6 Hz, 2H), 4.23 (b, 1H), 3.57 (s, 2H), 2.78 (s, 3H), 1.50 (s, 9H).

(3) Preparation of (N-Fmoc-N'-methyl-hydrazino)-acetic acid

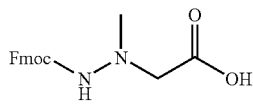

1 L, two-neck, round-bottomed-flask was fitted with a glass stopper and reflux condenser connected to a calcium tube. (N-Fmoc-N'-methyl-hydrazino)-acetic acid t-butyl ester (20 g, 52 mmol) was added. A solution of HCl (150 mL, 4 M solution in dioxane) was added slowly with vigorous stirring in an ice water bath. The reaction mixture was stirred at RT over 1 day. The solution was concentrated completely under reduced pressure at 40° C. A saturated aq. NaHCO$_3$ solution (100 mL) was added and the aqueous layer was washed with diethyl ether (100 mL). Conc. HCl was added dropwise slowly at 0° C. (pH 2-3). The mixture was extracted and the organic layer was retained (500 mL, MC). The solution was dried with sodium sulfate and evaporated in vacuo. The residue was purified by recrystallization with n-hexane and ethyl acetate to give (N-Fmoc-N'-methyl-hydrazino)-acetic acid (12 g, 72%). $^1$H-NMR (DMSO-d$_6$) d 12.38 (s, 1H), 8.56 (b, 1H), 7.89~7.86 (d, J=9 Hz, 2H,), 7.70~7.67 (d, J=9 Hz, 2H,), 7.43~7.29 (m, 4H), 4.29~4.27 (d, J=6 Hz, 2H), 4.25~4.20 (t, J=6 Hz, 1H), 3.47 (s, 2H), 2.56 (s, 3H).

Preparation Example 2

Preparation of (N-Moc-N'-R$_7$-Hydrazino)-Acetic Acid (1) Preparation of (N'-Methoxycarbonyl-hydrazino)-acetic acid ethyl ester

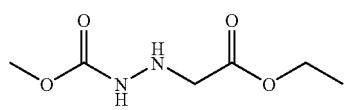

MOC-NH-NH$_2$ (50 g, 0.55 mol) was dissolved in DMF (300 ml), and then ethyl bromoacetate (68 ml, 0.555 mol) and potassium carbonate (77 g, 0.555 mol) were added to the reaction vessel. The mixture was warmed to 50° C. for 5 hours. After the reaction was completed, the mixture was filtered, and diluted with EtOAc, and washed with brine (3 times). The crude product was purified by column (eluent: Hex/EtOAc=4/1) to provide 72 of colorless oil.

(2) [N-R$_7$-N'-methoxycarbonyl-hydrazino]-acetic acid ethyl ester

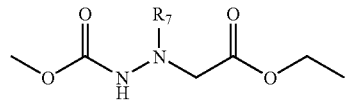

The ethyl ester (10 g, 0.05 mol), potassium carbonate (6.9 g, 0.05 mol), and R$_7$-bromide (14.1 g, 0.06 mol) were dissolved in DMF (200 ml), and The mixture was warmed to 50° C. for 5 hours. After the reaction was completed, the mixture was filtered, and diluted with EA, and washed with brine (3 times). The crude product was purified by Chromatography (eluent: Hex/EtOAc=4/1).

(3) [N-R$_7$-N'-methoxycarbonyl-hydrazino]-acetic acid

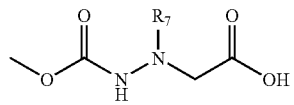

The alkylated ethyl ester (9.5 g, 0.03 mol) was dissolved in THF/water (1/1, ml), and added 2N NaOH (28.3 ml) solution at 0° C. The mixture was stirred at RT for 2 hours. After the starting ester was not detected on UV, the solution was diluted with EA, then separated. The aqueous layer was acidified to pH 3~4 by 1N HCl, and the compound was extracted by DCM (3 times). The combined organic layer was dried over MgSO4, and evaporated to give a yellow solid.

Preparation Example 3

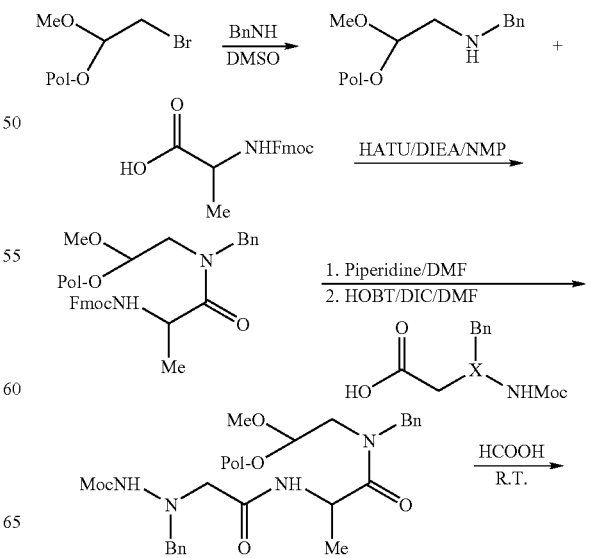

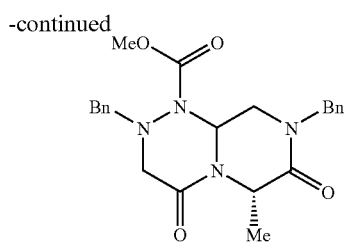

(1) Preparation of N^β-Moc-N^α-benzyl-hydrazinoglycine

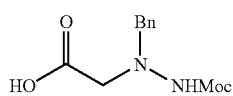

This compound was prepared according to literature procedure. (Cheguillaume et. al., *Synlett* 2000, 3, 331)

(2) Preparation of 1-Methoxycarbonyl-2,8-dibenzyl-6-methyl-4,7-dioxo-hexahydro-pyrazino[2,1-c][1,2,4]triazine Bromoacetal resin (60 mg, 0.98 mmol/g) and a solution of benzyl amine in DMSO (2.5 ml, 2 M) were placed in vial with screw cap. The reaction mixture was shaken at 60° C. using rotating oven [Robbins Scientific] for 12 hours. The resin was collected by filtration, and washed with DMF, then DCM, to provide a first component piece.

A solution of Fmoc-alanine (4 equiv., commercially available, the second component piece), HATU (PerSeptive Biosystems, 4 equiv.), and DIEA (4 equiv.) in NMP (Advanced ChemTech) was added to the resin. After the reaction mixture was shaken for 4 hours at room temperature, the resin was collected by filtration and washed with DMF, DCM, and then DMF.

To the resin was added 20% piperidine in DMF. After the reaction mixture was shaken for 8 min at room temperature, the resin was collected by filtration and washed with DMF, DCM, and then DMF.

A solution of N^β-Moc-N^α-benzyl-hydrazinoglycine (4 equiv., compound (3) in preparative example 2, where $R_7$ is benzyl, $3^{rd}$ component piece), HOBT [Advanced ChemTech] (4 equiv.), and DIC (4 equiv.) in DMF was added to the resin prepared above. After the reaction mixture was shaken for 3 hours at room temperature, the resin was collected by filtration and washed with DMF, DCM, and then MeOH. The resin was dried in vacuo at room temperature.

The resin was treated with formic acid (2.5 ml) for 18 hours at room temperature. After the resin was removed by filtration, the filtrate was condensed under reduced pressure to give the product as an oil. $^1$H-NMR (400 MHz, CDCl$_3$) d ppm; 1.51 (d, 3H), 2.99 (m, 1H), 3.39 (d, 1H), 3.69 (m, 1H), 3.75 (m, 1H), 3.82 (s, 3H), 4.02 (d, 1H), 4.24 (d, 1H), 4.39 (d, 1H), 4.75 (d, 1H), 5.14 (q, 1H), 5.58 (dd, 1H), 7.10-7.38 (m, 10H).

Preparation Example 4

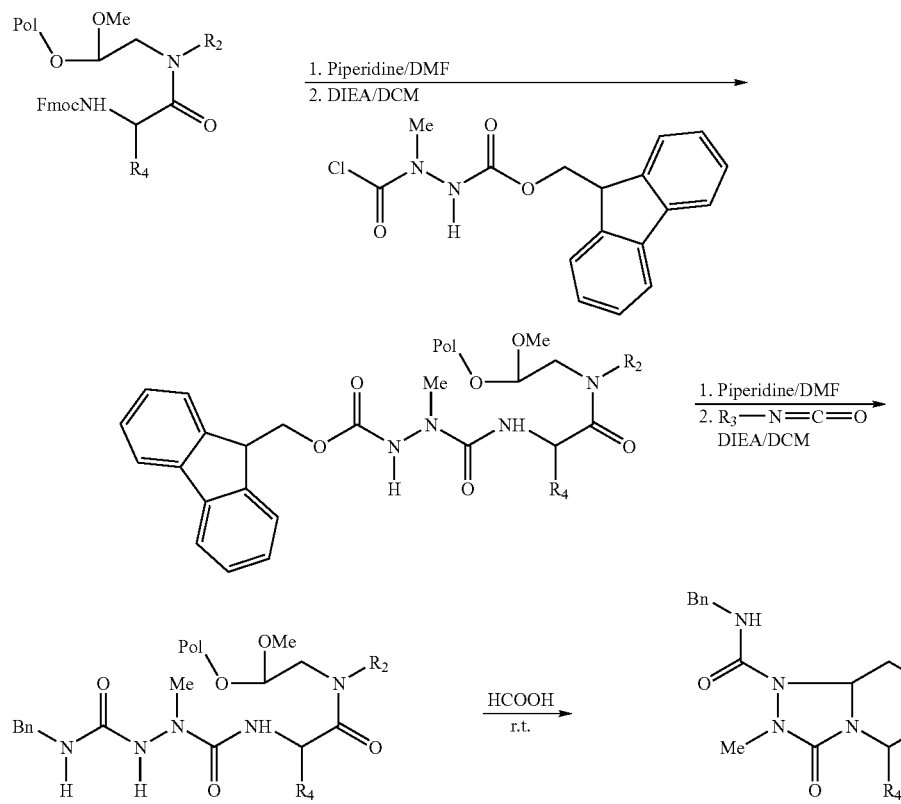

Example 2: $R_2$ = —Bn, $R_4$ = —CH$_3$
Example 3: $R_2$ = —CH$_3$, $R_4$ = —CH$_3$ (1) Preparation of N'-Fmoc-N-methyl-hydrazinocarbonyl chloride

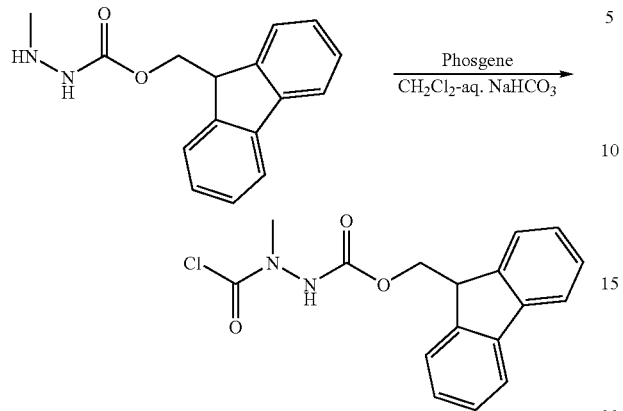

An ice-cooled biphasic mixture of N-methyl hydrazine carboxylic acid 9H-fluoren-9-ylmethyl ester (107 mg, 0.4 mmol) in 15 ml of $CH_2Cl_2$ and 15 ml of saturated aq. $NaHCO_3$ was rapidly stirred while 1.93 M phosgene in toluene (1.03 ml, 2 mmol) was added as a single portion. The reaction mixture was stirred for 30 min, the organic phase was collected, and the aqueous phase was extracted with $CH_2Cl_2$. The combined organic layers were dried over $MgSO_4$, filtered, and concentrated in vacuo to afford 128 mg (97%) of carbamoyl chloride as a foamy solid. [Caution: Phosgene vapor is highly toxic. Use it in a hood]. This product was used for the following solid phase synthesis without further purification.

(2) Preparation of 2,5-Dimethyl-7-benzyl-3,6-dioxo-hexahydro-[1,2,4]triazolo[4,5-a]pyrazine-1-carboxylic acid benzylamide Bromoacetal resin (30 mg, 0.98 mmol/g) and a solution of benzyl amine in DMSO (1.5 ml, 2 M) were placed in vial with screw cap. The reaction mixture was shaken at 60° C. using rotating oven [Robbins Scientific] for 12 hours. The resin was collected by filtration, and washed with DMF, then DCM, to provide the first component piece.

A solution of Fmoc-alanine (3 equiv., second component piece, commercially available), HATU (PerSeptive Biosystems, 3 equiv.), and DIEA (3 equiv.) in NMP (Advanced ChemTech) was added to the resin. After the reaction mixture was shaken for 4 hours at room temperature, the resin was collected by filtration and washed with DMF, DCM, and then DMF, to thereby add the second component piece to the first component piece.

To the resin was added 20% piperidine in DMF. After the reaction mixture was shaken for 8 min at room temperature, the resin was collected by filtration and washed with DMF, DCM, and then DMF.

A solution of N'-Fmoc-N-methyl-hydrazinocarbonyl chloride (combined third and fourth component pieces, 5 equiv.) obtained in the above step (1), DIEA (5 equiv.) in DCM was added to the resin prepared above. After the reaction mixture was shaken for 4 hours at room temperature, the resin was collected by filtration and washed with DMF, DCM, and DMF.

To the resin was added 20% piperidine in DMF (10 ml for 1 g of the resin). After the reaction mixture was shaken for 8 min at room temperature, the resin was collected by filtration and washed with DMF, DCM, and then DMF.

The resin was treated with a mixture of benzyl isocyanate (4 equiv.) and DIEA (4 equiv.) in DCM for 4 hours at room temperature. Then, the resin was collected by filtration and washed with DMF, DCM, and then MeOH. The resin was dried in vacuo at room temperature.

The resin was treated with formic acid for 14 hours at room temperature. After the resin was removed by filtration, the filtrate was condensed under reduced pressure to give the product as an oil.

$^1$H-NMR (400 MHz, $CDCl_3$) d ppm; 1.48 (d, 3H), 2.98 (s, 3H), 3.18 (m, 1H), 3.46 (m, 1H), 4.37-4.74 (m, 5H), 5.66 (dd, 1H), 6.18 (m, 1H), 7.10-7.40 (m, 10H).

Preparation Example 5

Preparation of 2,5,7-Trimethyl-3,6-Dioxo-Hexahydro-[1,2,4]Triazolo[4,5-A]Pyrazine-1-Carboxylic Acid Benzylamide The title compound is prepared according to the same procedure as described in Preparative Example 4, but reacting bromoacetal resin with a solution of methyl amine instead of benzyl amine. $^1$H-NMR (400 MHz, $CDCl_3$) d ppm; 1.48 (d, 3H), 2.99 (s, 3H), 3.03 (s, 3H), 3.38 (m, 1H), 3.53 (dd, 1H), 4.36 (dd, 1H), 4.52 (q, 1H), 4.59 (dd, 1H), 5.72 (dd, 1H), 6.19 (br.t, 1H), 7.10-7.38 (m, 5H).

Preparation Example 6

Preparation of 2-Methyl-5-(P-Hydroxyphenylmethyl)-7-Naphthylmethyl-3,6-Dioxo-Hexahydro-[1,2,4]Triazolo[4,5-A]Pyrazine-1-Carboxylic Acid Benzylamide Bromoacetal resin (30 mg, 0.98 mmol/g) and a solution of naphthylmethyl amine in DMSO (1.5 ml, 2 M) were placed in vial with screw cap. The reaction mixture was shaken at 60° C. using rotating oven [Robbins Scientific] for 12 hours. The resin was collected by filtration, and washed with DMF, then DCM to provide the first component piece.

A solution of Fmoc-Tyr(OBut)-OH (3 equiv.), HATU (PerSeptive Biosystems, 3 equiv.), and DIEA (3 equiv.) in NMP (Advanced ChemTech) was added to the resin. After the reaction mixture was shaken for 4 hours at room temperature, the resin was collected by filtration and washed with DMF, DCM, and then DMF, to thereby add the second component piece to the first component piece.

To the resin was added 20% piperidine in DMF. After the reaction mixture was shaken for 8 min at room temperature, the resin was collected by filtration and washed with DMF, DCM, and then DMF.

A solution of N'-Fmoc-N-methyl-hydrazinocarbonyl chloride (5 equiv.), DIEA (5 equiv.) in DCM was added to the resin prepared above. After the reaction mixture was shaken for 4 hours at room temperature, the resin was collected by filtration and washed with DMF, DCM, and DMF.

To the resin was added 20% piperidine in DMF (10 ml for 1 g of the resin). After the reaction mixture was shaken for 8 min at room temperature, the resin was collected by filtration and washed with DMF, DCM, and then DMF.

The resin was treated with a mixture of benzyl isocyanate (4 equiv.) and DIEA (4 equiv.) in DCM for 4 hours at room temperature. Then, the resin was collected by filteration and washed with DMF, DCM, and then MeOH. The resin was dried in vacuo at room temperature.

The resin was treated with formic acid for 14 hours at room temperature. After the resin was removed by filtration, the filtrate was condensed under reduced pressure to give the product as an oil.

$^1$H-NMR (400 MHz, CDCl$_3$) d ppm; 2.80-2.98 (m, 5H), 3.21-3.37 (m, 2H), 4.22-4.52 (m, 2H), 4.59 (t, 1H), 4.71 (d, 1H), 5.02 (dd, 1H), 5.35 (d, 1H), 5.51 (d, 1H), 6.66 (t, 2H), 6.94 (dd, 2H), 7.21-8.21 (m, 12H).

Preparation Example 7

Preparation of 2-Methyl-6-(P-Hydroxyphenylmethyl)-8-Naphthyl-4,7-Dioxo-Hexahydro-Pyrazino[2,1-C][1,2,4]Triazine-1-Carboxylic Acid Benzylamide Bromoacetal resin (60 mg, 0.98 mmol/g) and a solution of naphthyl amine in DMSO (2.5 ml, 2 M) were placed in vial with screw cap. The reaction mixture was shaken at 60° C. using rotating oven [Robbins Scientific] for 12 hours. The resin was collected by filtration, and washed with DMF, then DCM.

A solution of Fmoc-Tyr(OBut)-OH (4 equiv.), HATU [PerSeptive Biosystems] (4 equiv.), and DIEA (4 equiv.) in NMP (Advanced ChemTech) was added to the resin. After the reaction mixture was shaken for 4 hours at room temperature, the resin was collected by filtration and washed with DMF, DCM, and then DMF.

To the resin was added 20% piperidine in DMF. After the reaction mixture was shaken for 8 min at room temperature, the resin was collected by filtration and washed with DMF, DCM, and then DMF.

A solution of N$^\beta$-Fmoc-N$^\alpha$-benzyl-hyrazinoglycine (4 equiv.), HOBT [Advanced ChemTech] (4 equiv.), and DIC (4 equiv.) in DMF was added to the resin prepared above. After the reaction mixture was shaken for 3 hours at room temperature, the resin was collected by filtration and washed with DMF, and then DCM. To the resin was added 20% piperidine in DMF (10 ml for 1 g of the resin). After the reaction mixture was shaken for 8 min at room temperature, the resin was collected by filtration and washed with DMF, DCM, and then DMF.

The resin was treated with a mixture of benzyl isocyanate (4 equiv.) and DIEA (4 equiv.) in DCM for 4 hours at room temperature. Then, the resin was collected by filteration and washed with DMF, DCM, and then MeOH. After the resin was dried in vacuo at room temperature, the resin was treated with formic acid (2.5 ml) for 18 hours at room temperature. The resin was removed by filtration, and the filtrate was condensed under reduced pressure to give the product as an oil.

$^1$H-NMR (400 MHz, CDCl$_3$) d ppm; 2.73 (s, 3H), 3.13 (d, 1H), 3.21-3.38 (m, 3H), 3.55 (d, 1H), 3.75 (t, 1H), 4.22 (dd, 1H), 4.36 (dd, 1H), 4.79 (d, 1H), 5.22 (t, 1H), 5.47 (m, 2H), 6.68 (d, 2H), 6.99 (d, 2H), 7.21-8.21 (m, 12H); MS (m/z, ESI) 564.1 (MH$^+$) 586.3 (MNa$^+$).

EXAMPLES

Plasmids

Deletion constructs of CBP and p300 were expressed in the commercially available pTriEx-3 vector (Novagen, Madison, Wis.). Deletion series of murine CBP were generated by PCR from full-length mouse CBP plasmid, a generous gift from Dr. Richard Goodman at the Vollum Institute, Portland, Oreg. The amplified regions have a BamHI site at the 5'-end and a Not I at the 3'-end to allow for cloning in frame with the ATG of the expression vector pTriEx-3. For recognition and purification the plasmids were also cloned in frame with 6×-Histidine and Herpes Simplex Viral (HSV) tags at the COOH-terminus. The forward primer used to clone the C-terminally truncated constructs of CBP was 5'-GATATCTGAGCTCGTGGATCCGATGGCCGAGAACTTGCTG-3' (SEQ ID NO: 7). The reverse primers used for CBP-C1 (1-334), -C2 (1-634), -C3 (1-1594), -C4 (1-2062), -C5 (1-2623), -C6 (1-3094), -C7 (1-3694) were: C1: 5'-CGTG-TATACAGCTGTGCGGCC-GCGTTTGTACTGTTCG-GCTG-3' (SEQ ID NO: 8), C2: 5'-CGTGTATACAGCTGT-GCGGCCGCTCC-ATTCATGACTTGAGC-3' (SEQ ID NO: 9), C3: 5'-CGTGTATACAGCTGTGCGGC-CGCGCGTTTTT-CAGGGTCTGC-3' (SEQ ID NO: 10), C4: 5'-CGTGTATACAGCTGTGCGGCCGC AGCTGG-TAAAGC-TGGCTG-3' (SEQ ID NO: 11), C5: 5'-CGTG-TATACAGCTGTG CGGCCGCATGTTGGAGAGAGGGC-AT-3' (SEQ ID NO: 12), C6: 5'-CGTGTATA CAGCTGTGCGGCCGCAGAACCTTGTAAATCCTC-3' (SEQ ID NO: 13), C7: 5'-CGTGTATACAGCTGTGCGGC-CGCGCTGTAGTAGGCTGCATC-3' (SEQ ID NO: 14). The N-terminally truncated constructs of CBP were generated with the following reverse primer: 5'-GTATACAGCTGT-GCGGCCGCCAAACCCTCCACAA ACTTTTC-3' (SEQ ID NO: 15). The forward primers for CBP-C8 (4081-7324), -C9 (4534-7324), -C10 (5074-7324), -C11 (5674-7324), -C12 (6286-7324), -C13 (6754-7324) were: C8: 5'-GATATCTGAGCTCG-TGGATCCG-GAAGCTGGGGAGGTTT TT-3' (SEQ ID NO: 16), C9: 5'-GATATCTGAGCTCGTGGAT-CCGAAGAAGATGC TGGACAAG-3' (SEQ ID NO: 17), C10: 5'-GATATCT-GAGCTCGTGGATCCGTCC AAATGGTCCACTCTG-3' (SEQ ID NO: 18), C11: 5'-GATATCTGAGCTCGTGGAT CCGTCTCCTACCTCAGCACCA-3' (SEQ ID NO: 19), C12: 5'-GATATCTGAGCTC GTGGATCCGAACATCCT-TAA-ATCAAAC-3' (SEQ ID NO: 20), C13: 5'-GATATCT GAGCCGTGGATCCGCAGCAGCAACGCATG-CAA-3' (SEQ ID NO: 21). Using the forward primer of the C-terminal truncated constructs and the reverse primer of the N-terminal truncated constructs, the full-length mouse CBP was amplified and cloned into the pTriEx-3 vector. CBP (Δ1-111+NLS) was generated by PCR of the full-length CBP using the following forward, PAGE purified, primer containing the BamH I site upstream of the NLS sequence (underlined) of CBP: 5'-ATCTGAGCTCGTGGATCCG <u>GGACCGCCCAACCCCAAACGAGCCAAACTCCA</u> GCCGAACAGTACAAACATGGCCAGCTTA-3' (SEQ ID NO: 22) and the reverse primer used was the primer used to generate the N-terminally truncated constructs of CBP, mentioned above. The insert was cloned into the BamH I-Not I sites of pTriEx-3 plasmid.

Deletion constructs of p300 were generated by PCR of the human p300 plasmid (CMVβ-p300-CHA) a generous gift of Dr. David Livingston (Harvard, Mass.). The PCR products were cloned into the Hind III-Not I site of the pTriEx-3 vector. The forward primer for the C-terminal truncated p300 constructs was: 5'-GACGGTACCGGTTCGAAGCTTA-TGGC-CGAGAATGTGGT-G-3' (SEQ ID NO: 23). The reverse primers for: p300-P1 (1-334), p300-P2 (1-634) and p300-P3 (1-1054) are as follows: P1: 5'-CGTGTATACAGCTGT-GCGGCCGC-CAAACCTAATC CAGGACT-3' (SEQ ID NO: 24), P2: CGTG-TATACAGCTGTGCGGCCGCGT-TGC CAGCACTTCCCAT-3' (SEQ ID NO: 25), P3: CGTG-TATACA-GCTGTCGGCCG     CGGCCTGTTCCCG-GCGCTG-3' (SEQ ID NO: 26).

β-catenin/TCF reporter plasmid was generated by inserting 4 tandem TCF4 binding sites (CCAACCTTTGATCT-TACCCCCTTTGATCTTACCCCCTTTGATCAG-GAAT-TCGGTTGGAAACTAGAATGGGGGAAACTAGAATGG-GGGAAACTAGTCCTTAAG) (SEQ ID NO: 27) in Xho I-Kpn I sites of pGL3 plasmid (Promega) upstream of a SV40 promoter driving the expression of the downstream luciferase gene.

All primers were purchased from Integrated DNA Technologies, Inc. (Coralville, Iowa). Restriction enzymes used for cloning are underlined and were purchased from New England Biolabs, Beverly, Mass.

Cell Culture

The human colon carcinoma cell lines SW480 and HCT116, and normal colonocytes CCD18Co (ATCC, Manassas, Va.) were grown in DMEM (Invitrogen Gibco-BRL, Baltimore, Md.) supplemented with 10% fetal calf serum in a 5% $CO_2$ atmosphere at 37° C.

Transfection

Exponentially growing SW480 and HCT116 cells ($10^5$) were cultured in 24-well plates or 100-mm dishes and transfected with 0.5 µg of β-catenin/TCF reporter and increasing concentrations of the effector plasmids or 10 µg of the expression vectors, respectively. Cells were transfected with FuGENE6 (Roche Molecular Biochemicals, Indianapolis, Ind.) or Superfect (Qiagen, Valencia, Calif.) as indicated. Nuclear extracts were made according to the procedure described in the NE-PER kit (Pierce Biotechnology, Rockford, Ill.).

Luciferase Assays

Luciferase assays for the various groups were performed on 20 µl of cell lysate using the dual luciferase assay system (Promega), 16-24 hrs post transfection, as indicated. Increasing concentrations of empty expression vector, pTriEx-3, was used for normalization.

Soft Agar Assays

The soft agar colony formation assay was conducted with SW480 cells by some modification of the procedure previously described (Moody et al., "A vasoactive intestinal peptide antagonist inhibits non-small cell lung cancer growth," *Proc. Natl. Acad. Sci. USA*. 90:4345-49 (1993)).

Each well (35 mm) of a 6-well plate (Nalge Nunc International, Roskide, Denmark) was coated with 1 ml of 0.8% bottom agar in DMEM medium containing 10% fetal bovine serum. After it was solidified, 1 ml of DMEM medium containing 0.4% top agar, 10% fetal bovine serum, compound doubly concentrated, and 5,000 single viable cells was added to each well. The cultures were incubated at 37° C. in humidified 5% $CO_2$ incubator. Colonies in soft agar were monitored daily and photographed after incubation for 8 days. Colonies >60 µm in diameter were counted.

Immunoprecipitation

Cells were lysed with lysis buffer containing, 20 mM Hepes pH 7.9, 100 mM NaCl, 0.5 mM EDTA, 0.5% Nonidet P-40, 6 mM $MgCl_2$, 5 mM 2-Mercaptoethanol, and 1 tablet of the Complete™ protease inhibitor cocktail (Roche Molecular Biochemicals) for 30 minutes on ice and were cleared by centrifugation. Whole cell lysates were incubated with the specified antibodies, for CBP-C1, A-22 antibody from Santa Cruz Biotechnology, Inc. for p300-P1, N-15 antibody (Santa Cruz Biotechnology, Inc. Santa Cruz, Calif.), and for full-length endogenous β-catenin, a monoclonal antibody (Transduction Laboratories, Lexington, Ky.) pre-bound to Protein A-agarose beads (Pierce, Rockford, Ill.) for 1 hr at room temperature. The immune complexes were washed several times in HBS (100-150 mM NaCl, as indicated, 10 mM Hepes pH 7.9, 5 mM 2-Mercaptoethanol and 1 tablet of the Complete™ protease inhibitor cocktail) and were subjected to western blotting, see below. The beads were then washed seven times with buffer containing (20 mM Hepes pH 7.9, 500 mM NaCl, and 5 mM 2-mercaptoethanol containing 1 tablet of the Complete™ protease inhibitor cocktail).

Pull-down Assays 25-100 µM of the biotinylated COMPOUND 2 was bound overnight at room temperature to 100 µl of a 50% slurry of streptavidin-agarose beads (Amersham Pharmacia Biotech, Arlington Heights, Ill.) in buffer containing 50% DMSO and 50% protein binding buffer, PBB, (20 mM Hepes pH 7.9, 20% glycerol, 0.5 mM EDTA, 60 mM NaCl, 6 mM $MgCl_2$, 0.1% Nonidet P-40, 5 mM 2-Mercaptoethanol, and 1 tablet of the Complete™ protease inhibitor cocktail). The beads were washed 3× with PBB to remove unbound COMPOUND 2. 100-200 µl of whole cell lysates containing overexpressed plasmids, see immunoprecipitation section, were incubated with the beads for 3-4 hrs at room temperature or overnight at 4° C. The beads were then washed 3× in the PBB buffer and then the eluted proteins were subjected to SDS-PAGE electrophoresis and Western blotting, see below. In the competition assays, excess COMPOUND 1, as indicated for each experiment, was preincubated with the lysates for 1 hour at room temperature.

ChIP Assay

Formaldehyde cross-linking and chromatin immunoprecipitation assays of SW480 cells were performed as described previously (Barlev et al., "Acetylation of p53 activates transcription through recruitment of coactivators/histone acetyltransferases," *Mol. Cell* 8:1243-54 (2001); El-Osta et al., "Analysis of chromatin-immunopurified MeCP2-associated fragments," *Biochem. Biophys. Res. Commun.* 289:733-37 (2001); Shang et al., "Formation of the androgen receptor transcription Complex," *Mol. Cell* 9:601-10 (2002)). Primers used for PCR of the c-myc and cyclin D1 promoters are as follows: c-myc forward primer: 5'-TGGTAGGCGCGCG-TAGTTA-3' (SEQ ID NO: 28) and reverse primer: 5'-GGGCGGAGATTAGCGAGAG-3' (SEQ ID NO: 29). Cyclin D1 forward primer: 5'-TGCTTAACAACA-GTAACGT-3' (SEQ ID NO: 30) and the reverse primer: 5'-GGGGCTCTTCCTGGGCAGC-3' (SEQ ID NO: 31). These ChIP primers were designed about 20 to 30 base pairs downstream of the TCF4 binding domain within the promoter region near the transcription start site. The PCR products are approximately 200 base pairs in size. Anti-CBP, AC-26, antibody was a kind gift from Dr. David Livingston.

Western Blot Assay

Immune complexes, from above, were separated on SDS-PAGE followed by transfer to immobilon-P membranes (PVDF) from (Millipore, Bedford, Mass.). The membranes were blocked with 5% nonfat dried milk in TBST (15 mM Tris/HCl, pH 7.4, 0.9% NaCl, and 0.05% Tween 20) followed by blotting with the specified antibodies. Anti-His antibody from Qiagen Inc. was used for detection of the proteins made in the pTriEx-3. Secondary antibodies conjugated to horseradish peroxide (Santa Cruz Biotechnology Inc.) were used for detection. Immunoblots were analyzed using an ECL detection kit (Amersham Pharmacia Biotech).

Immunofluorescence

Immunofluorescence was used to examine the localization of CBP and β-catenin in SW480 and HCT116 cells treated with COMPOUND 1 (25 µM) or control (0.5% DMSO). Cells at log phase were seeded and after 24 hours, the cells were treated with COMPOUND 1 or control. 24 hours post treatment, cells were fixed. The coverslips were incubated with antibodies raised against CBP (A-22) (Santa Cruz Biotechnology) and β-catenin (Transduction Laboratories), respectively. The slides were examined using a Nikon PCM 2000 Laser Scanning Confocal Microscope after the secondary antibodies conjugated to either FITC or TRITC (Jackson ImmunoResearch, Westgrove, Pa.) were applied.

Flow Cytometric Analysis (FACS)

For FACS analysis, approx. $5 \times 10^6$ cells from PNRI-treated or vehicle-treated were fixed with 70% chilled ethanol and stored at $-20°$ C. for at least 30 minutes. The cells were washed once with 1×PBS and incubated with propidium iodine (PI) solution (85 μg/ml propidium iodine, 0.1% Nonidet P-40, 10 mg/ml RNAse) for 30 minutes at room temperature. 10,000 stained cells for each sample were acquired using Beckman Coulter EPICS XL-MCL Flow Cytometry and the percentage of cells in different phase of the cell cycle was determined by Expo32 ADC software (Coulter Corporation, Miami, Fla., 33196).

Protein Purification

The CBP (1-111) and p300 (1-111) were expressed as fusion proteins with 6×-His tags and were affinity-purified from bacterial lysates using their 6×-His-tags. Transformed bacterial pellets (1 L cultures) were resuspended in 5-10 mls of lysis buffer (20 mM Hepes pH 7.9, 150 mM NaCl, 0.1% Nonidet P-40, 5 mM 2-mercaptoethanol and 1 tablet of the Complete™ protease inhibitor cocktail). Cells were lysed by sonication. The cleared lysates were incubated for 1 hr at 4° C. with 500 μl of Ni-NTA-agarose beads (Qiagen). Bound proteins were eluted with 500 μl of elution buffer (20 mM Hepes pH 7.9 and 150 mM NaCl, 1 tablet of Complete™ protease inhibitor cocktail, 5 mM 2-mercaptoethanol and 250 mM imidazole). The eluted proteins were frozen in small aliquots.

Real Time Reverse Transcription-PCR Analysis

The RNeasy Midi Kit (Qiagen) was used for RNA extraction and Real Time RT-PCR was performed according to the protocol provided with the SYBR Green PCR Master Mix Kit (Perkin Elmer Biosystems, Shelton, Conn.). The primers used for cyclin D1, axin2, hnkd, c-myc, c-jun, and fra-1 amplifications were: cyclin D1 forward primer:5'-AGATC-GAAGC-CCTGCTG-3' (SEQ ID NO: 32) reverse primer: 5'-AGGGGGAAAGAGCAAAGG-3' (SEQ ID NO: 33) leading to a product size of approximately 300 bp; axin2 forward primer: 5'-GTGTGAGGTCCAC GGAAA-CT-3' (SEQ ID NO: 34) and reverse primer: 5'-CTCGGGAAATGAGGTA-GAGA-3' (SEQ ID NO: 35); hnkd forward primer: 5'-CTG-GCTGCTGCTACCACCA TTGCGT-3' (SEQ ID NO: 36) and the reverse primer: 5'-CCAGGCCCAAATTGGG ACGT-3' (SEQ ID NO: 37); c-myc forward primer: 5'-GAA-GAAATTCGAGCTG CTGC-3' (SEQ ID NO: 38) and reverse primer: 5'-CACATACAGTCCTGGATGAT-G-3' (SEQ ID NO: 39); c-jun forward primer: 5'-AGATGCCCG-GCGAGACACCG-3' (SEQ ID NO: 40) and reverse primer: 5'-AGCCCCCGACGGTCTCTTT-3' (SEQ ID NO: 41); fra-1 forward primer: 5'-ACC-CCGGCCAGGAG-TCATC-CGGGCCC-3' (SEQ ID NO: 42) and reverse primer: 5'-AG-GCGCCTCACAAAGCGAGGAGGG-TT-3' (SEQ ID NO: 43). β-actin was used for normalization. The primers for, β-actin were: forward primer: 5'-ATCTGGCACCACACCT-TCTACMTGAGCTGCG-3' (SEQ ID NO: 44) and reverse primer 5'-CGTCATACTCCTCCTTGCYGATCCACA TCTGC-3' (SEQ ID NO: 45). Each primer set was amplified at 95° C. for 10 min and 40 cycles of 95° C. for 15 sec and 60° C. for 1 min.

Caspase-3 Activity Assay

SW480, HCT116, and CCD18Co cells were plated at $10^5$ cells per well (96-well plates) for 24 hours prior to treatment. 25 μM of COMPOUND 1 or control (0.5% DMSO) was added to each well. 24 hours post treatment, cells were lysed and caspase activity was measured using a caspase-3/7 activity kit (Apo-One Homogeneous caspase-3/7 assay, #G77905, Promega). Relative fluorescence units (RFU) were obtained by subtracting the unit values of the blank (control, without cells) from the experimental measured values.

Table 1 shows the results of Quantitative Real Time Reverse Transcription-PCR (RT-PCR) analysis of SW480 cells treated for 4, 8, or 24 hours with either COMPOUND 1 (25μ) or control (0.5% DMSO). 1 μg of mRNA, for each time point, was subjected to Real Time RT-PCR. Expression level of endogenous cyclin D1, c-myc, fibronectin, hnkd, axin2, c-jun, and BMP-4 were measured relative to β-actin. Quantitation of The ΔCycle of Threshold (CT) values was determined by subtracting the average values of each set by the corresponding average values obtained for β-actin. All experiments were performed in duplicate.

Compound 1 Antagonizes β-catenin/TCF Transcription by Targeting CBP

Due to mutations in APC, SW480 colon carcinoma cells exhibit constitutive translocation of β-catenin to the nucleus, and, thus, high basal β-catenin/TCF transcription, as assessed by the TOPFLASH reporter system (Korinek et al., "Constitutive transcriptional activation by a beta-catenin-Tcf complex in APC-/- colon carcinoma," *Science* 275:1784-87 (1997)). A related reporter was used to screen a secondary structure-templated small molecule library (Ogbu et al., "Highly efficient and versatile synthesis of libraries of constrained b-strand mimetics," *Bioorg. Med. Chem. Lett.* 8:2321-26 (1998); Eguchi et al., "Solid-phase synthesis and structural analysis of Bicyclic β-Turn mimetics incorporating functionality at the i to i+3 positions," *Amer. Chem. Soci.* 102:22031-32 (1999)) for inhibitors of β-catenin/TCF-mediated transcription. From the initial screen, we selected COMPOUND 1 (FIG. 1A) which had an $IC_{50}$ of 5 μM (FIG. 1B) and very good selectivity versus a number of other CBP-dependent reporters including NFAT (FIG. 1C), CRE, and AP-1 (data not shown). COMPOUND 1 displayed similar activity in HCT116 cells which are defective in β-catenin phosphorylation sites but express wild-type APC (data not shown).

Figure 1A:
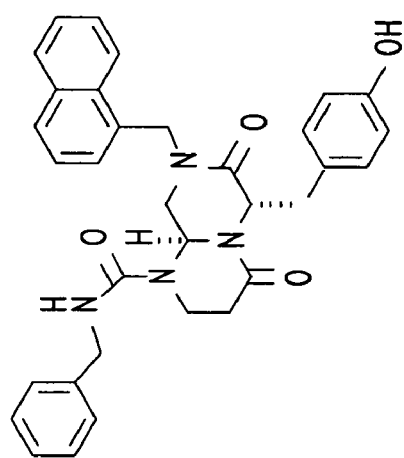
FIG. 1. COMPOUND 1 inhibits β-catenin/TCF transcription.
- A(i) and A(ii). Structures of COMPOUND 1, COMPOUND 2, COMPOUND 3, COMPOUND 4, and COMPOUND 5.
- B(i) and B(ii). COMPOUND 1 selectively inhibits a β-catenin/TCF reporter gene construct with an $IC_{50}$ of 5 μM. SW480 cells ($10^5$), (FIG. 1B(i)), were transfected with β-catenin/TCF luciferase construct. Cells were treated with COMPOUND 1 (1-64 μM). 24 hours post treatment lysates were prepared and subjected to dual luciferase assay. The data is represented in different form in FIG. 1B(ii).
- C. COMPOUND 1 has no effect on NFAT reporter construct. Stably transfected Jurkat cells, right panel, with an NFAT reporter construct, were stimulated with PMA (10 ng/ml)/Ionomycin (1 μg/ml), and treated with COMPOUND 1 (0.781-50 μM). 24 hours post treatment lysates were prepared and subjected to dual luciferase assay. All experiments were performed in duplicate and the values plotted as means +/−standard deviation.
- D. CBP is the molecular target of COMPOUND 1. Nuclear extracts of SW480 cells were incubated with streptavidin-agarose beads coated with COMPOUND 2 (25 μM). Beads were washed 3 times and the eluted were subjected to gel electrophoresis and immunoblotting, with anti-CBP antibodies. The arrow points to the band corresponding in size and by immunoreactivity to CBP.
- E. $^{14}$C-labeled-COMPOUND 1 binds to CBP. COMPOUND 1 was prepared by incorporation of $^{14}$C-labeled tyrosine. SW480 cells were transfected with vectors expressing full-length Xenopus laevis β-catenin (2.2 μg) or full-length mouse CBP (1.1 μg). 50 μg of nuclear lysate (NE-PER kit, Pierce) was treated with 20 μM $^{14}$C-labeled-COMPOUND 1 ($7.16 \times 10^4$ CPM) either with DMSO (0.5%), or with 100 μM and 200 μM of cold COMPOUND 1. The lysates were desalted using G-25 1 cc columns (Pharmacia) to remove the unbound $^{14}$C-labeled-COMPOUND 1, and $^{14}$C-labeled-COMPOUND 1 incorporation was measured.
Figure 1A:
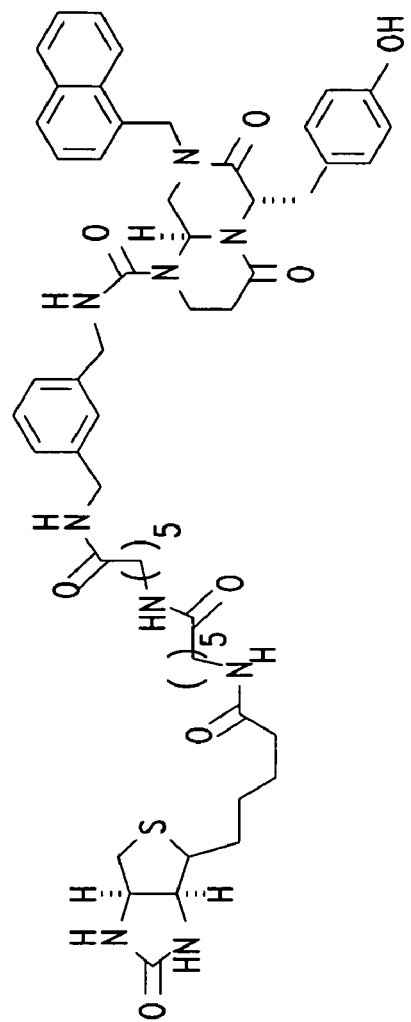
Figure 1C:
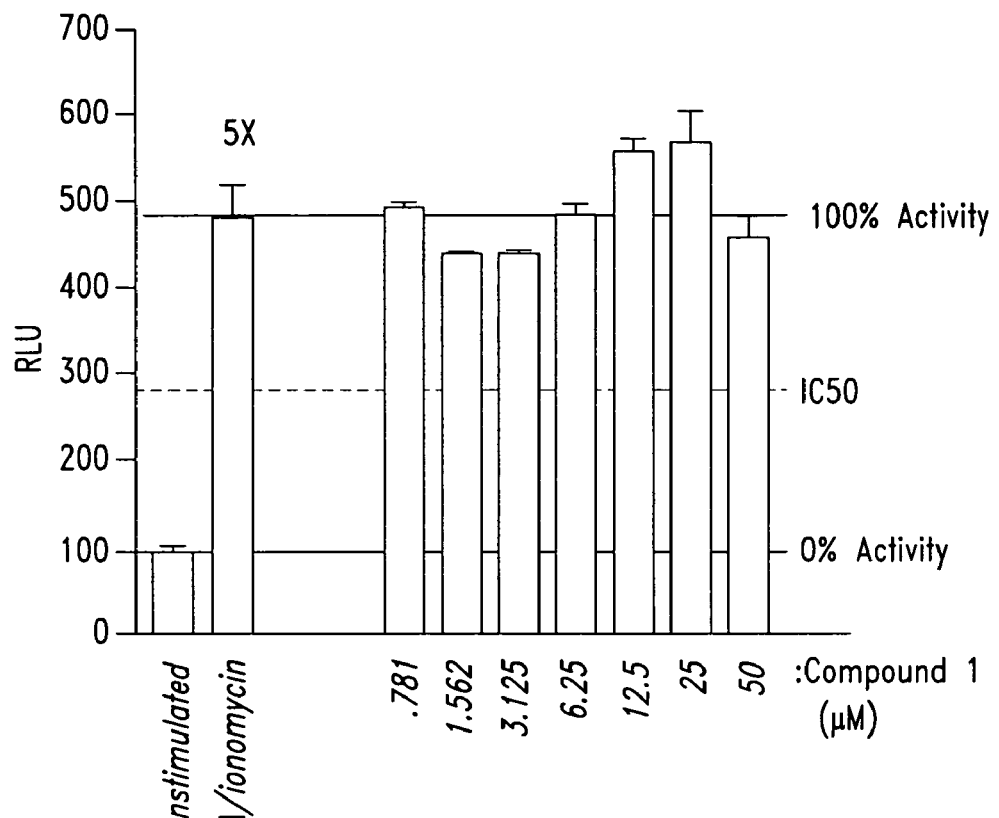
Figure 1D:
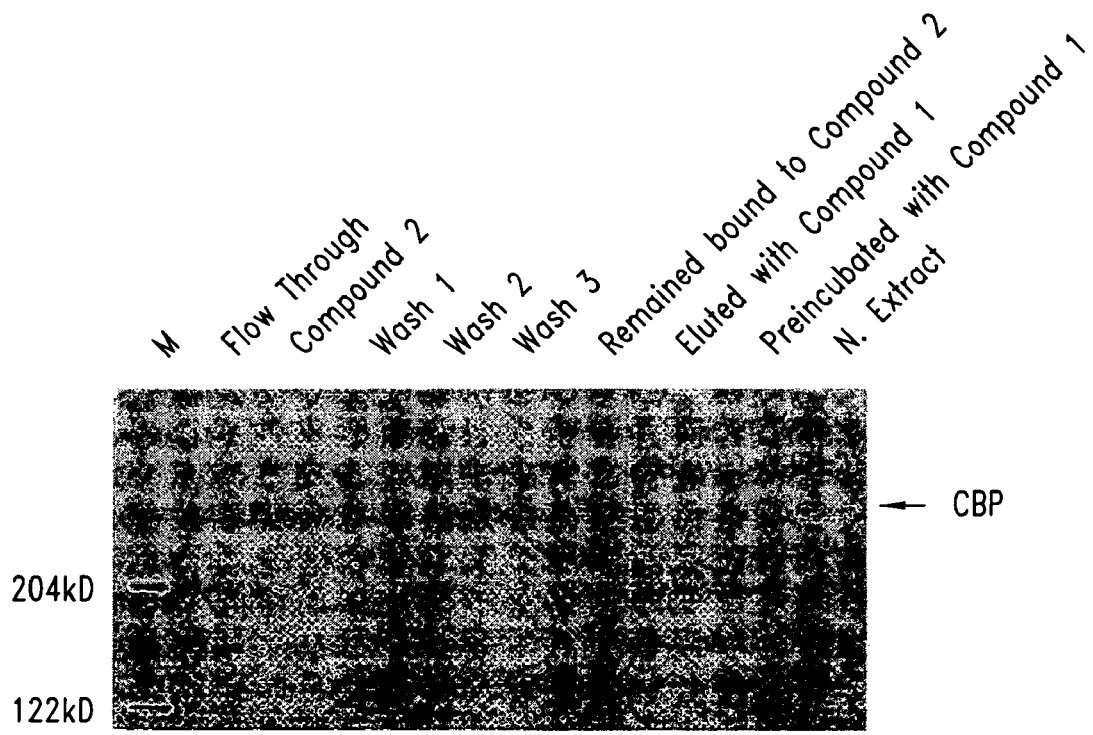

In order to determine the molecular target(s) of COMPOUND 1, we derivatized it for use as an affinity reagent, to provide COMPOUND 2 (FIG. 1A). Nuclear extracts were prepared from SW480 cells after pretreatment with COMPOUND 1 or vehicle, and then incubated with COMPOUND 2. The complexes were then separated on streptavidin-agarose beads and subjected to gel electrophoresis. The major band retained from the nuclear extract of SW480 cells on the COMPOUND 2 affinity column had an apparent molecular weight of 225 KDa and was identified by immunoblotting as the CREB Binding Protein (CBP) (FIG. 1D). COMPOUND 1 specifically eluted CBP bound to COMPOUND 2 (FIG. 1D, compare lane 7 to 8) and preincubation of the nuclear extracts with COMPOUND 1 (20 μM) prior to affinity chromatography blocked the binding of CBP (FIG. 1D, lane 9). The antibody used was specific for CBP and does not cross react with p300. Accordingly, these data indicate that COMPOUND 1 binds CBP.

Figure 1E:
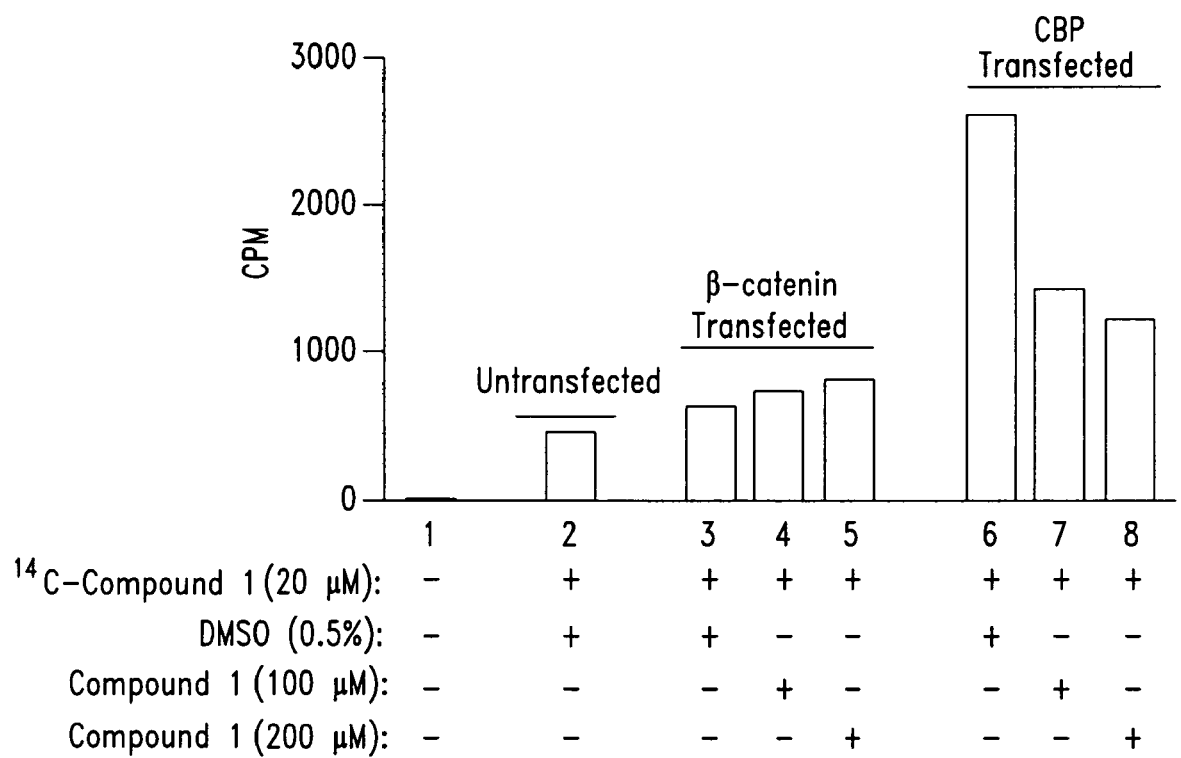

A series of further investigations were performed to further validate that COMPOUND 1 binds CBP. A $^{14}$C-labeled version of COMPOUND 1 was synthesized by incorporating $^{14}$C-labeled tyrosine in the synthesis. Nuclear lysates of SW480 cells, untransfected or transfected with either β-catenin or CBP expression vectors, were treated with $^{14}$C-labeled COMPOUND 1 with either DMSO or cold COMPOUND 1 overnight. Cell lysates were then desalted using G-25 columns to remove the unbound $^{14}$C-labeled COMPOUND 1 and the incorporation of radioactivity was measured. As seen in FIG. 1E, the nuclear lysates transfected with CBP had approximately 4-6 fold increased incorporation of the $^{14}$C-labeled COMPOUND 1 compared to the control (FIG. 1E, compare lane 2 to 6), which was competed away by cold COMPOUND 1 in a dose dependent fashion (FIG. 1E, compare lane 6 to 7 & 8).

Based on this evidence, it is concluded that COMPOUND 1 binds CBP. Accordingly, one aspect of the invention provides a method comprising combining a composition comprising CBP with an agent, where the agent binds to CBP. The binding to CBP interferes with any other binding reaction that CBP would otherwise undergo. Thus, the present invention provides a method for treating a subject by binding to CBP, comprising administering an effective amount of an agent to a subject in need thereof.

Compound 1 Specifically Interacts with the First 111 Amino Acids of CBP

The biotinylated analog, COMPOUND 2 (FIG. 1A) was used to delineate the minimal region of CBP necessary for binding COMPOUND 1. Cell lysates that contained overexpressed fragments of CBP (FIG. 2B, upper panel) were incubated with streptavidin-agarose beads prebound with COMPOUND 2 for several hours. The bound proteins were then eluted from the beads and subjected to gel electrophoresis and immunoblotting using anti-His antibodies to detect the bound CBP fragment(s). As shown (FIG. 2B, lower panel), the minimal region to which COMPOUND 2 specifically bound was amino acids 1-111 at the NH$_2$-terminus of CBP (compare lanes 2, 3, and 4 to the others). As anticipated from the co-immunoprecipitation experiments, no binding was detected with any of the p300 fragments overexpressed in SW480 cell (data not shown, see below). When CBP (1-111), CBP (1-211), and CBP (1-351) along with p300 (1-111), p300 (1-211) and p300 (1-351) were overexpressed in SW480 cells (FIG. 2C, lower panel), excess COMPOUND 1, strongly competed away the binding of the CBP fragments (FIG. 2C, upper panel, compare lanes 4-6 to 7-9) but failed to have any effect on the binding of the p300 fragments (FIG. 2C, compare lanes 10-12 to 13-15). Accordingly, it is seen that COMPOUND 1 binds the first 111 amino acids of CBP but not the related protein, p300.

Figure 2A:
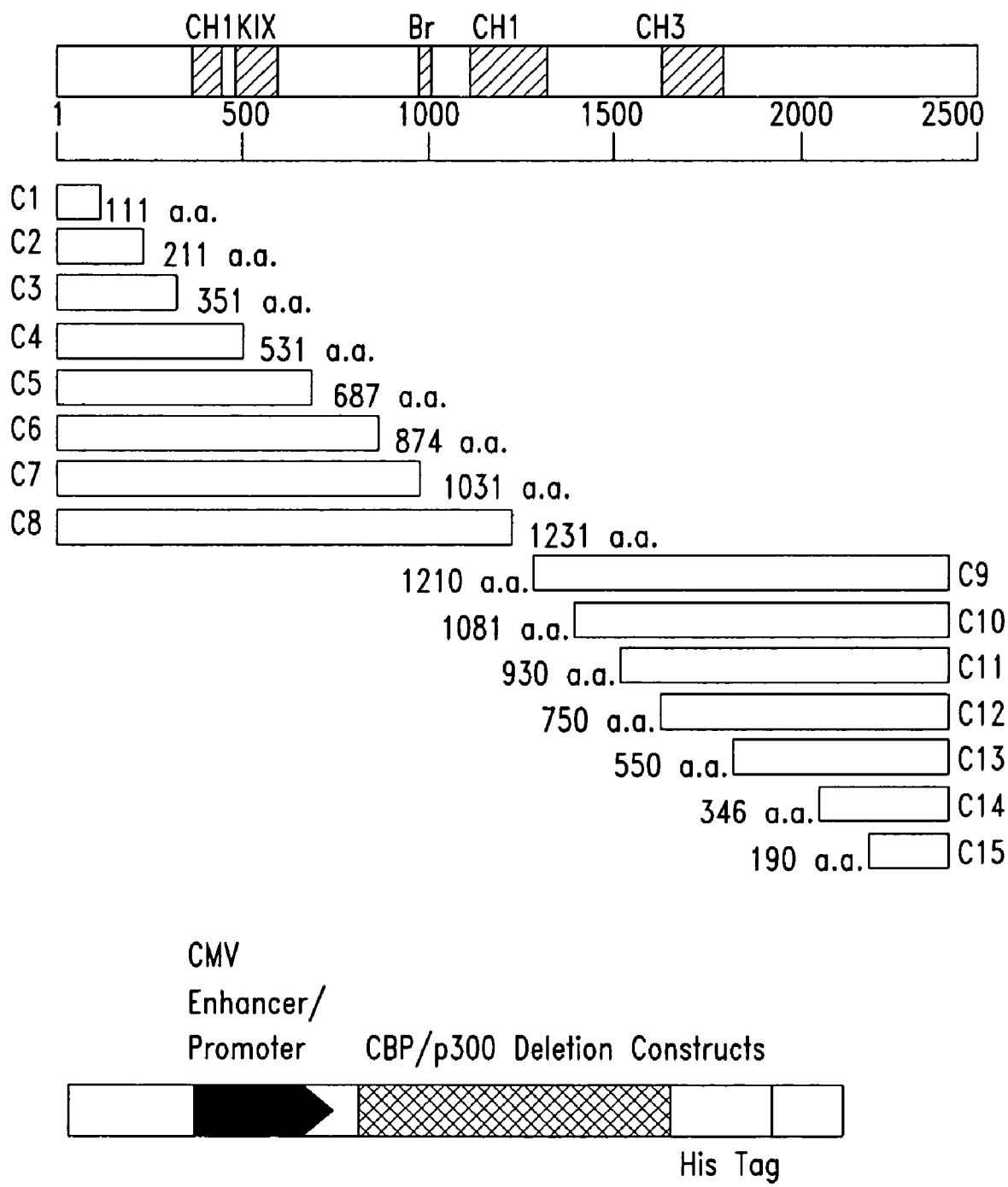
FIG. 2. The first 111 amino acids of CBP, but not p300, specifically bind COMPOUND 1.
- A. Schematic representation of the wild-type and deletion constructs for CBP.
- B. CBP (1-111) contains the minimal binding domain of COMPOUND 1. Expression levels of CBP deletion constructs in SW480 cells are shown (upper panel). 10 μg of total protein was subjected to gel electrophoresis and subjected to immunoblotting using anti-His antibodies. Whole cell lysates of SW480 cells expressing CBP deletion constructs were bound to streptavidin-agarose beads coated with 100 μM of COMPOUND 2. The bound fractions were subjected to gel electrophoresis and immunoblotting using anti-His antibodies (lower panel). Arrows point to constructs which remained bound to COMPOUND 2 coated beads.
- C. Excess COMPOUND 1 competes away CBP (1-111) but not p300 (1-111). CBP deletion constructs, CBP(1-111),CBP (1-211), and CBP (1-351) and p300 deletion constructs, p300 (1-111), p300 (1-211), and p300 (1-351) were transfected into SW480 cells. Whole cell lysates were incubated with streptavidin-agarose beads or streptavidin-agarose beads coated with 100 μM COMPOUND 2 (lower panel). The binding of CBP constructs (1-111,1-211, and 1-351) and p300 constructs (1-111,1-211, and 1-351) to the beads was challenged with excess COMPOUND 1 (150 μM).
- D. CBP (1-111) binds to COMPOUND 1 in a phosphorylation independent manner. CBP (1-111) or p300 (1-111) was expressed in E. coli and purified by Ni-NTA-agarose (Commassie blue stained gel). CBP (1-111) is shown (upper, right). 1 and 3 μl of purified proteins were subjected to immunoblotting using anti-His antibodies. Arrows point to recombinant proteins recognized by their appropriate antibodies. Increasing amounts of purified CBP (1-111) (0.5, 1 and 3 μl) and p300 (1-111) (1, 3, and 5 μl) were incubated with streptavidin-agarose beads coated with 100 μM of COMPOUND 2. The beads were washed and the eluted proteins were subjected to gel electrophoresis followed by immunoblotting using anti-His antibodies. Arrows point to the proteins on the PVDF membranes. The specific binding interactions were challenged using excess COMPOUND 1 (300 μM).
- E. The Δ1-111+NLS construct of CBP is incapable of rescuing β-catenin/TCF transcription inhibited by COMPOUND 1. SW480 cells were transfected with (0.1-1) μg of the expression vectors expressing either full length or CBP (Δ1-111+NLS). 24 hours post transfection cells were treated with COMPOUND 1 (25 μM) or control (0.5% DMSO). 24 hours post treatment lysates were prepared and subjected to dual luciferase assay.
Figure 2B:
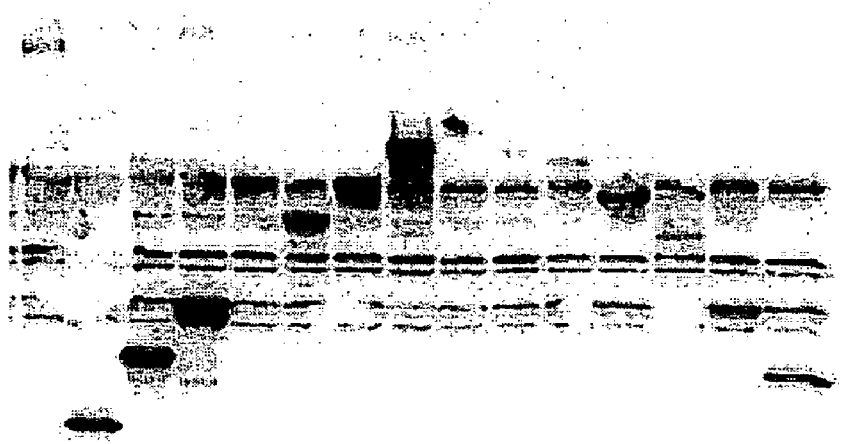
Figure 2B:
Figure 2C:
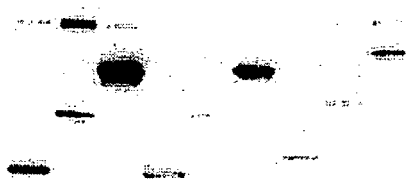
Figure 2C:
Figure 2D:
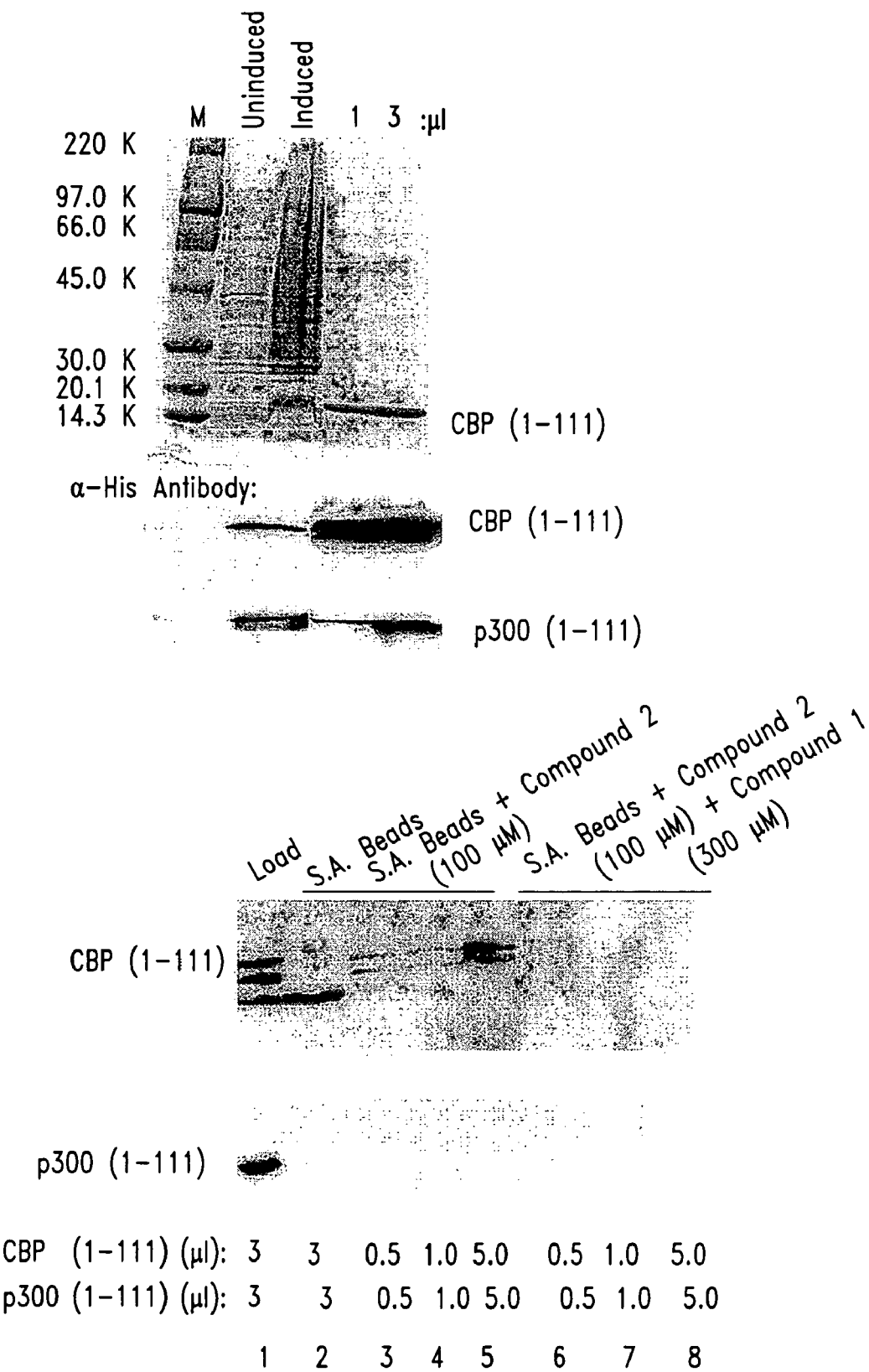

To exclude the possibility of an indirect association between CBP and COMPOUND 1 mediated by another cellular component and to test for direct binding we affinity purified CBP (1-111) and p300 (1-111) using 6x-His-tagged *E. coli* expressed proteins (FIG. 2D, right). Using COMPOUND 2 bound to streptavidin-agarose beads, we demonstrated specific binding of CBP (1-111) but not p300 (1-111) to COMPOUND 2, which was competed away by excess COMPOUND 1 (FIG. 2D, right, compare lanes, 3-5 to 6-8). This data confirms the direct association between CBP (1-111) and COMPOUND 1, in vitro. Since COMPOUND 1 bound to CBP expressed in *E. coli*, this reduces the likelihood that the CBP needs to be phosphorylated by mammalian kinases in order to bind COMPOUND 1.

Figure 2E:
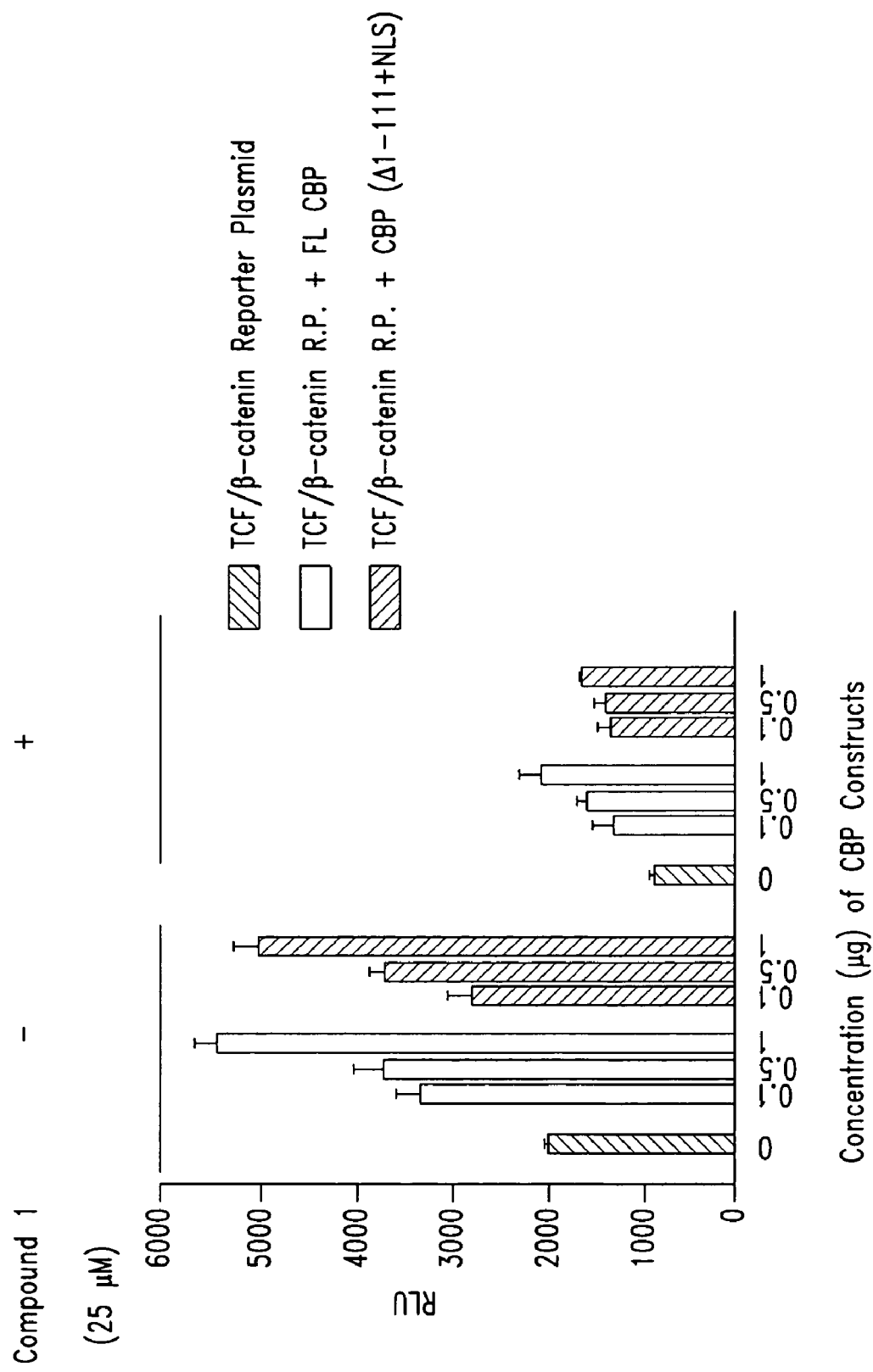

Further confirmation of the critical role played by the amino terminus of CBP was obtained utilizing the construct CBP (Δ1-111+NLS). Whereas expression of full length CBP rescued the COMPOUND 1 (25 μM) inhibition of β-catenin/ TCF promoter activity, in a dose dependent fashion, expression of CBP (Δ1-111+NLS) had no effect (FIG. 2E).

Thus, in one aspect the present invention provides a method for modulating β-catenin-induced gene expression comprising contacting a composition with an agent, where the composition comprises β-catenin, CBP and p300, and the agent is contacted with the composition in an amount effective to reduce the binding of β-catenin to CBP while having little or no effect on the binding of β-catenin to p300.

Compound 1 Competes with β-Catenin for CBP

Figure 3A:
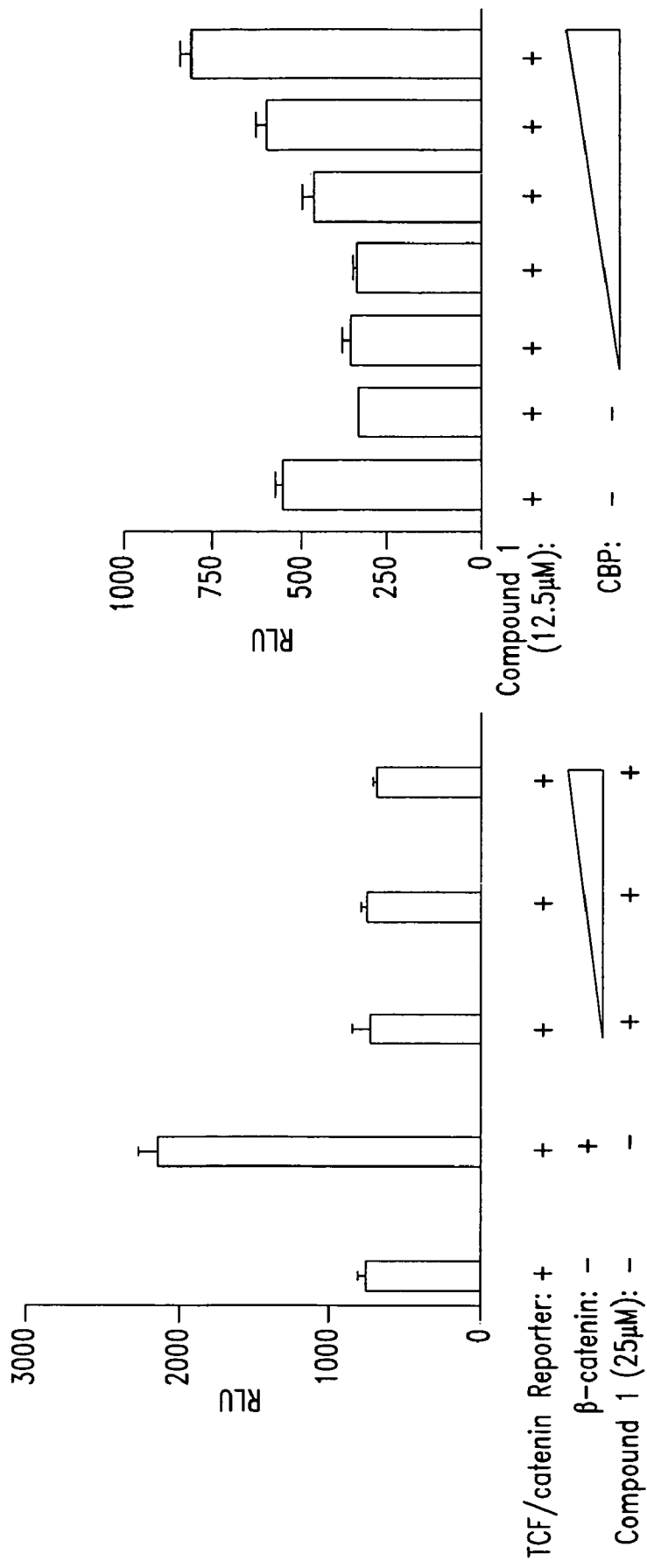
FIG. 3. COMPOUND 1 disrupts the β-catenin/CBP complex but not the p300/β-catenin complex.
- A. Full-length Xenopus laevis β-catenin (1.1, 2.2, and 3.3 μg) or murine CBP (0.14, 0.28, 0.55, 1.1, and 2.2 μg) plasmids were cotransfected in SW480 cells along with the β-catenin/TCF (1.1 μg) reporter gene construct. Empty pcDNA3 vector was used to equalize the amount of DNA used in each reaction. Dual luciferase assays were performed 24 hours post COMPOUND 1 treatment. All experiments were performed in duplicate and values plotted as means +/−standard deviation.
Figure 3B:
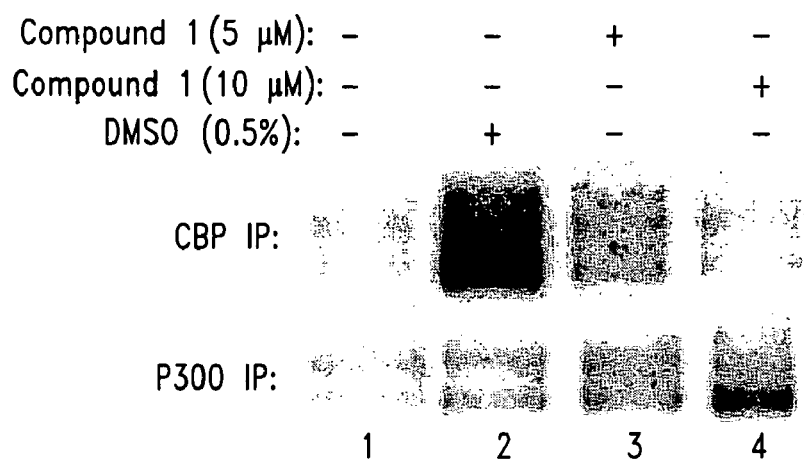

CBP is a rate-limiting factor in many transcriptional events. As seen in FIG. 3A, transfection of increasing concentration of CBP but not β-catenin, increased the IC$_{50}$ of COMPOUND 1 (12.5 μM) in a dose-dependent manner. Immunoprecipitation assays were performed in SW480 cells to determine that COMPOUND 1 disrupts β-catenin binding to CBP. Immunoprecipitation of β-catenin with CBP was inhibited by COMPOUND 1 in a concentration dependent manner (FIG. 3B, compare lanes 2, 3, and 4, lane 1 is the control, no antibody was added). The binding of COMPOUND 1 to CBP is very specific, as the compound did not interfere with the binding of β-catenin to p300 (FIG. 3B, lower panel, compare lanes 2-4) despite the fact that CBP and p300 are highly homologous.

Figure 3C:
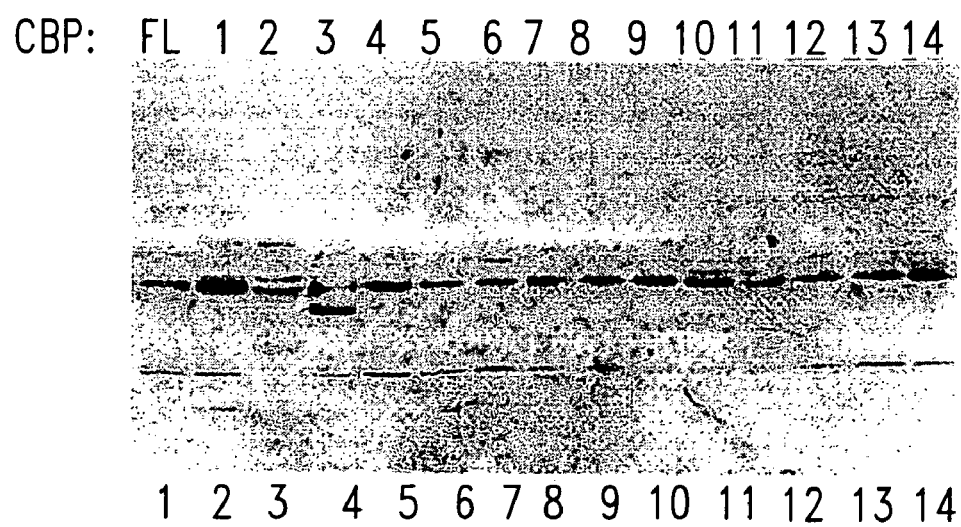
Figures 3D, 3E:
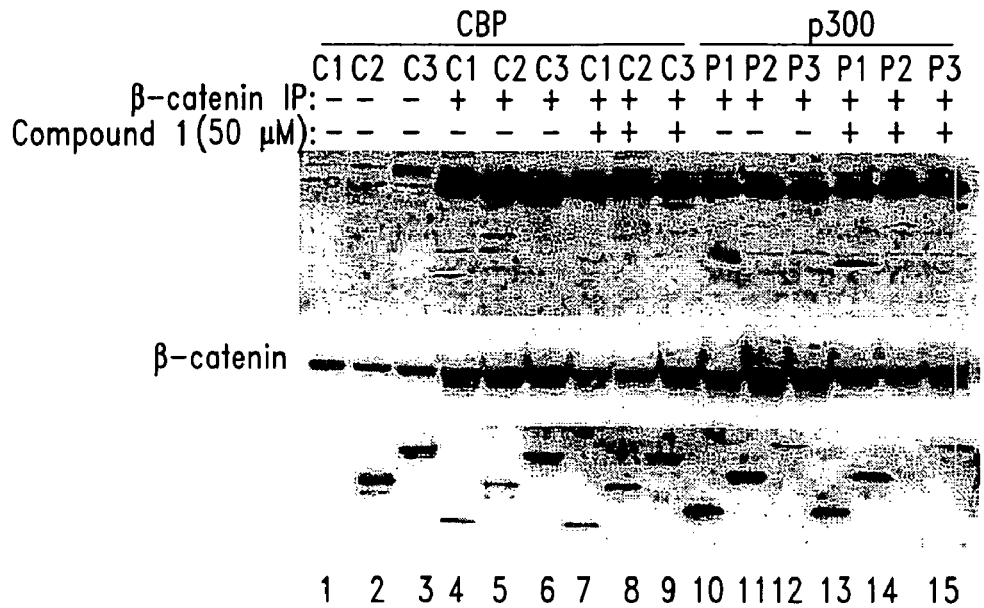

To further confirm the above β-catenin/CBP interaction, SW480 cells were transfected with the above described CBP and p300 deletion constructs (FIG. 2A). After subsequent washing of the beads, CBP (1-111), CBP (1-211), and CBP (1-351) as well as p300 (1-111), p300 (1-211), and p300 (1-351) remained specifically bound to the immunoprecipitated β-catenin (FIG. 3C, compare lanes 2-4 to 5-15). These binding studies highlight that the first 111 amino acids of the NH$_2$-terminii of both CBP and p300 bind to β-catenin. To confirm that this region overlaps the CBP binding site of COMPOUND 1, we assessed the binding of CBP (1-111), CBP (1-211) and CBP (1-351) and p300 (1-111), p300 (1-211), and p300 (1-351) to β-catenin in the presence of excess COMPOUND 1. FIG. 3D, lower panel, shows comparable levels of expression of these fragments in SW480 cells. Exposure to excess COMPOUND 1 dramatically competed away the fragments binding to β-catenin, yet had no effect on the p300 fragments binding to β-catenin (FIG. 3D, upper panel, compare lanes 4-9, to 10-15). From the data presented, COMPOUND 1 specifically binds to the amino terminus of CBP (1-111 amino acids) discriminating between the two highly homologous coactivators, CBP and p300, and competes away the interaction of β-catenin with CBP.

These binding studies have highlighted the first 111 amino acids of both CBP and p300 as the minimal region of interaction with β-catenin. The sequence alignment of these regions shows striking similarities to previously published β-catenin binding motifs found in TCF, APC and E-cadherin (FIGS. 3E and 3F). Sequence alignment data strongly suggest that CBP, like other β-catenin interacting proteins, harbors the conserved stretch of negatively charged amino acids required for β-catenin binding.

Compound 1 Decreases Nuclear β-catenin

Figure 4B:
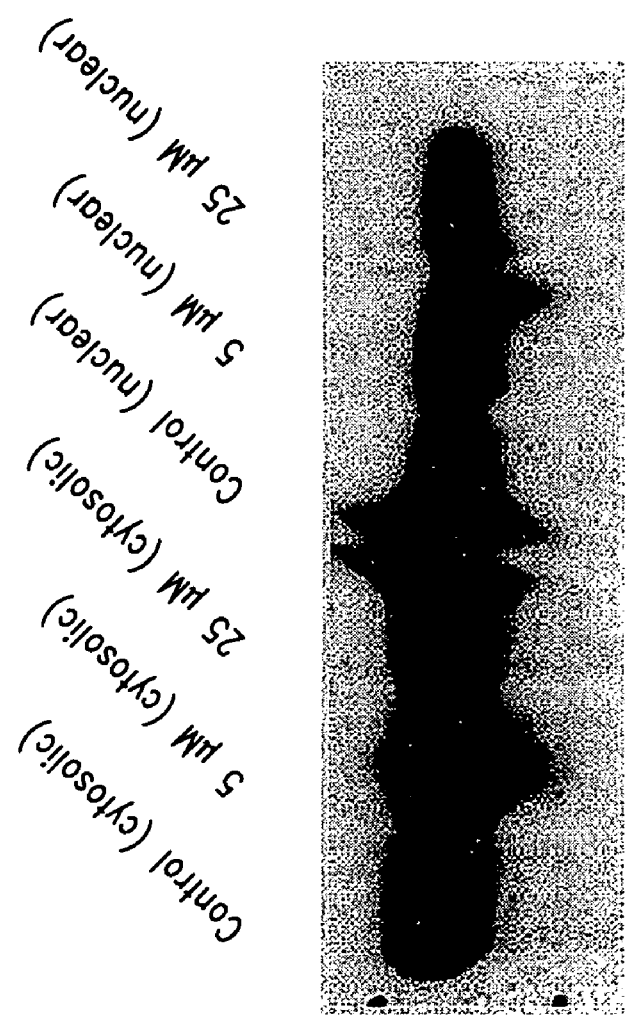

The subcellular distribution of β-catenin and CBP was examined in order to determine whether the localization of either was affected by COMPOUND 1. The majority of the endogenous β-catenin in SW480 cells is found in the nucleus as is CBP (FIG. 4A). Treatment with COMPOUND 1 caused translocation of β-catenin to the cytoplasm of SW480 cells in which the expression of endogenous E-cadherin is limited (FIG. 4A, compare the control, upper, to the treated cells, lower panel) (de Vries et al., "In vivo and in vitro invasion in relation to phenotypic characteristics of human colorectal carcinoma cells," *Br. J. Cancer* 71:271-77 (1995)). Treatment with the nuclear transport inhibitor leptomycin B eliminated COMPOUND 1-induced cytoplasmic transport of β-catenin suggesting that the nuclear export of β-catenin observed in FIG. 4A was due to COMPOUND 1 disruption of the β-catenin/CBP complex (data not shown). Accordingly, we conclude that disruption of β-catenin binding to CBP leads to reduced nuclear levels of β-catenin. COMPOUND 1-induced translocation of β-catenin from the nucleus to the cytoplasm of SW480 cells was observed by western blot analysis (FIG. 4B).

Differential Regulation and Co-activator Utilization by β-Catenin Target Genes

The cyclin D1 gene is inappropriately expressed in many different tumor types, and is known to be a direct target of the Wnt/β-catenin pathway (Shtutman et al., "The cyclin D1 gene is a target of the beta-catenin/LEF-1 pathway," *Proc. Natl. Acad. Sci. USA* 96:5522-27 (1999); Tetsu et al., "Beta-catenin regulates expression of cyclin D1 in colon carcinoma cells," *Nature* 398:422-26 (1999)). In order to determine the effect of COMPOUND 1 on the expression of this direct target of the β-catenin/TCF pathway, Real Time Reverse Transcription-PCR (RT-PCR) was conducted on mRNA extracted from cells treated with COMPOUND 1 (25 µM) or control, at 4, 8, and 24 hours time points post-treatment (Table 1). Table 1 shows the results of Quantitative Real Time Reverse Transcription-PCR (RT-PCR) analysis of SW480 cells treated for 4, 8, or 24 hours with either COMPOUND 1 (25 µl) or control (0.5% DMSO). 1 µg of mRNA, for each time point, was subjected to Real Time RT-PCR. Expression level of endogenous cyclin D1, c-myc, fibronectin, hnkd, axin2, c-jun, and BMP-4 were measured relative to β-actin. Quantitation of The ΔCycle of Threshold (CT) values was determined by subtracting the average values of each set by the corresponding average values obtained for β-actin. All experiments were performed in duplicate.

TABLE 1

Real Time RT-PCR

| Gene | Incubation Period (hours) | *ΔCT COMPOUND 1 (25 µM) | mRNA |
|---|---|---|---|
| cyclin D1 | 4 | 0.6 | ↓ |
|  | 24 | 3.1 |  |
| axin2 | 4 | 0.3 | ↓ |
|  | 8 | 0.8 |  |
| hnkd | 4 | 0.3 | ↓ |
|  | 8 | 1.0 |  |
| c-jun | 4 | 0 | ↑ |
|  | 24 | −2.9 |  |
| fra-1 | 4 | −1.0 | ↑ |
|  | 8 | −1.4 |  |
| c-myc | 4 | −0.9 | ↑ |
|  | 8 | −2.4 |  |

Figure 5A:
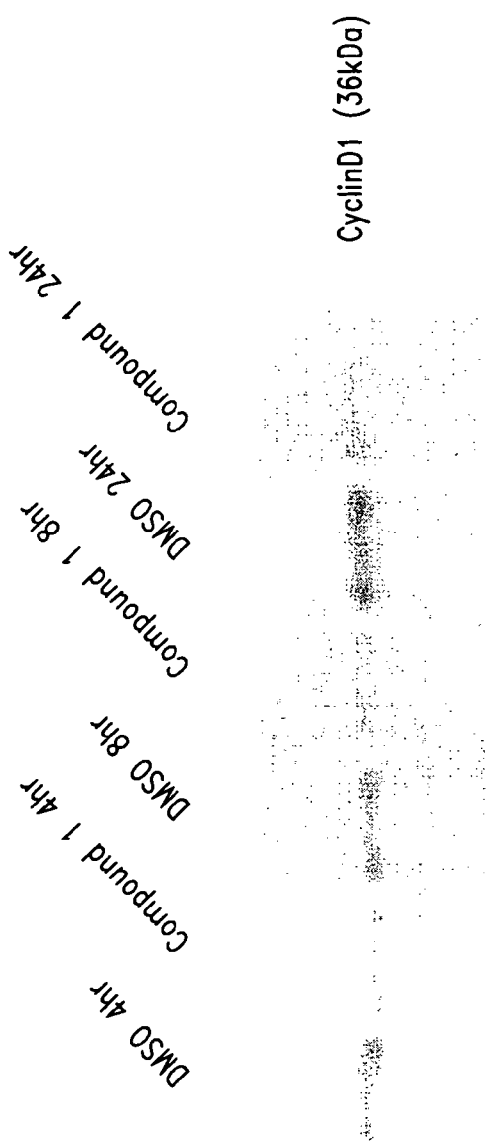

The β-actin gene was used to normalize the data. The ΔCycle of Threshold (CT) values were determined by subtracting the average values of each set from the corresponding average values obtained for the β-actin gene. The lower the amount of mRNA in the cells, the higher the corresponding ΔCT value would be. As summarized in Table 1, an increase in the ΔCT values for cyclin D1 message in cells treated with COMPOUND 1 was observed, in a time-dependent manner, in comparison to the control cells. Cyclin D1 protein levels in cells were also evaluated. Whole cell lysates of SW480 cells treated were subjected to gel electrophoresis and Western blot analysis. As shown in FIG. 5A, there was a clear reduction in the level of Cyclin D1 upon treatment with COMPOUND 1 (25 µM), beginning at 4 hours and increasing at 24 hours post treatment (compare lanes, 1 to 2, 3 to 4, and 5 to 6).

Additionally, a subset of genes were selected which had previously been reported in the literature to be direct targets of β-catenin/TCF transcription for analysis by Real Time-RT PCR. Among the set, the message levels for axin2, and human naked cuticle (hnkd) (Yan et al., "Elevated expression of axin2 and hnkd mRNA provides evidence that Wnt/beta-catenin signaling is activated in human colon tumors," *Proc. Natl. Acad. Sci. USA* 98:14973-78 (2001)) were down-regulated as anticipated (Table 1). However, for several β-catenin/TCF regulated genes, message levels increased significantly, e.g., c-myc (He et al., "Identification of c-MYC as a target of the APC pathway," *Science* 281:1509-12 (1998)), c-jun and fra-1 (Table 1) (Mann et al., "Target genes of beta-catenin-T cell-factor/lymphoid-enhancer-factor signaling in human colorectal carcinomas," *Proc. Natl. Acad. Sci. USA* 96:1603-08 (1999)). Thus, COMPOUND 1 inhibits expression of only a subset of β-catenin target genes.

Figure 5B:
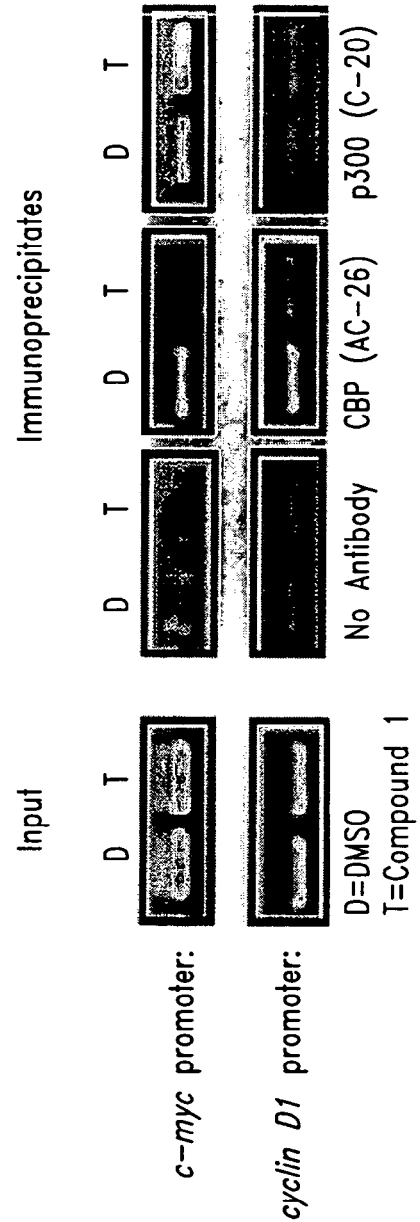

The finding that COMPOUND 1 inhibited expression of cyclin D1 but not c-myc, two known target genes of β-catenin signaling, combined with the specificity of COMPOUND 1 for CBP but not p300 suggested that selective utilization of p300 by the c-myc promoter may allow it to escape repression by COMPOUND 1. To evaluate coactivator usage at the endogenous c-myc promoter, Chromatin Immunoprecipitation (ChIP) assays on SW480 cells treated with either COMPOUND 1 (25 µM) or control (0.5% DMSO) were performed. As shown in FIG. 5B, the c-myc promoter is occupied by both coactivators CBP and p300 in control treated cells, with the majority being occupied by CBP. Treatment with COMPOUND 1 completely and selectively blocks the association of CBP with the c-myc promoter and concomitantly, the level of p300 associated is increased. Similar to the c-myc promoter, treatment with COMPOUND 1 completely and selectively blocks the association of CBP with the cyclin D1 promoter (FIG. 5B, lower panel). In sharp contrast, p300 cannot substitute for CBP for binding to the promoter of the cyclin D1 gene. This correlates well with data obtained by Real Time RT-PCR and Western blot analysis (Table 1 and FIG. 5A). Accordingly, COMPOUND 1 selectively reduces the association of CBP but not p300 with a subset of β-catenin-regulated promoters.

To further study the selectivity of COMPOUND1, cDNA microarray analysis using the Clontech Atlas Human Cancer 1.2 Array (#7851-1) was performed. The data demonstrated that COMPOUND 1 had a very selective effect on global gene transcription (Tables 2-5). After 8 hours of treatment of SW480 cells with 25 µM COMPOUND 1, ~2% of the genes analyzed were upregulated more than 2-fold while ~0.3% of the genes were down-regulated by greater than 50% (Tables 2-3).

TABLE 2

Genes Up-regulated by 8-hour Treatment of 25 µM COMPOUND1 in SW480 Cells

| Gene code | Ratio | Protein/gene |
|---|---|---|
| A12d | 4.20 | epidermal growth factor receptor (EGFR) |
| A13c | 2.48 | fos-related antigen (FRA1) |
| A14d | 1.36 | ERBB-3 receptor protein-tyrosine kinase precursor |
| A14n | 1.94 | brain glucose transporter 3 (GTR3) |
| B08h | 2.56 | PTPCAAX1 nuclear tyrosine phosphatase (PRL-1) |

TABLE 2-continued

Genes Up-regulated by 8-hour Treatment of
25 μM COMPOUND1 in SW480 Cells

| Gene code | Ratio | Protein/gene |
|---|---|---|
| C01a | 1.84 | WSL protein + TRAMP + Apo-3 + death domain receptor 3 (DDR3) |
| C05d | 6.92 | growth arrest &DNA-damage-inducible protein 153 (GADD153) |
| C09i | 5.36 | growth arrest &DNA-damage-inducible protein (GADD45) |
| D03b | 1.47 | DNA-binding protein CPBP |
| D03e | 2.82 | integrin alpha 3 (ITGA3); galactoprotein B3 (GAPB3) |
| D03k | 1.77 | low-affinity nerve growth factor receptor (NGF receptor; NGFR) |
| D06e | 1.84 | integrin beta 4 (ITGB4); CD104 antigen |
| D08e | 1.69 | integrin alpha 7B precursor (IGA7B) |
| D08f | 2.14 | paxillin |
| D09b | 2.11 | nuclear protein |
| E03d | 3.27 | nerve growth factor-inducible PC4 homolog |
| E07f | 1.77 | interleukin-1 beta precursor (IL-1; IL1B); catabolin |
| E09e | 6.94 | macrophage inhibitory cytokine 1 (MIC1) |
| F04i | 5.85 | neutrophil gelatinase-associated lipocalin precursor (NGAL) |
| F05e | 1.82 | ornithine decarboxylase |
| F06n | 3.15 | early growth response alpha (EGR alpha) |
| F08f | 1.59 | type I cytoskeletal 18 keratin; cytokeratin 18 (K18) |
| F09g | 6.40 | gravin |
| F13k | 2.23 | glycyl tRNA synthetase |

TABLE 3

Genes Down-regulated by 8-hour Treatment of
25 μM COMPOUND1 in SW480 Cells

| Gene code | Ratio | Protein/gene |
|---|---|---|
| A05i | 0.57 | G2/mitotic-specific cyclin B1 (CCNB1) |
| A10f | 0.77 | matrix metalloproteinase 11 (MMP11); stromelysin 3 |
| B01m | 0.74 | linker for activation of T-cells (LAT) |
| B07l | 0.85 | placental calcium-binding protein; calvasculin |
| B12j | 0.62 | ras-related C3 botulinum toxin substrate 2; p21-rac2 |
| B14n | 0.74 | retinoic acid receptor beta (RXR-beta; RXRB) |
| C06f | 0.38 | MCM4 DNA replication licensing factor; CDC21 homolog |
| C13e | 0.38 | proliferating cyclic nuclear antigen (PCNA); cyclin |
| D08b | 0.73 | histone H4 |
| D11c | 0.60 | T-cell surface glycoprotein CD3 epsilon subunit precursor |
| E01g | 0.88 | interleukin-13 precursor (IL-13); NC30 |
| F07e | 0.53 | ribonucleoside-diphosphate reductase M2 subunit |

TABLE 4

Genes Up-regulated by 24-hour Treatment of
25 μM COMPOUND1 in SW480 Cells

| Gene code | Ratio | Protein/gene |
|---|---|---|
| A01c | 1.34 | proto-oncogene c-jun; transcription factor AP-1 |
| A12d | 2.51 | epidermal growth factor receptor (EGFR) |
| A13c | 1.99 | fos-related antigen (FRA1) |
| C01j | 1.71 | ets domain protein elk-3; NET; SRF accessory protein 2 (SAP2) |
| C05d | 3.66 | growth arrest &DNA-damage-inducible protein 153 (GADD153) |
| D03e | 2.99 | integrin alpha 3 (ITGA3); galactoprotein B3 (GAPB3) |
| D03k | 2.50 | low-affinity nerve growth factor receptor (NGF receptor; NGFR) |
| D06e | 2.68 | integrin beta 4 (ITGB4); CD104 antigen |
| D08h | 10.39 | N-sam; fibroblast growth factor receptor1 precursor (FGFR1) |
| E02m | 1.36 | MHC class I truncated HLA G lymphocyte antigen |

TABLE 4-continued

Genes Up-regulated by 24-hour Treatment of
25 μM COMPOUND1 in SW480 Cells

| Gene code | Ratio | Protein/gene |
|---|---|---|
| E02n | 2.35 | 78-kDa glucose regulated protein precursor (GRP 78) |
| E07f | 1.98 | interleukin-1 beta precursor (IL-1; IL1B); catabolin |
| E09e | 2.79 | macrophage inhibitory cytokine 1 (MIC1) |
| F04g | 1.34 | vimentin (VIM) |
| F04i | 23.85 | neutrophil gelatinase-associated lipocalin precursor (NGAL) |
| F06n | 1.79 | early growth response alpha (EGR alpha) |
| F09g | 8.46 | gravin |
| F09h | 3.25 | TRAM protein |
| F12l | 2.07 | BENE |
| F13k | 2.02 | glycyl tRNA synthetase |
| G31 | 1.29 | HLA class I histocompatibility antigen C-4 alpha subunit (HLAC) |

TABLE 5

Genes Down-regulated by 24-hour Treatment of
25 μM COMPOUND1 in SW480 Cells

| Gene code | Ratio | Protein/gene |
|---|---|---|
| A02b | 0.52 | EB1 protein |
| A03g | 0.43 | c-myc binding protein MM-1 |
| A06i | 0.47 | G1/S-specific cyclin D1 (CCND1); cyclin PRAD1; bcl-1 oncogene |
| A10k | 0.28 | cyclin-dependent kinase regulatory subunit 1 (CKS1) |
| A11k | 0.40 | cyclin-dependent kinase regulatory subunit (CKS2) |
| B02a | 0.21 | ADP/ATP carrier protein |
| B03m | 0.45 | 14-3-3 protein sigma; stratifin; epithelial cell marker protein 1 |
| B07l | 0.50 | placental calcium-binding protein; calvasculin |
| C04b | 0.73 | tumor necrosis factor type 1 receptor associated protein (TRAP1) |
| C04h | 0.36 | HHR23A; UV excision repair protein protein RAD23A |
| C05f | 0.23 | MCM2 DNA replication licensing factor; nuclear protein BM28 |
| C13e | 0.33 | proliferating cyclic nuclear antigen (PCNA); cyclin |
| D06m | 0.45 | cytosolic superoxide dismutase 1 (SOD1) |
| D07b | 0.35 | high mobility group protein HMG2 |
| D07m | 0.34 | glutathione synthetase (GSH synthetase; GSH-S) |
| D08b | 0.27 | histone H4 |
| D09b | 0.49 | nuclear protein |
| D12a | 0.70 | chromatin assembly factor 1 p48 subunit (CAF1 p48 subunit) |
| E04i | 0.45 | PDGF associated protein |
| E11l | 0.66 | CD59 glycoprotein precursor |
| F03e | 0.34 | fatty acid synthase |
| F06d | 0.40 | L-lactate dehydrogenase H subunit (LDHB) |
| F10c | 0.68 | inosine-5'-monophosphate dehydrogenase 2 |
| F13j | 0.55 | elongation factor 2 (EF2) |
| G29 | 0.72 | brain-specific tubulin alpha 1 subunit (TUBA1) |
| G45 | 0.65 | 23-kDa highly basic protein; 60S ribosomal protein L13A |

Compound 1 Causes a $G_1$/S-Phase Arrest and Activates Caspase Activity

Figure 6A:
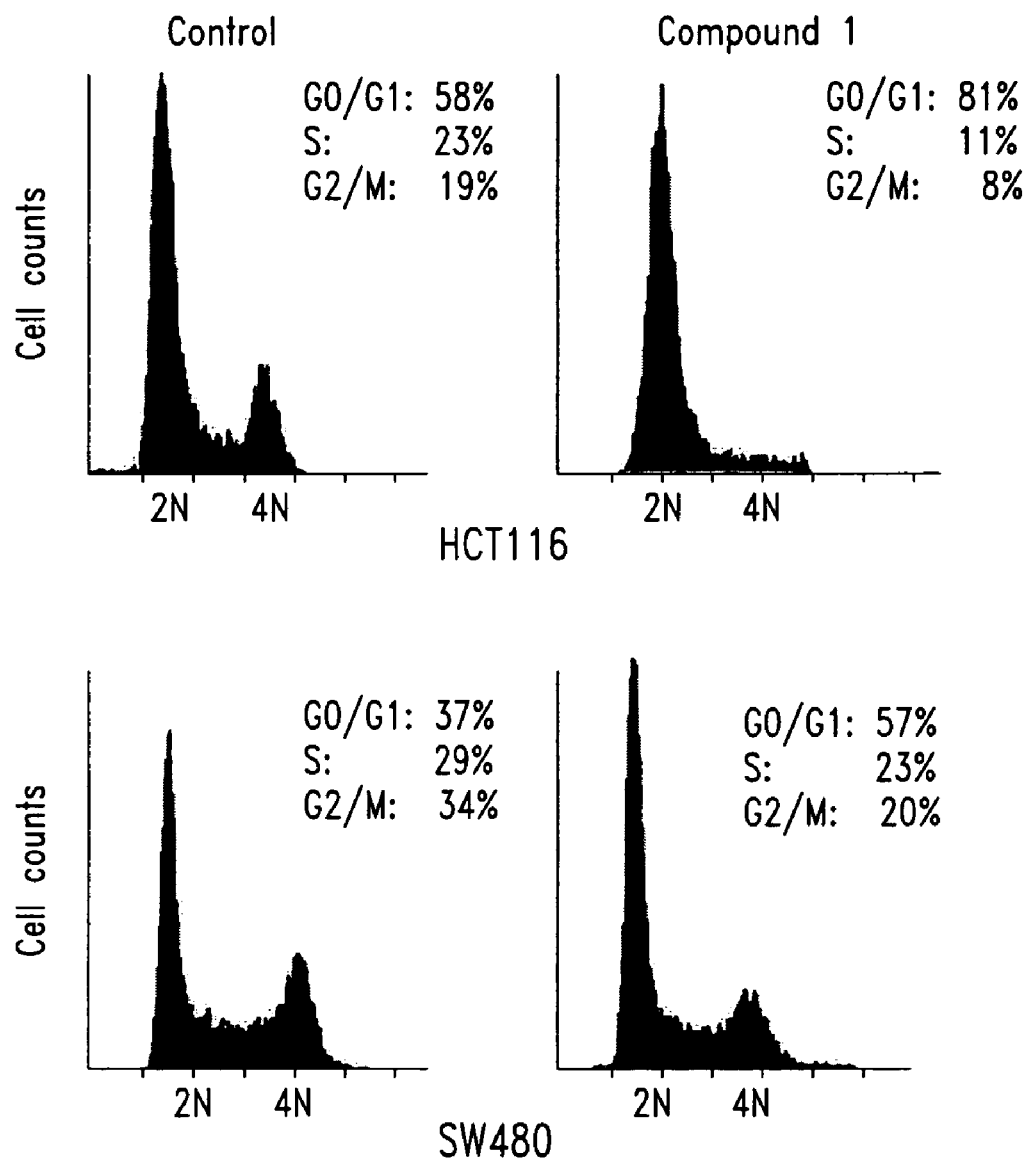

It has been shown that inhibition of the expression of the cyclin D1 gene causes arrest at the $G_1$/S-phase of the cell cycle (Shintani et al., "Infrequent alternations of RB pathway (Rb-p16INK4A-cyclin D1) in adenoid cystic carcinoma of salivary glands," *Anticancer Res.* 20:2169-75 (2000)). HCT116 (FIG. 6A, upper panel) and SW480 (FIG. 6A, lower panel) cells were treated with COMPOUND 1 (25 μM) (FIG. 6A, right) or control (0.5% DMSO) (FIG. 6A, left) for 24 hours. The cells were subsequently stained with propidium iodide (PI) and analyzed for DNA content by FACS cytofluorometry. As expected, the control cells, (FIG. 6A, left), were cycling normally whereas the COMPOUND 1 treated cells (FIG. 6A, right) showed increased accumulation at $G_1$/S-phase of the cell cycle. Thus, it can be seen that COMPOUND 1 causes arrest of cells at the $G_1$ phase.

Figure 6B:
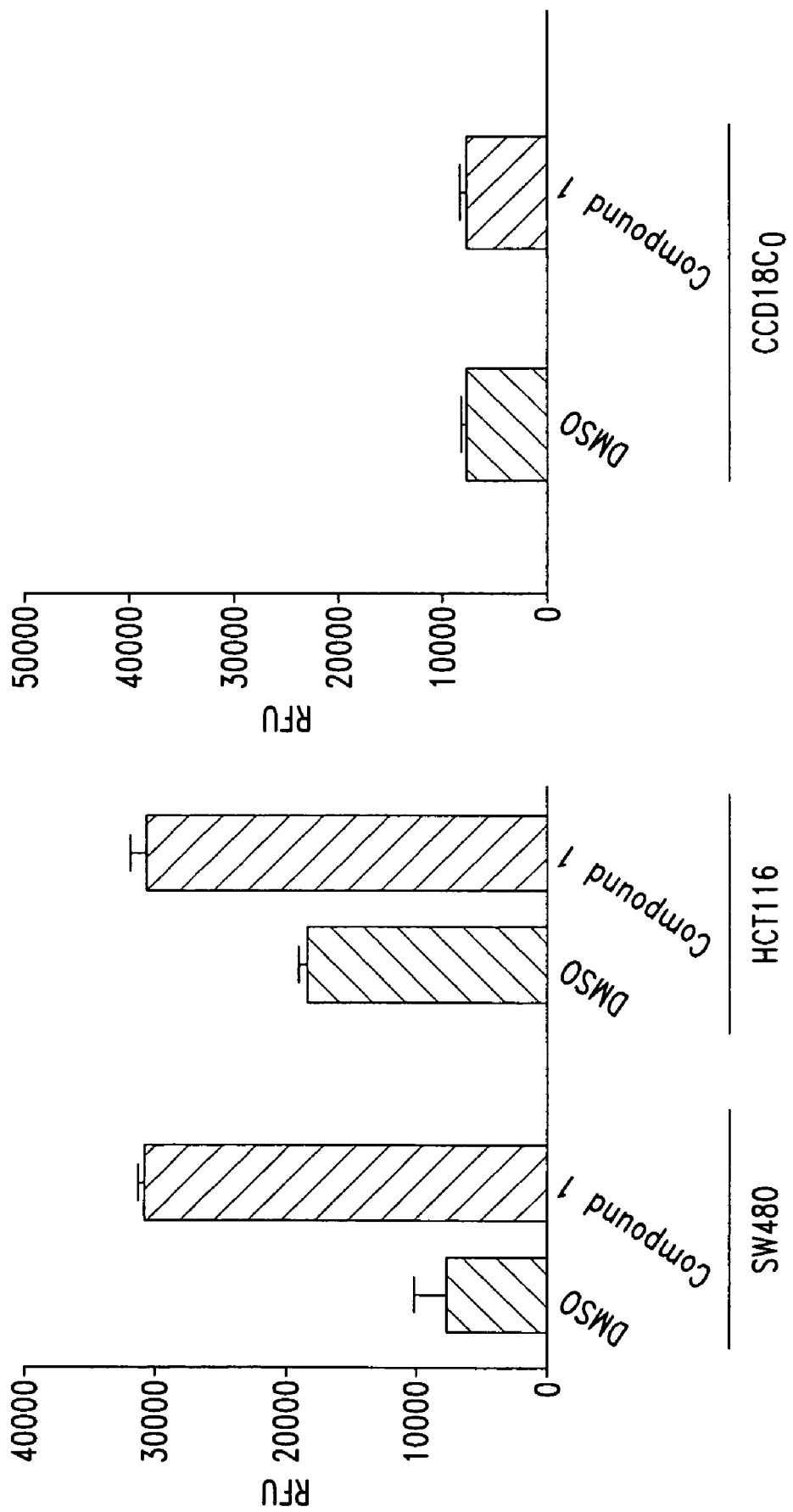

Caspases are cysteine proteases that are generally activated in a given population of cells triggered by apoptotic stimuli. To assess apoptotic induction in SW480, HCT116, and wild-type colonocytes (CCD18Co cells), the cells were treated with either COMPOUND 1 (25 µM) or control (0.5% DMSO) for 24 hours, followed by an assay for caspase-3/7 activity. As shown in FIG. 6B, COMPOUND 1 specifically and significantly activated the caspase-3/7 pathway in SW480 and HCT116 cells compared to CCD18Co cells.

Compound 1 Reduces Proliferation of Transformed Colorectal Cells

Figure 7A:
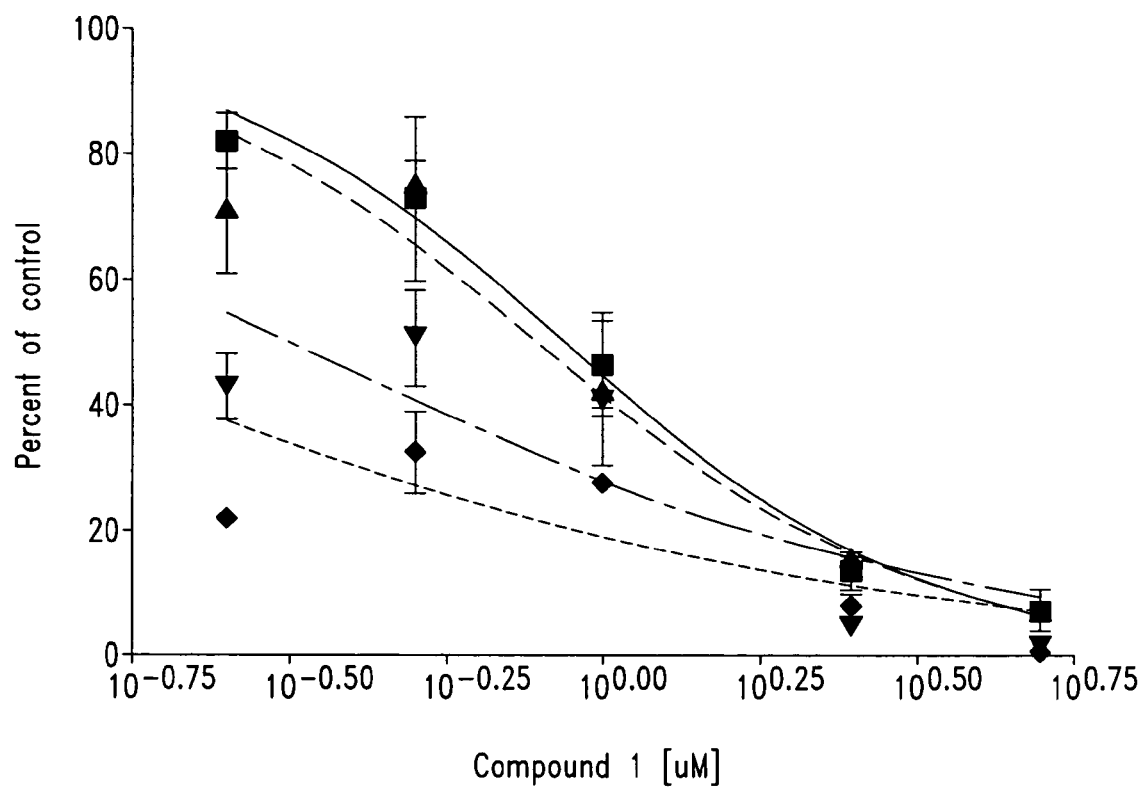

Soft agar colony forming assays were performed using SW480 cells treated with COMPOUND 1 (0.25-5 µM) and 5-fluorouracil (5-FU) (0.5-32 µM). As shown in FIG. 7A, COMPOUND 1 shows a dose dependent decrease in the number of colonies formed. $IC_{50}$ value of COMPOUND 1 and 5-FU was 0.87±0.11 µM and 1.98±0.17 µM, respectively. Thus, COMPOUND 1 increased caspase activity and reduced growth in vitro of colorectal cells that are transformed by mutations that activate β-catenin signaling.

Compound 4 and Compound 5 Reduce Tumor Growth in Min Mouse Model

COMPOUND 4, COMPOUND 5, or vehicle was administrated in wild type and Min mice. COMPOUND 4 is also an analog of COMPOUND 1 (FIG. 1A). The numbers of polyp formed in small intestine and colon of these mice after various treatments were measured (Table 6). The data shown that both COMPOUND 4 and COMPOUND 5, when administered at about 300 mpk, reduce the number of polyp in min mice compared to those in the control mice treated with vehicle only.

TABLE 6

Effects on COMPOUND 4 and COMPOUND 5 on the number of polyp in Min mouse model

| Group | Polyp Number (Mean + S.D.) | | | P (total) Vs. VH | % Inhibition vs. VH |
| --- | --- | --- | --- | --- | --- |
| | Small intestine | Colon | Total | | |
| Wild type | 0.0 ± 0.0 | 0.0 ± 0.0 | 0.0 ± 0.0 | — | — |
| Vehicle | 65.8 ± 15.9 | 1.8 ± 1.5 | 67.7 ± 15.3 | — | — |
| COMPOUND 5 –100 mpk | 69.2 ± 20.8 | 1.7 ± 1.5 | 71.4 ± 23.0 | — | — |
| COMPOUND 5 –300 mpk | 46.1 ± 17.1 | 1.1 ± 1.2 | 47.0 ± 16.9 | <0.01 | 31 |
| COMPOUND 4 –300 mpk | 45.2 ± 22.1 | 1.4 ± 0.9 | 46.8 ± 17.0 | <0.01 | 31 |
| Sulindac –160 ppm | 48.0 ± 20.7 | 0.5 ± 0.5 | 48.5 ± 20.9 | <0.05 | 28 |

Cytotoxicity of Compound 3

Cytotoxicity of COMPOUND 3 (an analog of COMPOUND 1, FIG. 1A) and other anticancer therapeutics were measured using cancer cells with various origins. The results show that COMPOUND 3 at concentrations lower than or similar to those for other anticancer therapeutics (i.e., cisplatin, 5-FU, ADR (adriamycin)) causes cancer cell death (Table 7).

TABLE 7

| | | Cytotoxicity | | | |
| --- | --- | --- | --- | --- | --- |
| Origin | Cell | COMPOUND 3 | Cisplatin | 5-FU | ADR |
| Leukemia | HL60 | 1.243 | >10 | 7.010 | 0.086 |
| Prostate | PC3 | 1.207 | >10 | >10 | 0.267 |
| Lung | A549 | 1.386 | >10 | 1.007 | 0.117 |
| Renal | 293 | 0.731 | 6.641 | 2.015 | <0.03 |
| Melanoma | RPM17951 | 0.936 | 5.010 | 0.920 | 0.171 |
| Breast | MCF7 | 7.355 | >10 | 1.751 | 1.424 |

The values in Table 7 are in µg/ml.

Metabolism of Compound 3 in Rat and Human

Figure 10A:
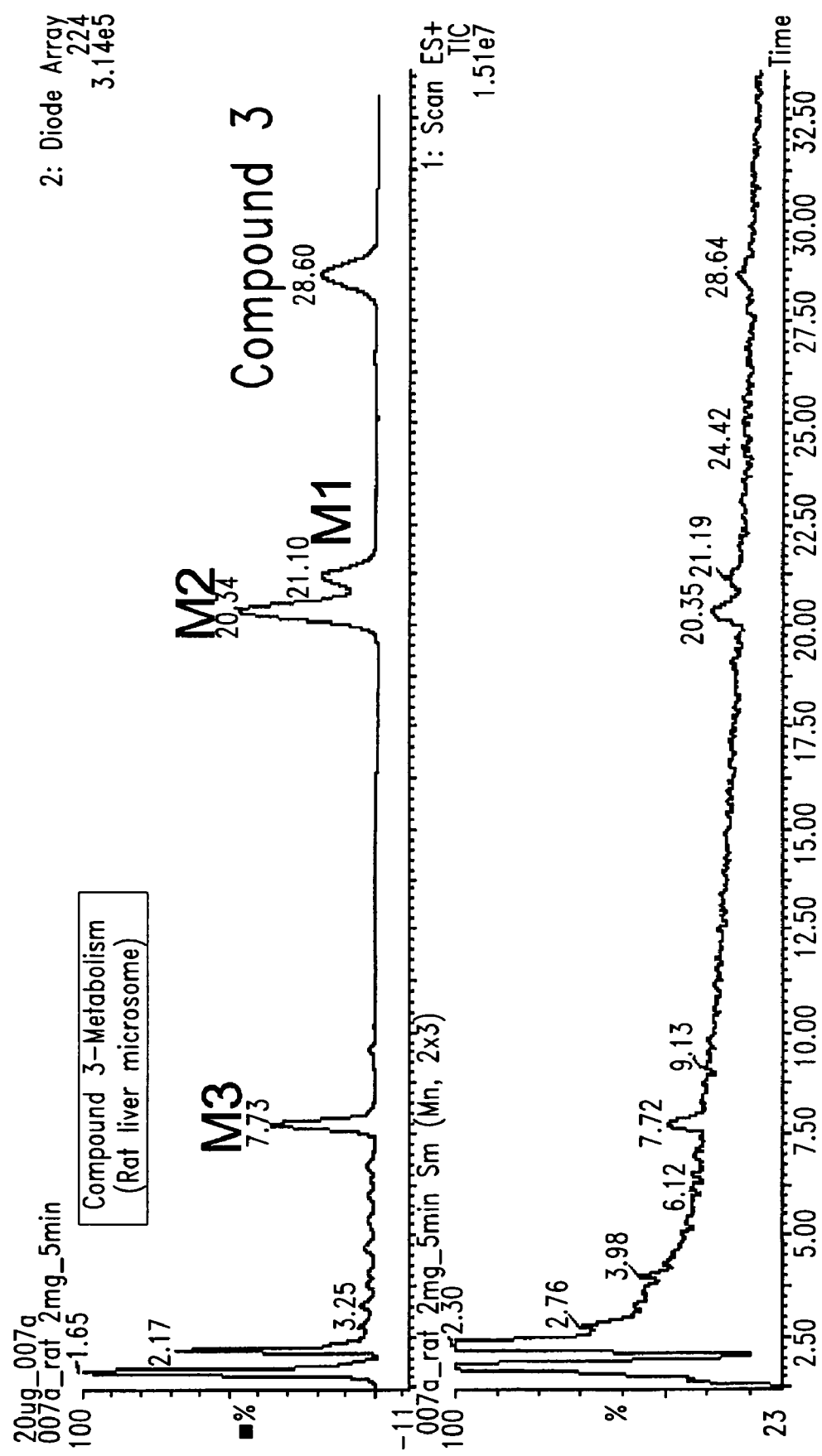
Figure 10B:
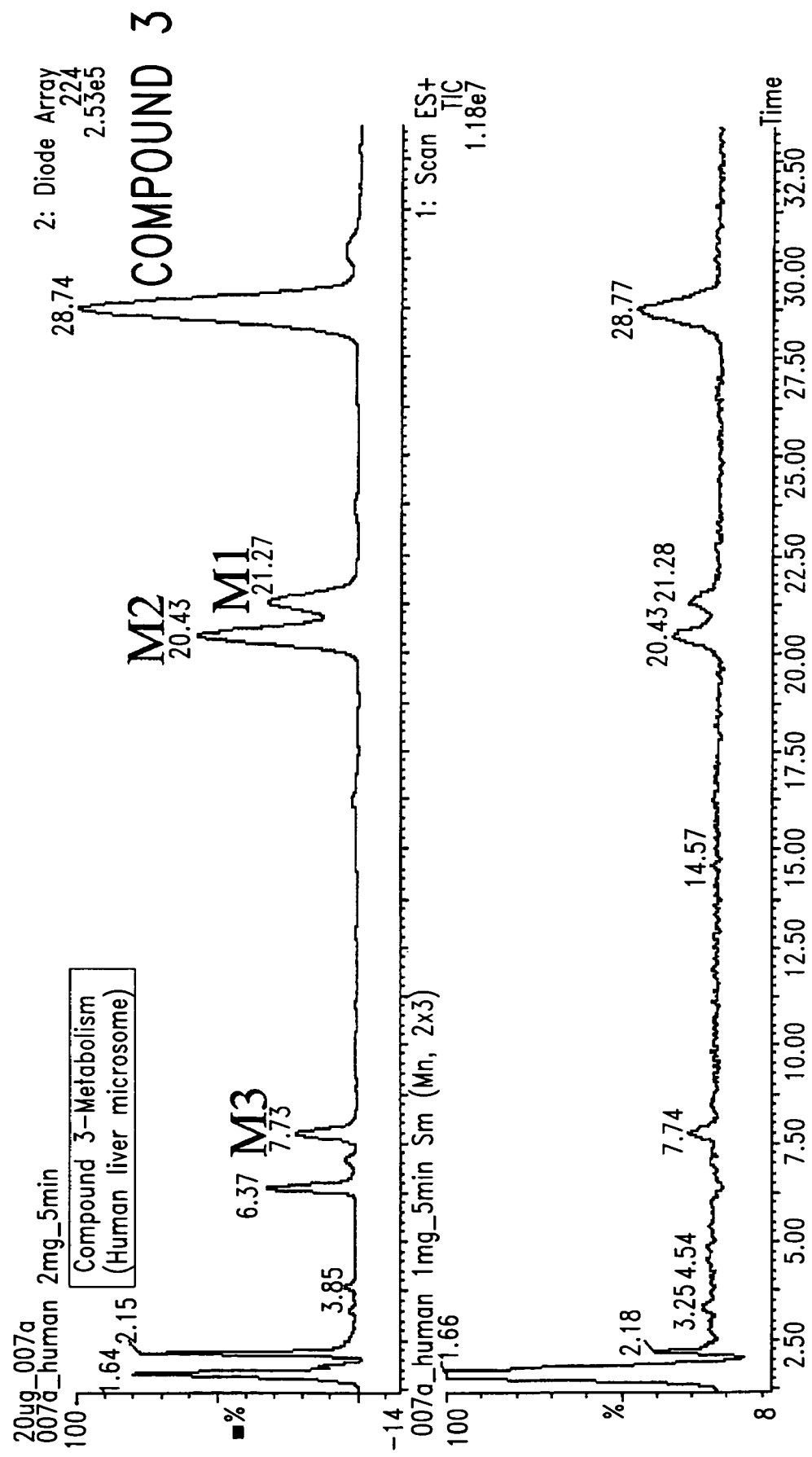

Metabolism of COMPOUND 3 was analyzed by incubating the compound with rat or human liver microsome for 5 minutes to 1 hour, fractioning extracts of treated microsome through HPLC and subjecting the fractions to MS analysis. The results are shown in FIGS. 10A and 10B. Several metabolites (e.g., M1, M2, M3) were observed in both systems.

Bioavailability Study of Compound 3, Compound 4 and Compound 5

Bioavailability of COMPOUND 3, COMPOUND 4 and COMPOUND 5 was studied in mouse and rat. Structures of these compounds are shown in FIG. 1A. All the compounds were administered (i.v and p.o, 10 mg/kg) using the same vehicle (i.e., 20% Tween 80). The bioavailability of COMPOUND 3, 4, and 5 in mouse is below 2%, below 2%, and almost 0%, respectively. The bioavailability of COMPOUND 3 in rat is about 24%.

Discussion

There is mounting and compelling evidence that misregulation of the β-catenin pathway is involved in the development and progression of cancer (Morin, P.J., "Beta-catenin signaling and cancer," Bioessays 21:1021-30 (1999); Moon et al., "The promise and perils of Wnt signaling through beta-catenin," Science 296:1644-46 (2002); Oving et al., "Molecular causes of colon cancer," Eur. J. Clin. Invest. 32:448-57 (2002)). Herein, we describe the discovery that compounds of formula (I) inhibit a subset of β-catenin/TCF transcription. The biological activity of these low molecular weight inhibitors was characterized using a reporter gene screen utilizing a secondary structure-templated chemical library in SW480 colon carcinoma cells, which have mutations in the APC gene leading to constitutively elevated β-catenin/TCF transcription. Affinity chromatography utilizing a biotinylated analog (COMPOUND 2), allowed the identification of a coactivator protein, CBP, as the molecular target of COMPOUND 1.

Transfection of CBP but not β-catenin was shown to significantly increase the binding of $^{14}$C-labeled COMPOUND 1 to SW480 nuclear lysates. To validate CBP as the molecular target of COMPOUND 1, it was shown that transfection of a CBP expression vector could override the inhibition by COMPOUND 1 of a β-catenin/TCF reporter gene construct. Furthermore, COMPOUND 1 selectively blocked the interaction of β-catenin and CBP without interfering with the interaction of β-catenin with the closely related coactivator p300. Moreover, COMPOUND 1 caused redistribution of β-catenin from the nucleus to the cytoplasm in SW480 cells. Finally, COMPOUND 1 mediated inhibition of cyclin D1 expression leads to $G_1$/S cell cycle arrest and prolonged treatment causes caspase activation in SW480 (or HCT116) cells but not in normal colonocytes, leading to apoptosis of the transformed colon carcinoma cell lines. Accordingly, COMPOUND 1 is an inhibitor of the β-catenin pathway and CBP is its cellular target.

To further study the selectivity of COMPOUND 1, cDNA Microarray analysis using the Clontech Atlas Human Cancer 1.2 Array (#7851-1) was performed. The data demonstrated that COMPOUND 1 had a very selective effect on global gene transcription (Tables 2-5). After 8 hours of treatment of SW480 cells with 25 μM COMPOUND 1, ~2% of the genes analyzed were upregulated more than 2-fold while ~0.3% of the genes were down-regulated by greater than 50% (Tables 2-3).

Figure 7B:
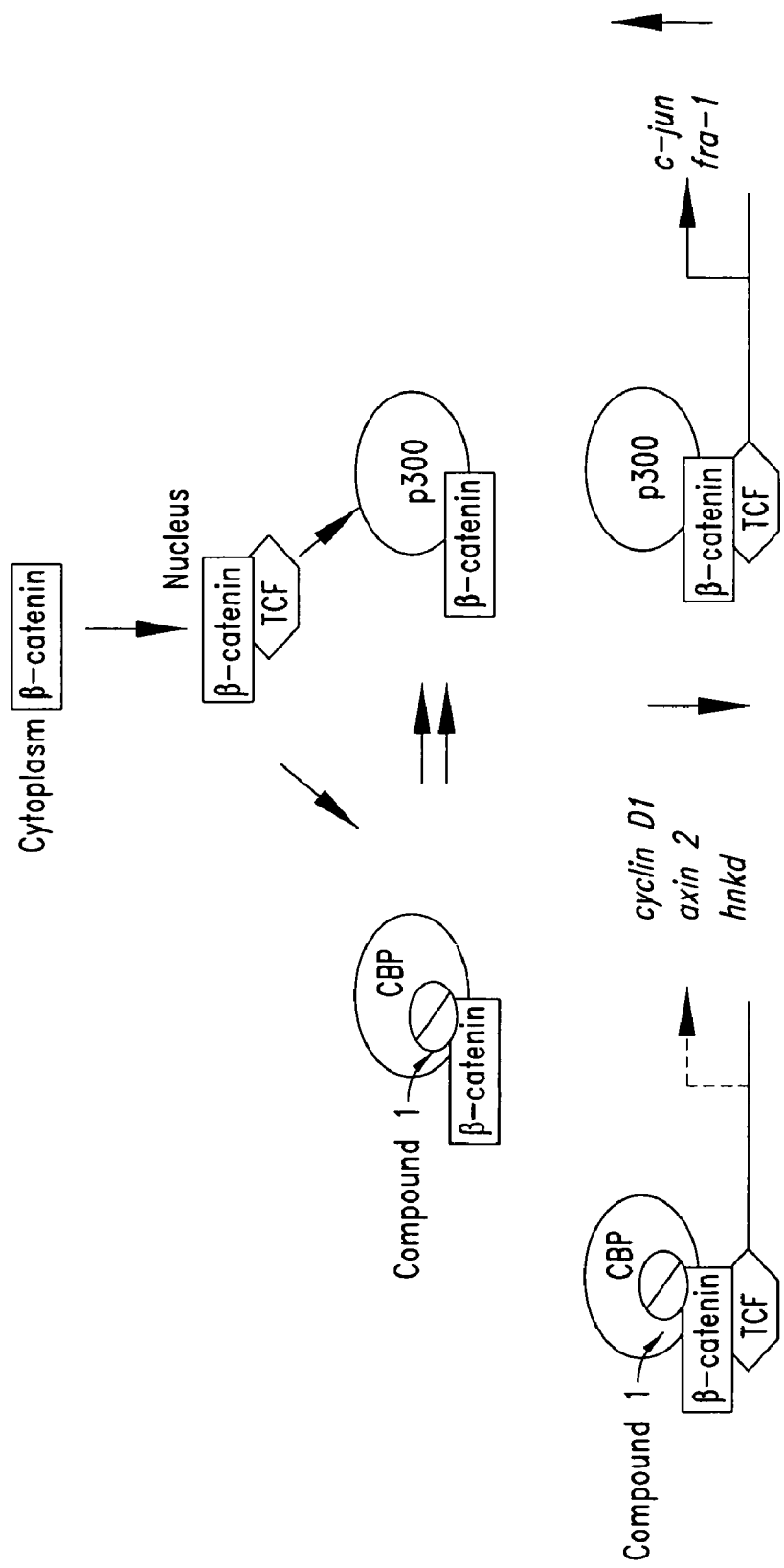

Promoter-dependent coactivator selectivity adds to the complexity of the β-catenin/TCF pathway. As anticipated, COMPOUND 1 inhibits the expression of cyclin D1, hnkd, and axin2 genes (Yan et al., "Elevated expression of axin2 and hnkd mRNA provides evidence that Wnt/beta-catenin signaling is activated in human colon tumors," Proc. Natl. Acad. Sci. USA 98:14973-78 (2001)). On the contrary, the expression of c-myc (He et al., "Identification of c-MYC as a target of the APC pathway," Science 281:1509-12 (1998)) and c-jun (Mann et al., "Target genes of beta-catenin-T cell-factor/lymphoid-enhancer-factor signaling in human colorectal carcinomas," Proc. Natl. Acad. Sci. USA 96:1603-08 (1999)) is increased, due to differential coactivator usage in the β-catenin/TCF pathway (Table 1 and FIG. 7B). Utilizing ChIP assays, it was demonstrated that COMPOUND 1 selectively inhibits the association of CBP with the endogenous c-myc and cyclin D1 promoters, and that in treated cells, for c-myc promoter and not cyclin D1 promoter, occupation of the promoter by p300 is increased. This correlates extremely well with the data obtained in the β-catenin co-IP experiments and the Real Time RT-PCR data for cyclin D1. COMPOUND 1, which is selective for inhibiting the β-catenin/CBP interaction and related analogs which are selective for the β-catenin/p300 (Kahn et al., unpublished data), are providing novel chemogenomic tools to address the mechanisms by which the β-catenin/TCF complex activates gene transcription in a promoter-dependent and coactivator-specific manner (FIG. 7B).

There exist significant discrepancies in the literature concerning the specific contact sites of interaction between β-catenin and the coactivator proteins CBP and p300. This is presumably related to the promiscuous and generally low to moderate affinity binding of both CBP and p300 to β-catenin to many target proteins. We anticipated that we could use the binding specificity of COMPOUND 1 for CBP to clarify this situation. Binding studies of COMPOUND 1 with CBP fragments led to the discovery of a minimal region of interaction at the $NH_2$-terminus of CBP (amino acids 1-111). Moreover, COMPOUND 1 did not bind to the homologous sequence in p300. COMPOUND 1 selectively blocked the interaction between CBP (1-111) and β-catenin in cells, without interfering with the p300 (1-111)/β-catenin interaction. The sequence alignment of this region shows striking similarities to the previously published β-catenin binding motifs found in TCF, APC and E-cadherin (FIG. 5A) (Huber et al., "The structure of the beta-catenin/E-cadherin complex and the molecular basis of diverse ligand recognition by beta-catenin," Cell 105:391-402 (2001)). Both CBP (1-111) and p300 (1-111) contain the key negatively charged buttons (DELIXXXXE) for interactions with β-catenin (Graham et al., "Tcf4 can specifically recognize beta-catenin using alternative conformations," Nat. Struct. Biol. 8:1048-52 (2001)). The SXSSXS motif, where X is an amino acid with a nonpolar aliphatic R group, found in APC and E-cadherin, is also present in CBP, SASSP (amino acids 89-93), but is missing in p300. Although, differential binding of COMPOUND 1 to CBP (1-111) versus p300 (1-111) in SW480 cells could in principle be due to differential phosphorylation, the use of known inhibitors of GSK-3β (Nikoulina et al., "Inhibition of glycogen synthase kinase 3 improves insulin action and glucose metabolism in human skeletal muscle," Diabetes 51:2190-98 (2002)) or PKC (Bollag et al., "Effects of the selective protein kinase C inhibitor, Ro 31-7549, on the proliferation of cultured mouse epidermal keratinocytes," J. Invest. Dermatol. 100:240-46 (1993)) had no apparent effect on the binding of COMPOUND 1 (data not shown). Furthermore, purified recombinant CBP (1-111) expressed in E. coli was capable of binding to COMPOUND 1, further arguing against coactivator dependent phosphorylation as the discriminating factor. Thus, using COMPOUND 1 as a tool, we have specifically mapped the minimal region of CBP interaction with β-catenin to the first 111 amino acids of CBP.

Further support for our mapping studies comes from the existence of a binding site on CBP for retinoic acid (RA) receptors, RXR/RAR, in close proximity to the β-catenin binding motif on CBP (FIG. 3F). Previously, it has been shown that RA treatment inhibits β-catenin/TCF signaling (Earswaran et al., "Cross-regulation of beta-catenin-LEF/TCF and retinoid signaling pathways," Curr. Biol. 9:1415-18 (1999)). The consensus (LXXLL) (SEQ ID NO: 46) RXR/RAR binding site (LSELL) is located at amino acid residues 70 to 74 within our proposed β-catenin binding site on both CBP and p300 (Minucci et al., "Retinoid receptors in health and disease: co-regulators and the chromatin connection. Semin," Cell Dev. Biol. 10:215-25 (1999)).

COMPOUND 1 also enabled us to address the issue of promoter-dependent coactivator-selectivity of β-catenin signaling pathway. COMPOUND 1 treatment does not inhibit the interaction of p300 with β-catenin (FIG. 3D), and in fact it actually increases the formation of β-catenin/p300 complexes in treated cells (FIG. 3B). As shown in the sequence alignment, though similar within the mapped β-catenin binding motifs, there are differences between these two coactivators that could account for the observed specificity of COMPOUND 1 for CBP but not p300. Based on these studies, it appears that the interaction between the N-terminal 111 amino acids of CBP/p300 and β-catenin is required for β-catenin/TCF transcriptional activation.

Despite intense interest in the discovery of selective small molecule inhibitors of β-catenin/TCF transcription, to the best of our knowledge, COMPOUND 1 represents the first example of a direct small molecule inhibitor of this pathway. Despite elegant structural studies on the interactions between β-catenin and TCF (Graham et al., "Crystal structure of a beta-catenin/Tcf complex," Cell 103:885-96 (2000); Graham et al., "Tcf4 can specifically recognize beta-catenin using alternative conformations," Nat. Struct. Biol. 8:1048-52 (2001); Poy et al., "Structure of a human Tcf4-beta-catenin complex," Nat. Struct Biol. 8:1053-57 (2001)), an a priori attractive mode for inhibition of this pathway, concerns arise as to the development of specific inhibitors due to the diverse partners besides TCF (e.g., APC and E-cadherin) which also bind to the central Arm repeats of β-catenin (Huber et al., "The structure of the beta-catenin/E-cadherin complex and the molecular basis of diverse ligand recognition by beta-catenin," Cell 105:391-402 (2001)). The elegant selectivity of COMPOUND 1, through its specific inhibition of the β-catenin/CBP interaction as opposed to the highly homologous coactivator p300 (which shares up to 96% identity at the amino acid level with CBP) has provided a unique chemogenomics tool to investigate β-catenin/TCF-mediated transcription. The specificity of COMPOUND 1, its ability to selectively activate apoptotic caspases in transformed but not normal colonocytes and its efficacy in the soft agar colony forming assay are all very encouraging signs for its potential therapeutic utility in colon cancer. Furthermore, analogs of COMPOUND 1 have shown in vivo efficacy, with limited toxicity, in murine cancer models (nude mice injected with SW480 cells and Min mouse model; Moser et al., "ApcMin: a mouse model for intestinal and mammary tumorigenesis," *Eur. J. Cancer A:*1061-64 (1995); Kahn et al., unpublished data) further validating the use of selective inhibitors of β-catenin/TCF/CBP transcription for potential use in cancer chemotherapy, as well as other hyperproliferative disorders.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for increasing the expression of a target gene induced by β-catenin, comprising contacting a stem cell with an agent having the structure of formula (I),

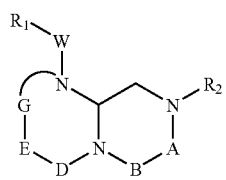

wherein A is —(CHR$_3$)— or —(C=O)—, B is —(CHR$_4$)— or —(C=O)—, D is —(CHR$_5$)— or —(C=O)—, E is -(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1; and R$_1$, R$_2$, R$_3$, R$_4$, R$_5$, R$_6$, R$_7$, R$_8$ and R$_9$ are each independently selected from an amino acid side chain moiety, a derivative of an amino acid side chain moiety, and stereoisomers thereof, and wherein the agent is contacted with the stem cell in an amount effective to increase the expression of a target gene induced by β-catenin.

2. The method of claim 1 wherein the agent increases the binding of p300 to β-catenin.

3. The method of claim 1 wherein the agent decreases the binding of CBP to β-catenin.

4. The method of claim 1 wherein the agent promotes differentiation of the stem cell.

5. The method of claim 1 wherein R$_1$, R$_2$, R$_3$, R$_4$, R$_5$, R$_6$, R$_7$, R$_8$ and R$_9$ are independently selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, phenyl, substituted phenyl (where the substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, C$_{1-4}$alkylamino, C$_{1-4}$dialkylamino, halogen, perfluoro C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl, (where the substituents are independently selected from one or more of amino amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy or nitro, carboxy, cyano, sulfuryl or hydroxyl), triazin-2-yl-C$_{1-4}$alkyl, substituted triazin-2-yl-C$_{1-4}$alkyl (where the triazine substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazolylC$_{1-4}$alkyl, substituted imidazolylC$_{1-4}$alkyl (where the imidazole sustituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazolinylC$_{1-4}$alkyl, N-amidinopiperazinyl-N-C$_{0-4}$alkyl, hydroxyC$_{2-5}$alkyl, C$_{1-5}$alkylaminoC$_{2-5}$alkyl, C$_{1-5}$dialkylaminoC$_{2-5}$alkyl, N-amidinopiperidinylC$_{1-4}$alkyl and 4-aminocyclohexylC$_{0-2}$alkyl.

6. The method of claim 1, wherein A is —(CHR$_3$)—, B is —(C=O)—, D is —(CHR$_5$)—, E is —(C=O)—, G is —(XR$_7$)$_n$—, and the compound has the following general formula (II):

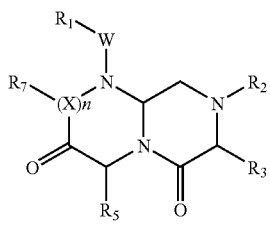

wherein R$_1$, R$_2$, R$_3$, R$_5$, R$_7$, W, X and n are as defined in claim 1.

7. The method of claim 1, wherein A is —(C=O)—, B is —(CHR$_4$)—, D is —(C=O)—, E is -(ZR$_6$)—, G is —(C=O)—(XR$_9$)—, and the compound has the structure of formula (III):

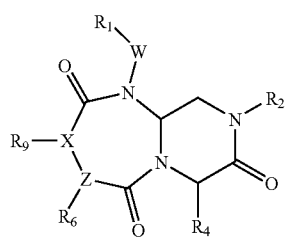

wherein R$_1$, R$_2$, R$_4$, R$_6$, R$_9$, W and X are as defined in claim 1, Z is nitrogen or CH (when Z is CH, then X is nitrogen).

8. The compound of claim 1, wherein A is (C=O)—, B is —(CHR$_4$)—, D is —(C=O)—, E is -(ZR$_6$)—, G is (XR$_7$)$_n$—, and the compound has the following general formula (IV):

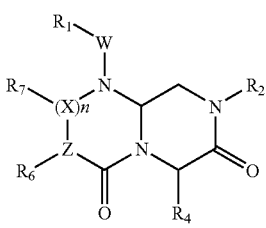

(IV)

wherein $R_1$, $R_2$, $R_4$, $R_6$, $R_7$, W, X and n are as defined in claim 1, and Z is nitrogen or CH, with the proviso that when Z is nitrogen, then n is zero, and when Z is CH, then X is nitrogen and n is not zero.

9. The method of claim 8, wherein the compound has the structure of formula (VI):

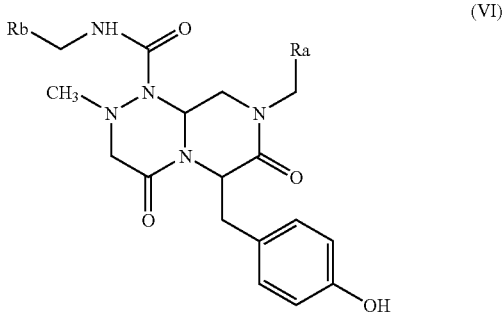

(VI)

wherein, $R_a$ is a bicyclic aryl group having 8 to 11 ring members, which may have 1 to 3 heteroatoms selected from nitrogen, oxygen or sulfur, and $R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy group.

10. The method of claim 9, wherein $R_a$ is naphthyl, quinolinyl or isoquinolinyl group, and $R_b$ is phenyl, pyridyl or piperidyl, all of which may be substituted with one or more substituents selected from a group consisting of halide, hydroxy, cyano, lower alkyl, and lower alkoxy group.

11. The method of claim 10, wherein $R_a$ is naphthyl, and $R_b$ is phenyl, which may be substituted with one or more substituents selected from a group consisting of halide, hydroxy, cyano, lower alkyl, and lower alkoxy group.

12. The method of claim 1 wherein the agent has the following structure:

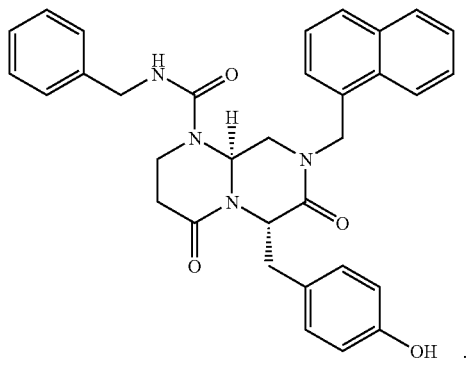

13. The method of claim 1, wherein the target gene is a gene encoding c-myc.

14. A method for decreasing the expression of a target gene induced by β-catenin, comprising contacting a stem cell with an agent having the structure of formula (I),

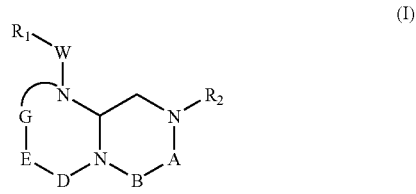

(I)

wherein A is —(CHR$_3$)— or —(C=O)—, B is —(CHR$_4$)— or —(C=O)—, D is —(CHR$_5$)— or —(C=O)—, E is -(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1; and $R_1$, $R_2$, $R_3$, $R_4$, $R_5$, $R_6$, $R_7$, $R_8$ and $R_9$ are each independently selected from an amino acid side chain moiety, a derivative of an amino acid side chain moiety, and stereoisomers thereof, and wherein the agent is contacted with the stem cell in an amount effective to decrease the expression of a target gene induced by β-catenin.

15. The method of claim 14, wherein $R_1$, $R_2$, $R_3$, $R_4$, $R_5$, $R_6$, $R_7$, $R_8$ and $R_9$ are independently selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, phenyl, substituted phenyl (where the substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, C$_{1-4}$alkylamino, C$_{1-4}$dialkylamino, halogen, perfluoro C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl, (where the substituents are independently selected from one or more of amino amidino, guanidino, hydrazino, C$_{1-4}$alkylamino, C$_{1-4}$dialkylamino, halogen, perfluoro C$_{1-4}$alkyl, C$_{1-4}$qalkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy or nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazolyl$C_{1-4}$alkyl, substituted imidazolyl$C_{1-4}$alkyl (where the imidazole sustituents are independently selected from one or more of amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazolinyl$C_{1-4}$alkyl, N-amidinopiperazinyl-N-$C_{0-4}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl.

16. The method of claim 14, wherein A is —(CHR$_3$)—, B is —(C=O)—, D is —(CHR$_5$)—, E is —(C=O)—, G is —(XR$_7$)$_n$—, and the compound has the following general formula (II):

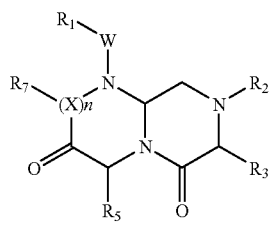

(II)

wherein R$_1$, R$_2$, R$_3$, R$_5$, R$_7$, W, X and n are as defined in claim 1.

17. The method of claim 14, wherein A is —(C=O)—, B is —(CHR$_4$)—, D is —(C=O)—, E is -(ZR$_6$)—, G is —(C=O)—(XR$_9$)—, and the compound has the structure of formula (III):

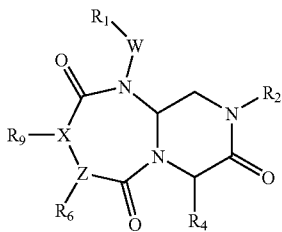

(III)

wherein R$_1$, R$_2$, R$_4$, R$_6$, R$_9$, W and X are as defined in claim 1, Z is nitrogen or CH (when Z is CH, then X is nitrogen).

18. The compound of claim 14, wherein A is —(C=O)—, B is —(CHR$_4$)—, D is —(C=O)—, E is -(ZR$_6$)—, G is (XR$_7$)$_n$—, and the compound has the following general formula (IV):

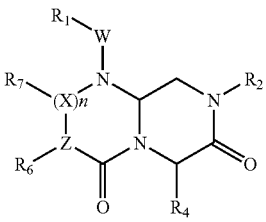

(IV)

wherein R$_1$, R$_2$, R$_4$, R$_6$, R$_7$, W, X and n are as defined in claim 1, and Z is nitrogen or CH, with the proviso that when Z is nitrogen, then n is zero, and when Z is CH, then X is nitrogen and n is not zero.

19. The method of claim 14, wherein the compound has the structure of formula (VI):

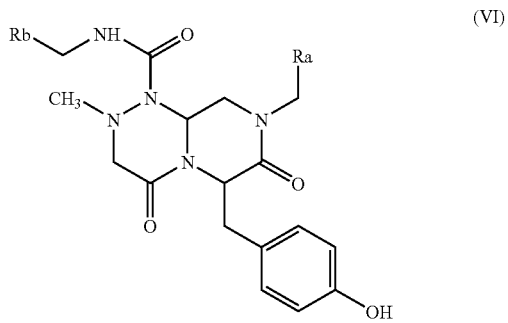

(VI)

wherein, R$_a$ is a bicyclic aryl group having 8 to 11 ring members, which may have 1 to 3 heteroatoms selected from nitrogen, oxygen or sulfur, and R$_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy group.

20. The method of claim 19, wherein R$_a$ is naphthyl, quinolinyl or isoquinolinyl group, and R$_b$ is phenyl, pyridyl or piperidyl, all of which may be substituted with one or more substituents selected from a group consisting of halide, hydroxy, cyano, lower alkyl, and lower alkoxy group.

21. The method of claim 20, wherein R$_a$ is naphthyl, and R$_b$ is phenyl, which may be substituted with one or more substituents selected from a group consisting of halide, hydroxy, cyano, lower alkyl, and lower alkoxy group.

22. The method of claim 14, wherein the target gene is a gene encoding cyclin D.

* * * * *

UNITED STATES PATENT AND TRADEMARK OFFICE
CERTIFICATE OF CORRECTION

| | | |
|---|---|---|
| PATENT NO. | : 7,531,320 B2 | Page 1 of 1 |
| APPLICATION NO. | : 10/928626 | |
| DATED | : May 12, 2009 | |
| INVENTOR(S) | : Michael Kahn et al. | |

It is certified that error appears in the above-identified patent and that said Letters Patent is hereby corrected as shown below:

Column 86
Line 64, "is (C=O)-" should read -- is –(C=O)- --.

Column 88
Line 48, "periluoro" should read -- perfluoro --.

Column 88
Line 58, "periluoro $C_{1-4}$alkyl, $C_{1-4}$qalkyl," should read -- perfluoro $C_{1-4}$alkyl, $C_{1-4}$alkyl, --.

Column 89
Line 7, "periluoro" should read -- perfluoro --.

Signed and Sealed this
Sixteenth Day of October, 2012

David J. Kappos
*Director of the United States Patent and Trademark Office*